(12) United States Patent
Debatin et al.

(10) Patent No.: US 6,369,109 B1
(45) Date of Patent: Apr. 9, 2002

(54) BETULINIC ACID AND DERIVATIVES THEREOF USEFUL FOR THE TREATMENT OF NEUROECTODERMAL TUMOR

(75) Inventors: Klaus Michael Debatin; Simone Fulda, both of Ulm; Manfred Wiessler, Frankenthal; Marek Los, Heidelberg; Walter Mier, Dossenheim, all of (DE)

(73) Assignee: Deutsches Krebsforschungszentrum Stiftung des Öffentlichen Rechts, Heidelberg (DE)

(*) Notice: Subject to any disclaimer, the term of this patent is extended or adjusted under 35 U.S.C. 154(b) by 0 days.

(21) Appl. No.: 09/182,588

(22) Filed: Oct. 28, 1998

(51) Int. Cl.$^7$ .......................... A61K 31/20; A61K 31/70
(52) U.S. Cl. ....................... 514/569; 514/120; 514/253; 514/258; 514/418; 514/570; 560/116; 560/194
(58) Field of Search ................................ 514/120, 253, 514/258, 418, 510, 569; 560/116, 194

(56) References Cited

U.S. PATENT DOCUMENTS

| | | |
|---|---|---|
| 5,658,947 A | 8/1997 | DasGupta et al. |
| 5,869,535 A | 2/1999 | Pezzuto et al. |

FOREIGN PATENT DOCUMENTS

| | | |
|---|---|---|
| WO | WO 96/29068 | 9/1996 |
| WO | WO 98/24795 | 6/1998 |

OTHER PUBLICATIONS

Adams et al., 1993 "Thoracic neuroblastoma: a Pediatric Oncology Group study,"*J. Ped. Surg.* 28:372–378.
Arai et al., 1991, "Ewing's sarcoma: local tumor control and patterns of failure following limited-volume radiation therapy,"*Int. J. Rad. Oncol. Biol. Phy.* 21:1501–1508.
Azizkhan and Haase, 1993,"Current biologic and therapeutic implications in the surgery of neuroblastoma," *Sem. Surg. Oncol.* 9:493–501.
Benzaquen et al., 1995, "Clotrimazole inhibits cell proliferation in vitro and in vivo," *Nature Medicine* 1:534–540.
Bowman et al., 1991," Impact of intensified therapy on clinical outcome in infants and children with neuroblastoma: the St Jude Children's Research Hospital experience, 1962 to 1988," *J. Clin. Oncol.* 9:1599–1608.
Bowman et al., 1997, "Genetic staging of unresectable or metastatic neuroblastoma in infants: a Pediatric Oncology Group study," *Natl. Cancer Inst.* 89:373–380.
Brodeur et al., 1993, "Revisions of the international criteria for neuroblastoma diagnosis, staging, and response to treatment," *J Clin. Oncol.* 11:1466–1477.
Brugnara et al., 1995, "Oral administration of clotrimazole and blockade of human erythrocyte Ca(++)–activated K+ channel: the imidazole ring is not required for inhibitory activity," *JPET* 273:266–272.

Brugnara et al., 1996, "Therapy with oral clotrimazole induces inhibition of the Gardos channel and reduction of erythrocyte dehydration in patients with sickle cell disease," *J. Clin. Invest.* 97(5):1227–1234.
Burgert et al., 1990, "Multimodal therapy for the management of nonpelvic, localized Ewing's sarcoma of bone: intergroup study IESS–II," *J. Clin. Oncol.* 8:1514–1524.
Buttitta et al., 1997, "p53 gene mutations predict chemoresistance in ovarian cancer," *Proc. Am. Assoc. Cancer Res.* 38:Abstract 713.
Carter et al., 1994, "Morphologic characteristics of lesion formation and time course of smooth muscle cell proliferation in a porcine proliferative restenosis model," *J. Am. Coll. Cardiol.* 24(5):1398–1405.
Castleberry et al., 1991, "Radiotherapy improves the outlook for patients older than 1 year with Pediatric Oncology Group stage C neuroblastoma," *J. Clin. Oncol.* 9:789–795.
Castleberry et al., 1992, "Infants with neuroblastoma and regional lymph node metastases have a favorable outlook after limited postoperative chemotherapy: a Pediatric Oncology Group study," *J. Clin. Oncol.* 10:1299–1304.
Corbett et al., 1996, "Preclinical anticancer activity of cryptophycin–8," *J. Exp. Ther. Oncol.* 1:95–108.
Debatin et al., 1997, "Cytotoxic drugs, programmed cell death, and the immune system: defining new roles in and old play," *J. Natl. Cancer Inst.* 89:750–751.
Delattre et al., 1994, "The Ewing family of tumors—a subgroup of small–round–cell tumors defined by specific chimeric transcripts," *New Engl. J. Med.* 331:294–299.
Dole et al., 1994, "Bcl–2 inhibits chemotherapy–induced apoptosis in neuroblastoma," *Cancer Res.* 54:3253–3259.
Dole et al., 1995, "Bcl0x$_L$ is expressed in neuroblastoma cells and modulates chemotherapy–induced apoptosis," *Cancer Res.* 55:2576–2582.
Dunst et al., 1995, "Radiation therapy in Ewing's sarcoma: an update of the CESS 86 trial," *Int. J. Radiation Oncology Biol. Phys.* 32:919–930.
Dykes et al., 1992, "Development of Human Tumor Xenograft Models for In Vivo Evaluation of New Antitumor Drugs," *Contrib. Oncol. Basel. Karger* 42:1–22.
Epstein et al., 1987, "Corneal neovascularization. Pathogenesis and inhibition," *Cornea* 6(4):250–257.

(List continued on next page.)

Primary Examiner—Gary Geist
Assistant Examiner—Howard V. Owens
(74) Attorney, Agent, or Firm—Pennie & Edmonds, LLP

(57) ABSTRACT

The present invention is, generally, directed to the use of betulinic acid and derivatives thereof for the treatment of neuroectodermal tumors. The present invention is based on the discovery that betulinic acid and its derivatives are potent anti-neuroectodermal agents. As disclosed herein, betulinic acid and its derivatives are useful for the treatment of neuroectodermal tumors, including, due to its distinct mechanism of action, neuroectodermal tumors that are resistant to conventional chemotherapeutical agents. In addition to the new use of known compounds, the invention discloses novel compounds and pharmaceutical compositions for the treatment of neuroectodermal tumors.

18 Claims, 38 Drawing Sheets

OTHER PUBLICATIONS

Figure 1A:
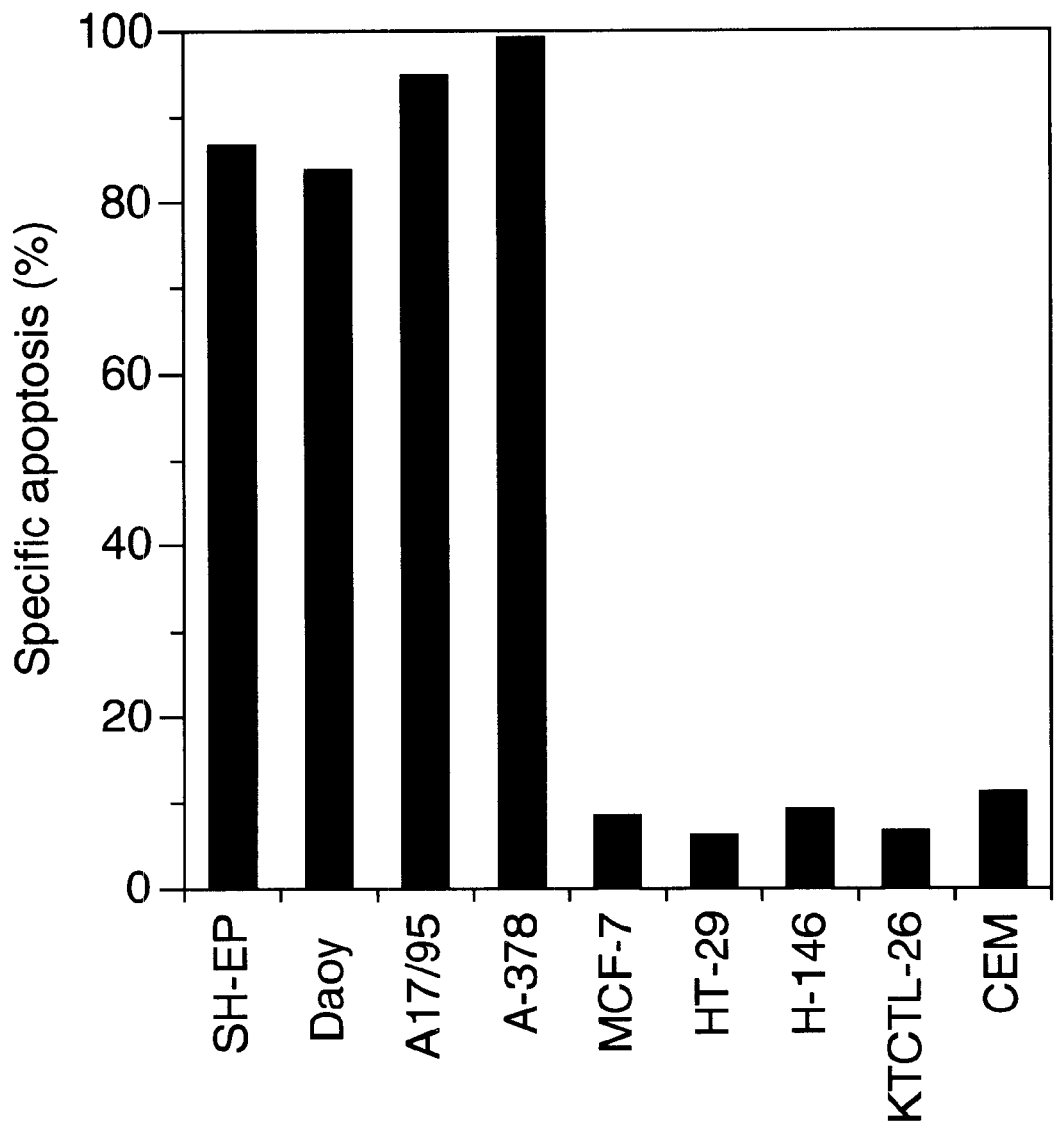

Evans et al., 1976, "Factors influencing survival of children with nonmetastatic neuroblastoma," *Cancer* 38:661–666.

Fingl and Woodbury, 1975, In: *The Pharmacological Basis of Therapeutics*, Ch. 1, pp. 1–46.

Fisher, 1994, "Apoptosis in cancer therapy: crossing the threshold," *Cell* 78:539–542.

Franks et al., 1997, "Neuroblastoma in adults and adolescents: an indolent course with poor survival," *Cancer* 79:2028–2035.

Friesen et al., 1996, "Involvement of the CD95 (APO–1/Fas) receptor/ligand system in drug–induced apoptosis in leukemia cells," *Nature Med.* 2:574–577.

Fuijoka et al., 1994, "Anti–AIDS agents, 11. Betulinic acid and platanic acid as anti–HIV principles from *Syzigium claviflorum*, and the anti–HIV activity of structurally related triterpenoids," *J. Nat. Prod.* 57(2):243–247.

Fulda et al., 1997, "The CD95 (APO–1/Fas) system mediates drug–induced apoptosis in neuroblastoma cells," *Cancer Res.* 57:3823–3829.

Fulda et al., 1997, "Betulinic acid triggers CD95 (APO–1/Fas) and p53–independent apoptosis via activation of caspases in neuroectodermal tumors," *Cancer Res.* 57:4956–4964.

Fulda et al., 1998, "Molecular ordering of apoptosis induced by anticancer drugs in neuroblastoma cells," *Cancer Res.* 58:4453–4460.

Grier et al., 1994, "Improved Outcome in Non–metastatic Ewing's Sarcoma (Ews) and PNET of Bone with the Addition of Ifosfamide (I) and Etoposide (E) to Vincristine (V), Adriamycin (Ad), Cyclophosphamide (C), and Actinomycin (A): a Childrens Cancer Group (CCG) and Pediatric Oncology Group (POG) Report," *Proc. Am. Soc. Clin. Oncol.* 13:Abstract 1443.

Helferich and Goerdeler, 1940, "Zur Synthese von β–d–Glucosiden," *Ber. Dtsch. Chem. Ges.* 73:532–541.

Jennings et al. 1993, "Fetal neuroblastoma: prenatal diagnosis and natural history," *J. Ped. Surg.* 28:1168–1174.

Johnstone and Rose, 1979, "A rapid, simple, and mild procedure for alkylation of phenols, alcohols, amides and acids," *Tetrahedron* 35:2169–2173.

Kaiser and Woodruff,1970, "Synthesis of esters of acid–unstable alcohols by means of n–butyllithium," *J. Org. Chem.* 35:1198–1199.

Kerr et al., 1972, "Apoptosis: a basic biological phenomenon with wide–ranging implications in tissue kinetics," *Br. J. Cancer* 26:239–257.

Kinsella et al., 1991, "Long–term follow–up of Ewing's sarcoma of bone treated with combined modality therapy," *Int. J. Radiation Oncology Biol. Phys.* 20:389–395.

Koenigs and Knorr, 1901, "Ueber einige Derivate des Traubenzuckers und der Galactose," *Ber. Dtsch. Chem. Ges.* 34:957–981.

Koopman et al., 1994, "Annexin V for flow cytometric detection of phosphatidylserine expression on B cells undergoing apoptosis," *Blood* 84:1415–1420.

Kroemer et al., 1997, "Mitochondrial control of apoptosis," *Immunol. Today* 18:44–51.

Llombart–Bosch et al., 1990, "Soft tissue Ewing's sarcoma. Characterization in established cultures and xenografts with evidence of a neuroectodermic phenotype," *Cancer* 66:2589–2601.

Los et al., 1995, "Requirement of an ICE/CED–3 protease for Fas/APO–1–mediated apoptosis," *Nature (Lond.)* 375:81–83.

Lowe et al., 1994, "p53 status and the efficacy of cancer therapy in vivo," *Science* 266:807–810.

McWilliams et al., 1995, "Cyclophosphamide/doxorubicin vs. cisplatin/teniposide in the treatment of children older than 12 months of age with disseminated neuroblastoma: a Pediatric Oncology Group Randomized Phase II study," *Med. Pediatr. Oncol.* 24:176–180.

Medema et al., 1997, "FLICE is activated by association with the CD95 death–inducing signaling complex (DISC)," *EMBO J.* 16:2794–2804.

Meyer zu Reckendorf, 1968, "Notiz über Eliminierungsreaktionen der myo–scyllo–inosose," *Chem. Ber.* 101:3652–3654.

Micheau et al., 1997, "Sensitization of cancer cells treated with cytotoxic drugs to fas–mediated cytotoxicity," *J. Natl. Cancer Inst.* 89:783–789.

Miyashita and Reed, 1995, "Tumor suppressor p53 is a direct transcriptional activator of the human bax gene," *Cell* 80:293–299.

Nesbit et al., 1990, "Multimodal therapy for the management of primary, nonmetastatic Ewing's sarcoma of bone: a long–term follow–up of the First Intergroup study," *J. Clin. Oncol.* 8:1664–1674.

Nicoletti et al., 1991, "A rapid and simple method for measuring thymocyte apoptosis by propidium iodide staining and flow cytometry," *J. Immunol. Methods* 139:271–279.

Ohara and Hishiyama, 1994, "Utilization of Triterpenoids I. Synthesis of betulin glycosides by clodextrin glycosyltransferase," *Mokuzai Gakkaishi* 40(4):444–451.

Pancharoen et al., 1994, "Triterpenoid glycosides from *Schefflera lucantha*," *Phytochemistry* 35(4):987–992.

Rosen et al., 1981, "Ewing's sarcoma: ten–year experience with adjuvant chemotherapy," *Cancer* 47:2204–2213.

Scaffidi et al., 1997, "FLICE is predominantly expressed as two functionally active isoforms, caspase–8/a and caspase–8/b," *J. Biol. Chem.* 272:26953–26958.

Schwarz, 1962, "Steroid–derivate XVIII. Selektiver schutz der hydroxylgruppen in steroid–verbin–dungen durch die trichloracetoxygruppe," *Collection Czechoslov. Chem. Commun.* 27:2567–2574.

Smith et al., 1991, "Influence of doxorubicin dose intensity on response and outcome for patients with osteogenic sarcoma and Ewing's sarcoma," *J. Natl. Cancer Inst.* 83:1460–1470.

Suda et al., 1993, "Molecular cloning and expression of the Fas ligand, a novel member of the tumor necrosis factor family," *Cell* 75:1169–1178.

Susin et al., 1996, "Bcl–2 inhibits the mitochondrial release of an apoptogenic protease," *J. Exp. Med.* 184:1331–1341.

Susin et al., 1997, "A cytofluorometric assay for nuclear apoptosis induced in a cell–free system: application to ceramide–induced apoptosis," *Exp. Cell Res.* 236:397–403.

Susin et al., 1997, "The central executioner of apoptosis: multiple connections between protease activation and mitochondria in Fas/APO–1/CD95–and ceramide–induced apoptosis," *J. Exp. Med.* 186:25–37.

Tanaka et al., 1995, "Expression of the functional soluble form of human Fas ligand in activated lymphocytes," *EMBO J*. 14:1129–1135.

Trauth et al., 1989, "Monoclonal antibody–mediated tumor regression by induction of apoptosis," *Science* 245:301–305.

Uvarova et al., 1980, "Synthesis of triterpene and steroid glycosides," *Carbohydrate Research* 83:33–42.

Wu et al., 1986, "Expression of $G_{D2}$ ganglioside by untreated primary human neuroblastomas," *Cancer Res*. 46:440–443.

Zamzami et al., 1996, "Mitochondrial control of nuclear apoptosis," *J. Exp. Med*. 183:1533–1544.

Zhu et al., 1994, "Effects of etidronate and lovastatin on the regression of atherosclerosis in cholesterol–fed rabbits," *Cardiology* 85(6):370–377.

Schmidt et al., 1997, "Betulinic Acid Induces Apoptosis in Human Neuroblastoma Cell Lines," *European Journal of Cancer* 33: 2007–2010.

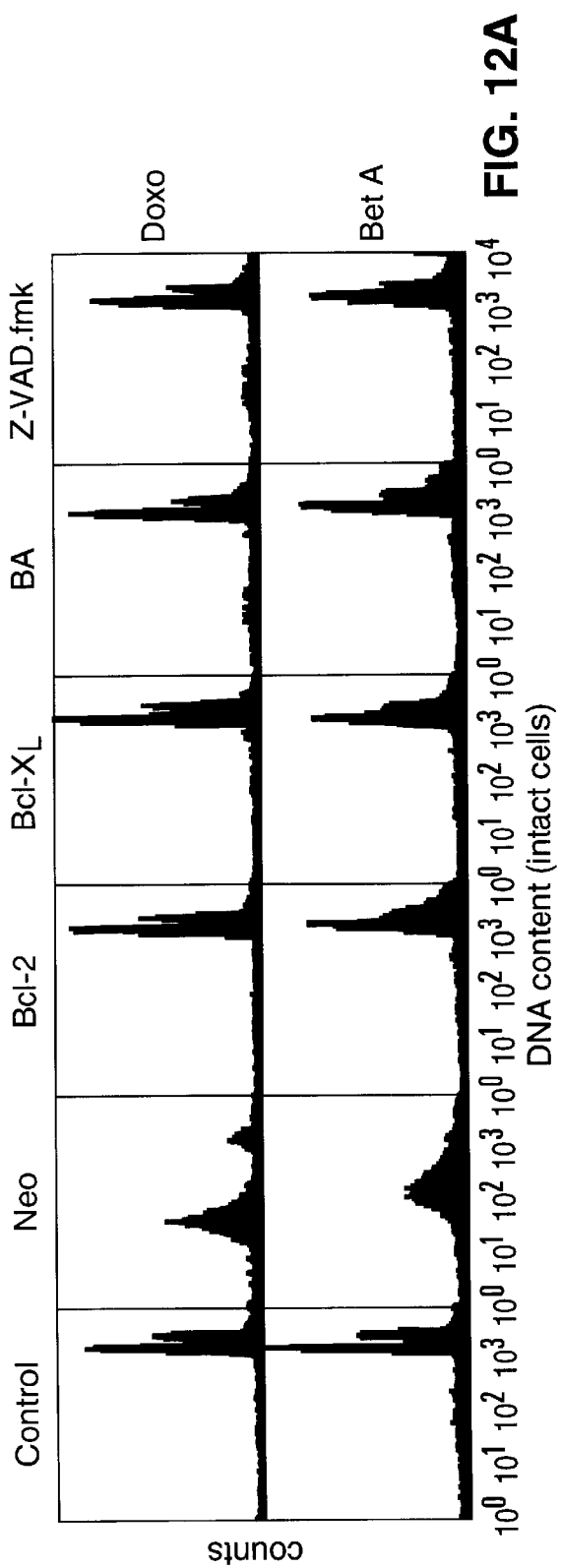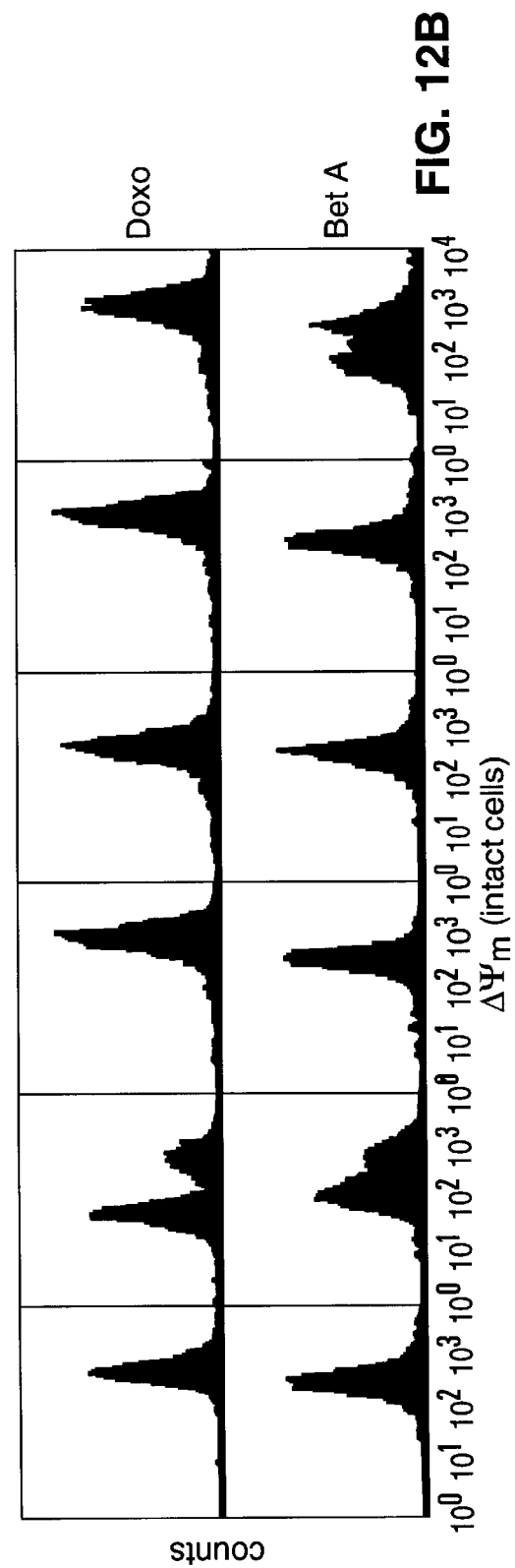
FIG. 12A
FIG. 12B

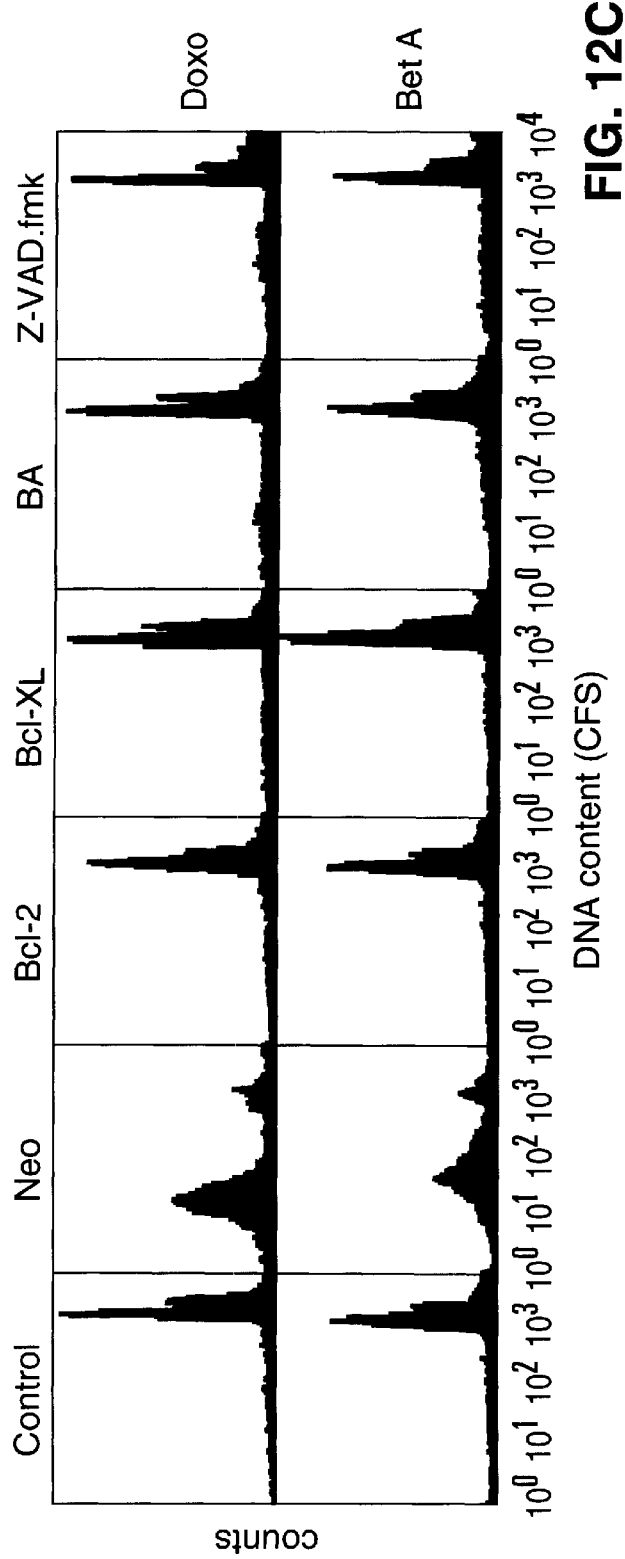
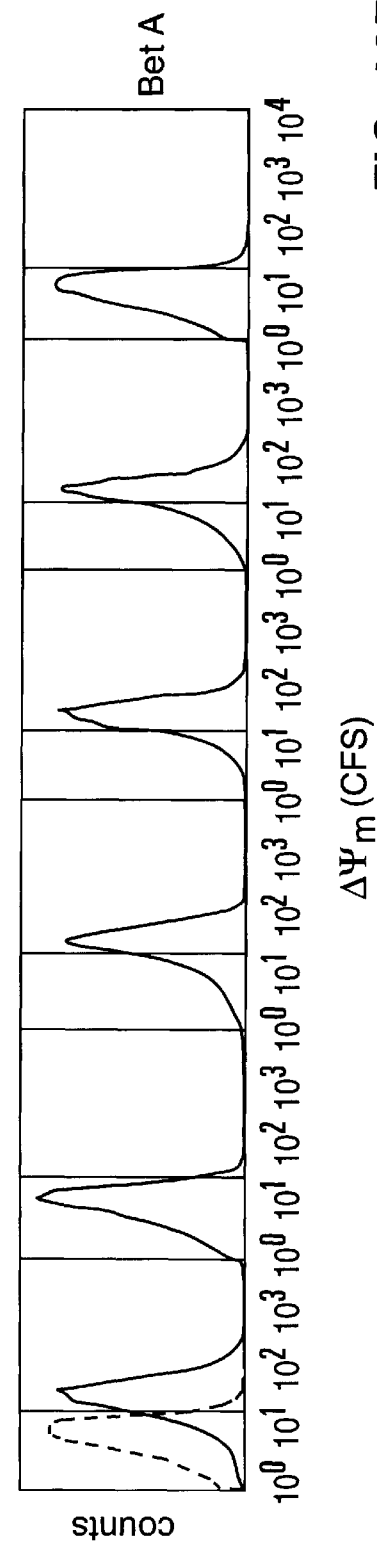
FIG. 12C
FIG. 12D

BETULINIC ACID AND DERIVATIVES THEREOF USEFUL FOR THE TREATMENT OF NEUROECTODERMAL TUMOR

I. FIELD OF INVENTION

The present invention relates to the field of cancer treatment and is based on the discovery that betulinic acid and its derivatives are potent anti-neuroectodermal agents. As disclosed herein, betulinic acid and its derivatives are useful for the treatment of neurodectodermal tumors, due to its distinct mechanism of action, including neuroectodermal tumors that are resistant to conventional chemotherapeutical agents. In addition to the new use of known compounds, the invention discloses novel compounds and pharmaceutical compositions for the treatment of neuroectodermal tumors.

II. BACKGROUND OF INVENTION

Neuroectodermal tumors, such as neuroblastoma, medulloblastoma, and Ewing's sarcoma, representing the most common solid tumors of childhood. Chemotherapy is the primary treatment for many types of neuroectodermal tumors. Two thirds of the neuroblastoma cases occur in children of 5 years of age or younger. The early onset of neuroblastoma is illustrated by prenatal neuroblastoma detectable by fetal ultrasonography. Jennings et al 1993, *J. Ped. Surg.* 28:1168–1174. Neuroblastoma originates in the adrenal medulla or the paraspinal sites where sympathetic nervous system tissue is present. Neuroblastoma presents serious clinical consequences including symptoms associated with tumor mass or bone pain from metastases. Because they originate in paraspinal ganglia, neuroblastomas may invade through neural foramina and compress the spinal cord, causing paralysis. Azizkhan and Haase, 1993, *Sem. Surg. Oncol.* 9: 493–501. Approximately 70% of all patients with neuroblastoma have metastatic disease at diagnosis. See, e.g., Brodeur et al., 1993, *J. Clin. Oncol.* 11: 1466–1477; Adams et al., 1993, *J. Ped. Surg.* 28:372–378; Evans et al., 1976, *Cancer* 38:661–666.

Chemotherapy remains to be one of the most effective treatments for neuroblastoma tumors. Neuroblastoma patients are generally treated with chemotherapy with cyclophosphamide and doxorubicin, cisplatin with teniposide or etoposide or vincristine with cisplatin and teniposide or etoposide for more resistant tumors. For patients younger than one year, aggressive chemotherapy using combinations of cyclophosphamide, doxorubicin, cisplatin, and teniposide or etoposide is generally used. Castleberry et al., 1991, *J. Clin. Oncol.* 9:789–795; Bowman et al., 1997, *J. Natl. Cancer Inst.* 89:373–380; Castleberry et al., 1992, *J. Clin. Oncol.* 10:1299–1304.

Aggressive multiagent chemotherapy has resulted in a 2-year survival rate of approximately 20% in older children with stage IV neuroblastoma. Bowman et al., 1991, *J. Clin. Oncol.* 9:1599–1608; Williams et al., 1995, *Med. Ped. Oncol.* 24:176–180. Neuroblastoma in the adolescent or adult has a worse long-term prognosis regardless of stage or site and, in many cases, a more prolonged course. Franks et al., 1997, *Cancer* 79: 2028–2035.

Ewing's sarcoma (EWS) usually occurs in bone and is diagnosed most frequently in the second decade of life. The most common sites for the primary lesion are the pelvic bones, femur, humerus, and ribs. Ewing's sarcoma occurs less commonly at non-bone primary sites, a presentation that has historically been termed extraosseous Ewing's sarcoma. However, the morphological and biological characteristics of Ewing's tumors developing in soft tissues appear to be indistinguishable from those of tumors developing at bone sites. Delattre et al., 1994, *New Engl. J. Med.* 331:294–299; Llombart-Bosch et al., 1990, *Cancer* 66:2589–2601.

Primitive neuroectodermal tumors (PNETs) have been referred to by different terms depending on their location and extent of neural differentiation: peripheral neuroepithelioma, Askin tumor, adult neuroblastoma, peripheral neuroblastoma, and primitive neuroectodermal tumors. The collective term is primitive neuroectodermal tumors. Ewing's sarcoma and PNET represent a biological spectrum of the same tumor. Greater than 90% of these tumors are characterized by chromosome 11/22 translocation. Since these tumors exhibit only neuroectodermal markers of differentiation, it has been suggested that they arise from neural crest cells. Because treatment is the same for these tumors, they are often referred to as Ewing's sarcoma.

Studies suggest that more than 50% of patients without metastatic disease may have a long-term disease-free survival, compared to only 20–30% for patients who present with metastatic disease. See, e.g., Burgert et al., 1990, *J. Clin. Oncol.* 8:1514–1524; Grier et al., 1994, *Proc. Am. Soc. Clin. Oncol.* 13: A-1443; Rosen et al., 1981, *Cancer* 47:2204–2213; Dunst et al., 1995, *Int. J. Rad. Oncol. Biol. Phy.* 32:919–930; Arai et al., 1991, *Int. J. Rad. Oncol. Biol. Phy.* 21:1501–1508.

Surgery of Ewing's sarcoma is usually limited to the initial diagnostic biopsy of the primary tumor. Patients usually underwent induction chemotherapy followed by radiation therapy for local control. The successful treatment of patients with Ewing's sarcoma requires the use of multidrug chemotherapy. Combination chemotherapy for Ewing's sarcoma has traditionally included vincristine, doxorubicin, cyclophosphamide, and dactinomycin (VAdriaC or VAC). The importance of doxorubicin has been demonstrated in randomized comparative trials with increased doxorubicin dose intensity during the early months of therapy resulting in improved event-free survival. See, e.g., Nesbit et al., 1990, *J. Clin. Oncol.* 8:1664–1674; Kinsella et al., 1991, *Int. J. Radiat. Oncol. Biol. Phy.* 20:389–395; Smith et al., 1991, *J. Natl. Cancer Inst.* 83:1460–1470.

Although many neuroectodermal tumors initially respond to chemotherapy, the prognosis of children who relapse or present with disseminated disease remain poor, because of the development of drug resistance. Some chemotherapeutical agents, such as doxorubicin, rely upon the presence of functioning CD95 system in the target tumor cells to exert their anti-tumor activities. Cells lacking functional CD95 are resistant to doxorubicin. Some other chemotherapeutical agents relay upon the presence of a functional p53 system to exert their anti-tumor activities. Such chemotherapeutical agents are ineffective against cells lacking functional p53 protein.

Therefore, there is a great need to develop chemotherapeutical drugs that target neuroectodermal tumors and particularly drug resistant neuroectodermal tumors. Accordingly, this invention provides chemical compositions and the use thereof for the treatment of neuroectodermal tumors. Those compositions do not relay upon the CD95 or p53 systems to exert their anti-tumor activities.

II. SUMMARY OF THE INVENTION

The present invention provides novel compounds, useful for treatment of neuroectodermal tumors, having the general formula (I):

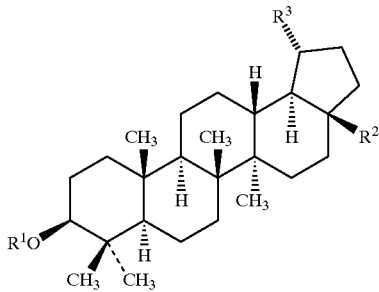

(I)

wherein
R¹ is selected from the group consisting of hydrogen, —SO₃H, —PO₃H₂, —C₁–C₂₀ straight or branched chain alkenyl, —C₂–C₂₀ straight or branched chain alkenyl, —C₂–C₂₀ straight or branched chain alkynyl, —(CH₂CH₂O)$_n$H, —(CH₂CH₂O)$_n$CH₃, —(CH₂CH₂O)$_n$CH₂CH₃, —C(O)C₆H₅, —C(O)C₁–C₂₀ straight or branched chain alkyl, —C(O)C₂–C₂₀ straight or branched chain alkenyl, —C(O)C₂–C₂₀ straight or branched chain alkynyl, myo-inosityl, scyllo-inosityl, a cyclitol, conduritol A, quebrachitol, a monosaccharide, a disaccharide and an oligosaccharide; the —(CH₂CH₂O)$_n$H, myo-inosityl, scyllo-inosityl, cyclitol, conduritol A, quebrachitol, monosaccharide, disaccharide and oligosaccharide being optionally substituted with one or more —C(O)C₁–C₂₀ straight or branched chain alkyl, —C(O)C₂–C₂₀ straight or branched chain alkenyl, —C(O)C₂–C₂₀ straight or branched chain alkynyl, sulfate, or mono-, di- or tri-phosphate groups;

R² is selected from the group consisting of —CO₂H, —CO₂(C₆H₅), —CO₂(C₁–C₂₀ straight or branched chain alkyl), —CO₂(C₂–C₂₀ straight or branched chain alkenyl), —CO₂(C₂–C₂₀ straight or branched chain alkynyl), —CO₂(myo-inosityl), —CO₂(scyllo-inosityl), —CO₂(cyclitol), —CO₂(conduritol A), —CO₂(quebrachitol), —CO₂(monosaccharide), —CO₂(disaccharide), —CO₂(oligosaccharide), —CO(OCH₂CH₂)$_n$OH, —CO(OCH₂CH₂)$_n$OCH₃, —CO(OCH₂CH₂)$_n$OCH₂CH₃, —CH₂OH, —CH₂OSO₃H, —CH₂OPO₃H₂, —CH₂O(C₆H₅), —CH₂O(C₁–C₂ straight or branched chain alkyl), —CH₂O(C₂–C₂₀ straight or branched chain alkenyl), —CH₂O(C₂–C₂₀ straight or branched chain alkynyl), —CH₂O₂C(C₁–C₂₀ straight or branched chain alkyl), —CH₂O₂C(C₂–C₂₀ straight or branched chain alkenyl), —CH₂O₂C(C₂–C₂₀ straight or branched chain alkynyl), —CH₂O(myo-inosityl), —CH₂O(scyllo-inosityl), —CH₂O(cyclitol), —CH₂O(conduritol A), —CH₂O(quebrachitol), —CH₂O(monosaccharide), —CH₂O(disaccharide), —CH₂O(oligosaccharide), —CH₂(OCH₂CH₂)$_n$OH, —CH₂(OCH₂CH₂)$_n$OCH₃, —CH₂(OCH₂CH₂)$_n$OCH₂CH₃, —CH₂O₂C(OCH₂CH₂)$_n$OH, —CH₂O₂C(OCH₂CH₂)$_n$OCH₃, and —CH₂O₂C(OCH₂CH₂)$_n$OCH₂CH₃; the myo-inosityl, scyllo-inosityl, cyclitol, conduritol A, quebrachitol, monosaccharide, disaccharide, oligosaccharide, —CH₂(OCH₂CH₂)$_n$OH and —CH₂O₂C(OCH₂CH₂)$_n$OH being optionally substituted with one or more —C(O)C₁–C₂₀ straight or branched chain alkyl, —C(O)C₂–C₂₀ straight or branched chain alkenyl, —C(O)C₂–C₂₀ straight or branched chain alkynyl, sulfate, or mono-, di- or tri-phosphate groups;

R³ is selected from the group consisting of —C(CH₃)(=CH₂) and —CH(CH₃)₂;
each n is independently an integer from 1 to 20;
D-enantiomers, L-enantiomers, and racemates thereof;
and pharmaceutically acceptable salts thereof;
with the proviso that the compound of formula I is not:
3β-3-hydroxylup-20(29)-en-28-oic acid ("betulinic acid");
3β-lup-20(29)-ene-3,28-diol ("betulin");
3β-lup-20(29)-ene-3,28-diol diacetate ("3,28-diacetylbetulin");
3β-3-(acetyloxy)lup-20(29)-en-28-oic acid ("3-acetylbetulinic acid");
3β-3-(1-oxobutoxy)lup-20(29)-en-28-oic acid ("3-butyrylbetulinic acid");
3β-3-(2,3-dihydroxycinnamoyl)lup-20(29)-en-28-oic acid ("3-(2,3-dihydroxycinnamoyl)betulinic acid");
3β-lup-20(29)-ene-3,28-diol 3-acetate ("3-acetylbetulin");
3β-lup-20(29)-ene-3,28-diol 28-acetate ("28-acetylbetulin");
3β-3-hydroxylup-20(29)-en-28-oic acid methyl ester ("methyl betulinate");
3β-3-(acetyloxy)lup-20(29)-en-28-oic acid methyl ester ("methyl 3-acetylbetulinate");
3β-3-hydroxylup-20(29)-en-28-oic acid ethyl ester ("ethyl betulinate");
3β-3-hydroxylup-20(29)-en-28-oic acid butyl ester ("butyl betulinate");
3β-lupane-3,28-diol ("dihydrobetulin");
3β-3-hydroxylupan-28-oic acid ("dihydrobetulinic acid");
3β-3-hydroxylupan-28-oic acid methyl ester ("methyl dihydrobetulinate");
3β-3-(acetyloxy)lupan-28-oic acid methyl ester ("methyl 3-acetyldihydrobetulinate");
3β-3-(acetyloxy)-lupan-28-oic acid ("3-acetyldihydrobetulinic acid");
3β-lupane-3,28-diol diacetate ("3,28-diacetyldihydrobetulin");
3β-lupane-3,28-diol dibutanoate ("3,28-dibutyryldihydrobetulin");
3β-3-(3-methyl-1-oxobutoxy)lupan-28-oic acid ("3-(3-methylbutryryl)dihydrobetulinic acid");
3β-3-((1-oxo-2-butenyl)oxy)lup-20(29)-en-28-oic acid ("3-(trans-2-butenyl)betulinic acid");
3β-3-(2,2-dimethyl-1-oxopropoxy)lupan-28-oic acid ("3-(2,2-dimethylpropionyl)dihydrobetulinic acid");
3α-28-hydroxylup-20(29)-en-3-yl-6-O-(6-deoxy-α-L-mannopyranosyl)-β-D-glucopyranoside;
3α-28-hydroxylup-20(29)-en-3-yl-β-D-glucopyranoside;
3α,4α-3-(β-D-glucopyranosyloxy)lup-20(29)-en-28-oic acid;
3-(β-D-glucopyranosyloxy)lup-20(29)-en-28-oic acid;
3β-28-hydroxylup-20(29)-en-3-yl-β-D-glucopyranoside;
3β-3-hydroxylup-20(29)-en-28-yl-β-D-glucopyranoside;
3β-28(acetyloxy)lup-20(29)-en-3-yl-2-deoxy-α-D-arabinohexopyranoside triacetate;
3β-28(acetyloxy)lup-20(29)-en-3-yl-2-deoxy-β-L-arabinohexopyranoside triacetate;
3β-28(acetyloxy)lup-20(29)-en-3-yl-2,6-dideoxy-β-L-arabinohexopyranoside diacetate;
3β-3-(acetyloxy)lup-20(29)-en-28-yl-2-deoxy-α-D-arabinohexopyranoside triacetate;
3β-3-(acetyloxy)lup-20(29)-en-28-yl-2,6-dideoxy-β-L-arabinohexopyranoside diacetate;
3β-28-hydroxylup-20(29)-en-3-yl-2-deoxy-β-D-arabinohexopyranoside;
3β-28-hydroxylup-20(29)-en-3-yl-2-deoxy-β-L-arabinohexopyranoside;

3β-28-hydroxylup-20(29)-en-3-yl-2,6-dideoxy-β-L-arabinohexopyranoside;

3β-3-hydroxylup-20(29)-en-28-yl-2-deoxy-α-D-arabinohexopyranoside;

3β-lup-20(29)-en-3,28-diyl-bis-β-D-glucopyranoside;

3β-lup-20(29)-en-3,28-diyl-bis-4-O-α-D-glucopyranosyl-β-D-glucopyranoside;

3β-lup-20(29)-en-3,28-diyl-bis-(4-O-(2,3,4,6-tetra-O-acetyl-α-D-glucopyranosyl)-β-D-glucopyranoside hexaacetate;

3β-3-((4-O-α-D-glucopyranosyl-β-D-glucopyranosyl)oxy)lup-20(29)-en-28-oic acid;

3β-3-((6-O-β-D-glucopyranosyl-β-D-glucopyranosyl)oxy)lup-20(29)-en-28-oic acid;

3β-3-hydroxylup-20(29)-en-28-yl-2,6-dideoxy-β-L-arabinohexopyranoside;

3β-3-((2-O-α-L-arabinopyranosyl-6-deoxy-β-D-glucopyranosyl)oxy)lup-20(29)-en-28-oic acid;

3β-3-((2-O-β-D-glucopyranosyl-β-D-glucopyranosyl)oxy)lup-20(29)-en-28-oic acid;

3β-3-hydroxylup-20(29)-en-28-oic acid 2,3,4,6-tetra-O-acetyl-β-D-glucopyranosyl ester;

3β-3-hydroxylup-20(29)-en-28-oic acid β-D-galactopyranosyl ester;

3β-3-hydroxylup-20(29)-en-28-oic acid 4-O-β-D-galactopyranosyl-β-D-glucopyranosyl ester;

3β-3-((2,3,4,6-tetra-O-acetyl-β-D-glucopyranosyl)oxy)lup-20(29)-en-28-oic acid methyl ester;

3β-3-(acetyloxy)lup-20(29)-en-28-oic acid 2,3,4,6-tetra-O-acetyl-β-D-glucopyranosyl ester;

3β-3-(acetyloxy)lup-20(29)-en-28-oic acid β-D-glucopyranosyl ester;

3β-3-((2,3,4,6-tetra-O-acetyl-β-D-glucopyranosyl)oxy)lup-20(29)-en-28-oic acid 2,3,4,6-tetra-O-acetyl-β-D-glucopyranosyl ester;

3β-3-((2,3,4,6-tetra-O-acetyl-β-D-glucopyranosyl)oxy)lupan-28-oic acid methyl ester;

3β-3-(acetyloxy)lupan-28-oic acid 2,3,4,6-tetra-O-acetyl-β-D-glucopyranosyl ester;

3α-3-((2,3,4,6-tetra-O-acetyl-β-D-glucopyranosyl)oxy)lup-20(29)-en-28-oic acid;

3β-3-((2,3,4,6-tetra-O-acetyl-β-D-glucopyranosyl)oxy)lup-20(29)-en-28-oic acid;

3β-3-(acetyloxy)lupan-28-oic acid β-D-glucopyranosyl ester;

3β-3-hydroxylup-20(29)-en-28-oic acid β-D-glucopyranosyl ester;

3β-3-hydroxylup-20(29)-en-28-oic acid β-D-xylopyranosyl ester;

3β-hydroxylup-20(29)-en-28-oic acid β-D-glucopyranosyl ester 2',3',4',6'-tetrabenzoate;

3β-lup-20(29)-en-28-oic acid (β-D-glucopyranosyloxy)-β-D-glucopyranosyl ester octabenzoate;

3β-lup-20(29)-en-28-oic acid (α-L-arabinopyranosyloxy)-α-L-arabinopyranosyl ester;

3β-lup-20(29)-en-28-oic acid (α-L-arabinopyranosyloxy)-α-L-arabinopyranosyl ester hexabenzoate;

3β-3-(β-D-glucopyranosyloxy)lup-20(29)-en-28-oic acid methyl ester;

3β-3-(β-D-glucopyranosyloxy)lupan-28-oic acid methyl ester;

3β-3-hydroxylupan-28-oic acid β-D-glucopyranosyl ester;

3β-17-carboxy-28-norlup-20(29)-en-3-yl-3-O-β-D-xylopyranosyl-β-D-glucopyranosiduronic acid;

3β-17-carboxy-28-norlup-20(29)-en-3-yl-2-O-β-D-xylopyranosyl-β-D-glucopyranosiduronic acid;

3β-3-(β-D-glucopyranosyloxy)lup-20(29)-en-28-oic acid 6-O-β-D-glucopyranosyl-β-D-glucopyranosyl ester;

3α-3-hydroxylup-20(29)-en-28-oic acid O-6-deoxy-α-L-mannopyranosyl-(1→4)-O-β-D-glucopyranosyl-(1→6)-O-β-D-glucopyranosyl ester;

3α-3-(β-D-glucopyranosyloxy)lup-20(29)-en-28-oic acid O-6-deoxy-α-L-mannopyranosyl-(1→4)-O-β-D-glucopyranosyl-(1→6)-O-β-D-glucopyranosyl ester;

3β-3-(β-D-glucopyranosyloxy)lup-20(29)-en-28-oic acid O-6-deoxy-α-L-mannopyranosyl-(1→4)-O-β-D-glucopyranosyl-(1→6)-O-β-D-glucopyranosyl ester;

3β-28-methoxy-28-oxolup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid methyl ester diacetate;

3β-17-carboxy-28-norlup-20(29)-en-3-yl-O-6-deoxy-α-L-mannopyranosyl-(1→2)-O-β-D-glucopyranosyl-(1→2)-β-D-glucopyranosiduronic acid;

3β-17-carboxy-28-norlup-20(29)-en-3-yl-O-6-deoxy-α-L-mannopyranosyl-(1→2)-O-β-D-xylopyranosyl-(1→2)-β-D-glucopyranosiduronic acid;

3β-17-carboxy-28-norlup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid diacetate;

3β-17-carboxy-28-norlup-20(29)-en-3-yl-O-2,3,4-tri-O-acetyl-6-deoxy-α-L-mannopyranosyl-(1→2)O-3,4-di-O-acetyl-β-D-xylopyranosyl-(1→2)-β-D-glucopyranosiduronic acid diacetate;

3β-28-methoxy-28-oxolup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid methyl ester diacetate;

3β-28-methoxy-28-oxolup-20(29)-en-3-yl-O-2,3,4-tri-O-acetyl-6-deoxy-α-L-mannopyranosyl-(1→2)-O-3,4-di-O-acetyl-β-D-xylopyranosyl-(1→2)-β-D-glucopyranosiduronic acid methyl ester diacetate;

3β-3-((O-α-L-arabinofuranosyl-(1→2)-O-6-deoxy-α-L-matnopyranosyl-(1→4)-β-D-glucopyranosyl)oxy)lup-20(29)-en-28-oic acid;

3β-3-((O-α-L-arabinofuranosyl-(1→2)-O-6-deoxy-α-L-mannopyranosyl-(1→4)-β-D-glucopyranosyl)oxy)-lup-20(29)-en-28-oic acid methyl ester;

3β-28-hydroxylup-20(29)-en-3-yl-4-O-β-D-glucopyranosyl-β-D-glucopyranoside;

3β-28-hydroxylup-20(29)-en-3-yl-4-O-α-D-glucopyranosyl-β-D-glucopyranoside;

3β-3-hydroxylup-20(29)-en-28-yl-4-O-α-D-glucopyranosyl-β-D-glucopyranoside;

3β-28-hydroxylup-20(29)-en-3-yl-β-D-xylopyranoside;

3-(β-D-glucopyranosyloxy)lup-20(29)-en-28-oic acid O-6-deoxy-α-L-mannopyranosyl-(1→4)-O-β-D-glucppyranosyl-(1→6)-O-β-D-glucopyranosyl ester;

3α-lup-20(29)-en-28-oic acid 3-(β-D-glucopyranosyloxy)-O-6-deoxy-α-L-mannopyranosyl-(1→4)-O-β-D-glucopyranosyl-(1→6)-O-β-D-glucopyranosyl ester;

3α,4-α-3-(β-D-glucopyranosyloxy)lup-20(29)-en-28-oic acid;

3α-lup-20(29)-en-28-oic acid 3-((O-6-acetyl-β-D-glucopyranosyl)oxy)-O-6-deoxy-α-L-mannopyranosyl-(1→4)-O-β-D-glucopyranosyl-(1→6)-O-β-D-glucopyranosyl ester;

3β-28-hydroxylup-20(29)-en-3-yl-O-α-D-glucopyranosyl-(1→4)-O-α-D-glucopyranosyl-(1→4)-O-β-D-glucopyranosyl-(1→4)-β-D-glucopyranoside;

3α-3-(sulfooxy)lup-20(29)-en-28-oic acid 28-O-6-deoxy-α-L-mannopyranosyl-(1→4)-O-β-D-glucopyranosyl-(1→6)-β-D-glucopyranosyl ester;

3-(sulfooxy)lup-20(29)-en-28-oic acid 28-(O-2,3,4-tri-O-acetyl-6-deoxy-α-L-mannopyranosyl-(1→4)-O-2,3,6-tri- O-acetyl-β-D-glucopyranosyl-(1→6)-2,3,4-tri-O-acetyl-β-D-glucopyranosyl) ester;

3α-3-(acetyloxy)lup-20(29)-en-28-oic acid O-2,3,4-tri-O-acetyl-6-deoxy-α-L-mannopyranosyl-(1→4)-O-2,3,6-tri-O-acetyl-β-D-glucopyranosyl-(1→6)-2,3,4-tri-O-acetyl-β-D-glucopyranosyl) ester;

28-(acetyloxy)lup-20(29)-en-3-yl-4-O-(2,3,4,6-tetra-O-acetyl-α-D-glucopyranosyl)-β-D-glucopyranoside triacetate;

3β-28-(acetyloxy)lup-20(29)-en-3-yl-4-O-(2,3,4,6-tetra-O-acetyl-β-D-glucopyranosyl)-β-D-glucopyranoside triacetate;

3β-3-(acetyloxy)lup-20(29)-en-28-yl-4-O-(2,3,4,6-tetra-O-acetyl-α-D-glucopyranosyl)-β-D-glucopyranoside triacetate;

3β-3-((2,3,4,6-tetra-O-acetyl-β-D-glucopyranosyl)oxy)lup-20(29)-en-28-yl-β-D-glucopyranoside tetraacetate;

3β-28-(acetyloxy)lup-20(29)-en-3-yl-β-D-glucopyranoside tetraacetate;

3β-3-(acetyloxy)lup-20(29)-en-28-yl-β-D-glucopyranoside tetraacetate;

3β-lup-20(29)-en-3-yl-β-D-glucopyranoside tetraacetate;

3β-lup-20(29)-en-3-yl-6-deoxy-α-L-mannopyranoside;

3β-3-((6-deoxy-2-O-β-D-glucopyranosyl-α-L-mannopyranosyl)oxy)lup-20(29)-en-28-oic acid;

3β-3-((6-deoxy-α-L-mannopyranosyl)oxy)lup-20(29)-en-28-oic acid;

3β-lup-20(29)-en-3-yl-4-O-β-D-xylopyranosyl-β-D-glucopyranoside;

3β-28-(acetyloxy)lup-20(29)-en-3-yl-α-D-glucopyranoside tetraacetate;

3β-3-hydroxylup-20(29)-en-28-yl-β-D-glucopyranoside 2,3,4,6-tetraacetate;

3β-28-((6-O-D-apio-β-D-furanosyl-β-D-glucopyranosyl)oxy)-28-oxolup-20(29)-en-3-yl-4-O-β-D-galactopyranosyl-β-D-glucopyranosiduronic acid;

3β-3-((2-propenyl)oxy)lup-20(29)-en-28-oic acid ("3-O-allylbetulinic acid");

3β-3,28-dimethoxylup-20(29)-ene ("3,28-di-O-methylbetulin");

3β-3,28-dimethoxylupane ("3,28-di-O-methyldihydrobetulin");

3β-28-methoxylupan-3-ol ("28-methyldihydrobetulin");

3β-3-methoxylup-20(29)-en-28-oic acid ("3-O-methylbetulinic acid");

3β-3-methoxylup-20(29)-en-28-oic acid methyl ester ("methyl 3-O-methylbetulinate");

8ξ-2,6-anhydro-9-O-((3β,18β)-17-carboxy-28-norlupan-3-yl)-1,7,8-trideoxy-8-methyl-3,4,5-tris-O-(phenylmethyl)-L-glycero-D-galactononitol;

2,6-anhydro-9-O-((3β,18β)-17-carboxy-28-norlup-20(29)-en-3-yl)-1,7,8-trideoxy-8-methylene-3,4,5-tris-O-(phenylmethyl)-L-glycero-D-galactononitol;

3α-3-methoxylup-20(29)-en-28-oic acid; or

3α-3-methoxylup-20(29)-en-28-oic acid methyl ester.

Preferably, the compound of formula I is:

3β-28-(acetyloxy)lup-20(29)-en-3-yl-β-D-glucopyranoside ("28-acetyl-3-β-D-glucosylbetulin");

3β-28-(acetyloxy)lup-20(29)-en-3-yl-β-D-galactopyranoside ("28-acetyl-3-β-D-galactosylbetulin"); or 3β-3-(acetyloxy)lup-20(29)-en-28-yl-β-D-glucopyranoside ("3-acetyl-28-β-D-glucosylbetulin").

The present invention further provides compositions, useful for the treatment of neuroectodermal tumors comprising a therapeutically effective amount of compound of formula (I), or a pharmaceutically acceptable salt thereof, with the proviso that the compound of formula (I) is not:

3β-3-hydroxylup-20(29)-en-28-oic acid ("betulinic acid");

3β-lup-20(29)-ene-3,28-diol ("betulin");

3β-lup-20(29)-ene-3,28-diol diacetate ("3,28-diacetylbetulin");

3β-3-(acetyloxy)lup-20(29)-en-28-oic acid ("3-acetylbetulinic acid");

3β-3-(1-oxobutoxy)lup-20(29)-en-28-oic acid ("3-butyrylbetulinic acid");

3β-3-(2,3-dihydroxycinnamoyl)lup-20(29)-en-28-oic acid ("3-(2,3-dihydroxycinnamoyl)betulinic acid");

3β-lup-20(29)-ene-3,28-diol 3-acetate ("3-acetylbetulin");

3β-lup-20(29)-ene-3,28-diol 28-acetate ("28-acetylbetulin");

3β-3-hydroxylup-20(29)-en-28-oic acid methyl ester ("methyl betulinate");

3β-3-(acetyloxy)lup-20(29)-en-28-oic acid methyl ester ("methyl 3-acetylbetulinate");

3β-3-hydroxylup-20(29)-en-28-oic acid ethyl ester ("ethyl betulinate");

3β-3-hydroxylup-20(29)-en-28-oic acid butyl ester ("butyl betulinate");

3β-lupane-3,28-diol ("dihydrobetulin");

3β-3-hydroxylupan-28-oic acid ("dihydrobetulinic acid");

3β-3-hydroxylupan-28-oic acid methyl ester ("methyl dihydrobetulinate");

3β-3-(acetyloxy)lupan-28-oic acid methyl ester ("methyl 3-acetyldihydrobetulinate");

3β-3-(acetyloxy)-lupan-28-oic acid ("3-acetyldihydrobetulinic acid");

3β-lupane-3,28-diol diacetate ("3,28-diacetyldihydrobetulin");

3β-lupane-3,28-diol dibutanoate ("3,28-dibutyryldihydrobetulin");

3β-3-(3-methyl-1-oxobutoxy)lupan-28-oic acid ("3-(3-methylbutryryl)dihydrobetulinic acid");

3β-3-((1-oxo-2-butenyl)oxy)lup-20(29)-en-28-oic acid ("3-(trans-2-butenyl)betulinic acid");

3β-3-(2,2-dimethyl-1-oxopropoxy)lupan-28-oic acid ("3-(2,2-dimethylpropionyl)dihydrobetulinic acid");

3α-28-hydroxylup-20(29)-en-3-yl-6-O-(6-deoxy-α-L-mannopyranosyl)-β-D-glucopyranoside;

3α-28-hydroxylup-20(29)-en-3-yl-β-D-glucopyranoside;

3α,4α-3-(β-D-glucopyranosyloxy)lup-20(29)-en-28-oic acid;

3-(β-D-glucopyranosyloxy)lup-20(29)-en-28-oic acid;

3β-28-hydroxylup-20(29)-en-3-yl-β-D-glucopyranoside;

3β-3-hydroxylup-20(29)-en-28-yl-β-D-glucopyranoside;

3β-28(acetyloxy)lup-20(29)-en-3-yl-2-deoxy-α-D-arabinohexopyranoside triacetate;

3β-28(acetyloxy)lup-20(29)-en-3-yl-2-deoxy-β-L-arabinohexopyranoside triacetate;

3β-28(acetyloxy)lup-20(29)-en-3-yl-2,6-dideoxy-β-L-arabinohexopyranoside diacetate;

3β-3-(acetyloxy)lup-20(29)-en-28-yl-2-deoxy-α-D-arabinohexopyranoside triacetate;

3β-3-(acetyloxy)lup-20(29)-en-28-yl-2,6-dideoxy-β-L-arabinohexopyranoside diacetate;

3β-28-hydroxylup-20(29)-en-3-yl-2-deoxy-α-D-arabinohexopyranoside;

3β-28-hydroxylup-20(29)-en-3-yl-2-deoxy-β-L-arabinohexopyranoside;

3β-28-hydroxylup-20(29)-en-3-yl-2,6-dideoxy-β-L-arabinohexopyranoside;

3β-3-hydroxylup-20(29)-en-28-yl-2-deoxy-α-D-arabinohexopyranoside;

3β-lup-20(29)-en-3,28-diyl-bis-β-D-glucopyranoside;

3β-lup-20(29)-en-3,28-diyl-bis-4-O-α-D-glucopyranosyl-β-D-glucopyranoside;

3β-lup-20(29)-en-3,28-diyl-bis-(4-O-(2,3,4,6-tetra-O-acetyl-α-D-glucopyranosyl)-β-D-glucopyranoside hexaacetate;

3β-3-((4-O-α-D-glucopyranosyl-β-D-glucopyranosyl)oxy)lup-20(29)-en-28-oic acid;

3β-3-((6-O-β-D-glucopyranosyl-β-D-glucopyranosyl)oxy)lup-20(29)-en-28-oic acid;

3β-3-hydroxylup-20(29)-en-28-yl-2,6-dideoxy-β-L-arabinohexopyranoside;

3β-3-((2-O-α-L-arabinopyranosyl-6-deoxy-β-D-glucopyranosyl)oxy)lup-20(29)-en-28-oic acid;

3β-3-((2-O-β-D-glucopyranosyl-β-D-glucopyranosyl)oxy)lup-20(29)-en-28-oic acid;

3β-3-hydroxylup-20(29)-en-28-oic acid 2,3,4,6-tetra-O-acetyl-β-D-glucopyranosyl ester;

3β-3-hydroxylup-20(29)-en-28-oic acid β-D-galactopyranosyl ester;

3β-3-hydroxylup-20(29)-en-28-oic acid 4-O-β-D-galactopyranosyl-β-D-glucopyranosyl ester;

3β-3-((2,3,4,6-tetra-O-acetyl-β-D-glucopyranosyl)oxy)lup-20(29)-en-28-oic acid methyl ester;

3β-3-(acetyloxy)lup-20(29)-en-28-oic acid 2,3,4,6-tetra-O-acetyl-β-D-glucopyranosyl ester;

3β-3-(acetyloxy)lup-20(29)-en-28-oic acid β-D-glucopyranosyl ester;

3β-3-((2,3,4,6-tetra-O-acetyl-β-D-glucopyranosyl)oxy)lup-20(29)-en-28-oic acid 2,3,4,6-tetra-O-acetyl-β-D-glucopyranosyl ester;

3β-3-((2,3,4,6-tetra-O-acetyl-β-D-glucopyranosyl)oxy)lupan-28-oic acid methyl ester;

3β-3-(acetyloxy)lupan-28-oic acid 2,3,4,6-tetra-O-acetyl-β-D-glucopyranosyl ester;

3α-3-((2,3,4,6-tetra-O-acetyl-β-D-glucopyranosyl)oxy)lup-20(29)-en-28-oic acid;

3β-3-((2,3,4,6-tetra-O-acetyl-β-D-glucopyranosyl)oxy)lup-20(29)-en-28-oic acid;

3β-3-(acetyloxy)lupan-28-oic acid β-D-glucopyranosyl ester;

3β-3-hydroxylup-20(29)-en-28-oic acid β-D-glucopyranosyl ester;

3β-3-hydroxylup-20(29)-en-28-oic acid β-D-xylopyranosyl ester;

3β-hydroxylup-20(29)-en-28-oic acid β-D-glucopyranosyl ester 2′,3′,4′,6′-tetrabenzoate;

3β-lup-20(29)-en-28-oic acid (β-D-glucopyranosyloxy)-β-D-glucopyranosyl ester octabenzoate;

3β-lup-20(29)-en-28-oic acid (α-L-arabinopyranosyloxy)-α-L-arabinopyranosyl ester;

3β-lup-20(29)-en-28-oic acid (α-L-arabinopyranosyloxy)-α-L-arabinopyranosyl ester hexabenzoate;

3β-3-(β-D-glucopyranosyloxy)lup-20(29)-en-28-oic acid methyl ester;

3β-3-(β-D-glucopyranosyloxy)lupan-28-oic acid methyl ester;

3β-3-hydroxylupan-28-oic acid β-D-glucopyranosyl ester;

3β-17-carboxy-28-norlup-20(29)-en-3-yl-3-O-β-D-xylopyranosyl-β-D-glucopyranosiduronic acid;

3β-17-carboxy-28-norlup-20(29)-en-3-yl-2-O-β-D-xylopyranosyl-β-D-glucopyranosiduronic acid;

3β-3-(β-D-glucopyranosyloxy)lup-20(29)-en-28-oic acid 6-O-β-D-glucopyranosyl-β-D-glucopyranosyl ester;

3α-3-hydroxylup-20(29)-en-28-oic acid O-6-deoxy-α-L-mannopyranosyl-(1→4)-O-β-D-glucopyranosyl-(1→6)-O-β-D-glucopyranosyl ester;

3α-3-(β-D-glucopyranosyloxy)lup-20(29)-en-28-oic acid O-6-deoxy-α-L-mannopyranosyl-(1→4)-O-β-D-glucopyranosyl-(1→6)-O-β-D-glucopyranosyl ester;

3β-3-(β-D-glucopyranosyloxy)lup-20(29)-en-28-oic acid O-6-deoxy-α-L-mannopyranosyl-(1→4)-O-β-D-glucopyranosyl-(1→6)-O-β-D-glucopyranosyl ester;

3β-28-methoxy-28-oxolup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid methyl ester diacetate;

3β-17-carboxy-28-norlup-20(29)-en-3-yl-O-6-deoxy-α-L-mannopyranosyl-(1→2)-O-β-D-glucopyranosyl-(1→2)-β-D-glucopyranosiduronic acid;

3β-17-carboxy-28-norlup-20(29)-en-3-yl-O-6-deoxy-α-L-mannopyranosyl-(1→2)-O-β-D-xylopyranosyl-(1→2)-β-D-glucopyranosiduronic acid;

3β-17-carboxy-28-norlup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid diacetate;

3β-17-carboxy-28-norlup-20(29)-en-3-yl-O-2,3,4-tri-O-acetyl-6-deoxy-α-L-mannopyranosyl-(1→2)-O-3,4-di-O-acetyl-β-D-xylopyranosyl-(1→2)-β-D-glucopyranosiduronic acid diacetate;

3β-28-methoxy-28-oxolup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid methyl ester diacetate;

3β-28-methoxy-28-oxolup-20(29)-en-3-yl-O-2,3,4-tri-O-acetyl-6-deoxy-α-L-mannopyranosyl-(1→2)-O-3,4-di-O-acetyl-β-D-xylopyranosyl-(1→2)-β-D-glucopyranosiduronic acid methyl ester diacetate;

3β-3-((O-α-L-arabinofuranosyl-(1→2)-O-6-deoxy-α-L-mannopyranosyl-(1→4)-β-D-glucopyranosyl)oxy)-lup-20(29)-en-28-oic acid;

3β-3-((O-α-L-arabinofuranosyl-(1→2)-O-6-deoxy-α-L-mannopyranosyl-(1→4)-β-D-glucopyranosyl)oxy)-lup-20(29)-en-28-oic acid methyl ester;

3β-28-hydroxylup-20(29)-en-3-yl-4-O-β-D-glucopyranosyl-β-D-glucopyranoside;

3β-28-hydroxylup-20(29)-en-3-yl-4-O-α-D-glucopyranosyl-β-D-glucopyranoside;

3β-3-hydroxylup-20(29)-en-28-yl-4-O-α-D-glucopyranosyl-β-D-glucopyranoside;

3β-28-hydroxylup-20(29)-en-3-yl-β-D-xylopyranoside;

3-(β-D-glucopyranosyloxy)lup-20(29)-en-28-oic acid O-6-deoxy-α-L-mannopyranosyl-(1→4)-O-β-D-glucopyranosyl-(1→6)-O-β-D-glucopyranosyl ester;

3α-lup-20(29)-en-28-oic acid 3-(β-D-glucopyranosyloxy)-O-6-deoxy-α-L-mannopyranosyl-(1→4)-O-β-D-glucopyranosyl-(1→6)-O-β-D-glucopyranosyl ester;

3α,4α-3-(β-D-glucopyranosyloxy)lup-20(29)-en-28-oic acid;

3α-lup-20(29)-en-28-oic acid 3-((O-6-acetyl-β-D-glucopyranosyl)oxy)-O-6-deoxy-α-L-mannopyranosyl-(1→4)-O-β-D-glucopyranosyl-(1→6)-O-β-D-glucopyranosyl ester;

3β-28-hydroxylup-20(29)-en-3-yl-O-α-D-glucopyranosyl-(1→4)-O-α-D-glucopyranosyl-(1→4)-O-β-D-glucopyranosyl-(1→4)-β-D-glucopyranoside;

3α-3-(sulfooxy)lup-20(29)-en-28-oic acid 28-O-6-deoxy-α-L-mannopyranosyl-(1→4)-O-β-D-glucopyranosyl-(1→6)-β-D-glucopyranosyl ester;

3-(sulfooxy)lup-20(29)-en-28-oic acid 28-(O-2,3,4-tri-O-acetyl-6-deoxy-α-L-mannopyranosyl-(1→4)-O-2,3,6-tri-O-acetyl-β-D-glucopyranosyl-(1→6)-2,3,4-tri-O-acetyl-β-D-glucopyranosyl) ester;

3α-3-(acetyloxy)lup-20(29)-en-28-oic acid O-2,3,4-tri-O-acetyl-6-deoxy-α-L-mannopyranosyl-(1→4)-O-2,3,6-tri-O-acetyl-β-D-glucopyranosyl-(1→6)-2,3,4-tri-O-acetyl-β-D-glucopyranosyl) ester;

28-(acetyloxy)lup-20(29)-en-3-yl-4-O-(2,3,4,6-tetra-O-acetyl-α-D-glucopyranosyl)-β-D-glucopyranoside triacetate;

3β-28-(acetyloxy)lup-20(29)-en-3-yl-4-O-(2,3,4,6-tetra-O-acetyl-β-D-glucopyranosyl)-β-D-glucopyranoside triacetate;

3β-3-(acetyloxy)lup-20(29)-en-28-yl-4-O-(2,3,4,6-tetra-O-acetyl-α-D-glucopyranosyl)-β-D-glucopyranoside triacetate;

3β-3-((2,3,4,6-tetra-O-acetyl-β-D-glucopyranosyl)oxy)lup-20(29)-en-28-yl-β-D-glucopyranoside tetraacetate;

3β-28-(acetyloxy)lup-20(29)-en-3-yl-β-D-glucopyranoside tetraacetate;

3β-3-(acetyloxy)lup-20(29)-en-28-yl-β-D-glucopyranoside tetraacetate;

3β-lup-20(29)-en-3-yl-β-D-glucopyranoside tetraacetate;

3β-lup-20(29)-en-3-yl-6-deoxy-α-L-mannopyranoside;

3β-3-((6-deoxy-2-O-β-D-glucopyranosyl-α-L-mannopyranosyl)oxy)lup-20(29)-en-28-oic acid;

3β-3-((6-deoxy-α-L-mannopyranosyl)oxy)lup-20(29)-en-28-oic acid;

3β-lup-20(29)-en-3-yl-4-O-β-D-xylopyranosyl-β-D-glucopyranoside;

3β-28-(acetyloxy)lup-20(29)-en-3-yl-α-D-glucopyranoside tetraacetate;

3β-3-hydroxylup-20(29)-en-28-yl-β-D-glucopyranoside 2,3,4,6-tetraacetate;

3β-28-((6-O-D-apio-β-D-furanosyl-β-D-glucopyranosyl)oxy)-28-oxolup-20(29)-en-3-yl-4-O-β-D-galactopyranosyl-β-D-glucopyranosiduronic acid;

3β-3-((2-propenyl)oxy)lup-20(29)-en-28-oic acid ("3-O-allylbetulinic acid");

3β-3,28-dimethoxylup-20(29)-ene ("3,28-di-O-methylbetulin");

3β-3,28-dimethoxylupane ("3,28-di-O-methyldihydrobetulin");

3β-28-methoxylupan-3-ol ("28-methyldihydrobetulin");

3β-3-methoxylup-20(29)-en-28-oic acid ("3-O-methylbetulinic acid");

3β-3-methoxylup-20(29)-en-28-oic acid methyl ester ("methyl 3-O-methylbetulinate");

8ξ-2,6-anhydro-9-O-((3β,18β)-17-carboxy-28-norlupan-3-yl)-1,7,8-trideoxy-8-methyl-3,4,5-tris-O-(phenylmethyl)-L-glycero-D-galactononitol;

2,6-anhydro-9-O-((3β,18β)-17-carboxy-28-norlup-20(29)-en-3-yl)-1,7,8-trideoxy-8-methylene-3,4,5-tris-O-(phenylmethyl)-L-glycero-D-galactononitol;

3α-3-methoxylup-20(29)-en-28-oic acid; or

3α-3-methoxylup-20(29)-en-28-oic acid methyl ester.

Preferably, the compositions of the present invention comprise a compound of formula (I) selected from the group consisting of:

3β-28-(acetyloxy)lup-20(29)-en-3-yl-β-D-glucopyranoside ("28-acetyl-3-β-D-glucosylbetulin");

3β-28-(acetyloxy)lup-20(29)-en-3-yl-β-D-galactopyranoside ("28-acetyl-3-β-D-galactosylbetulin"); and 3β-3-(acetyloxy)lup-20(29)-en-28-yl-β-D-glucopyranoside ("3-acetyl-28-β-D-glucosylbetulin");

a D-enantiomer, L-enantiomer or racemate thereof, or a pharmaceutically acceptable salt thereof.

Such compositions can also comprise a pharmaceutically acceptable carrier or vehicle.

The invention further provides methods for the treatment of neuroectodermal tumors, comprising administering to a patient in need of such treatment a therapeutically effective amount of a compound of formula (I):

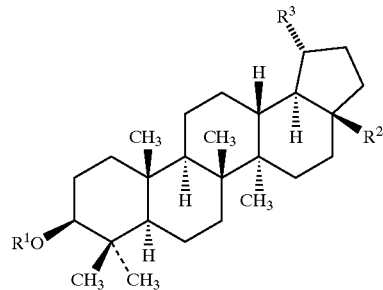

wherein $R^1$ is selected from the group consisting of hydrogen, —$SO_3H$, —$PO_3H_2$, —$C_1$–$C_{20}$ straight or branched chain alkyl, —$C_2$–$C_{20}$ straight or branched chain alkenyl, —$C_2$–$C_{20}$ straight or branched chain alkynyl, —$(CH_2CH_2O)_nH$, —$(CH_2CH_2O)_nCH_3$, —$(CH_2CH_2O)_nCH_2CH_3$, —$C(O)C_6H_5$, —$C(O)$ $C_1$–$C_{20}$ straight or branched chain alkyl, —$C(O)$ $C_2$–$C_{20}$ straight or branched chain alkenyl, —$C(O)$ $C_2$–$C_{20}$ straight or branched chain alkynyl, myo-inosityl, scyllo-inosityl, a cyclitol, conduritol A, quebrachitol, a monosaccharide, a disaccharide and an oligosaccharide; the —$(CH_2CH_2O)_nH$, myo-inosityl, scyllo-inosityl, cyclitol, conduritol A, quebrachitol, monosaccharide, disaccharide and oligosaccharide being optionally substituted with one or more —$C(O)$ $C_1$–$C_{20}$ straight or branched chain alkyl, —$C(O)$ $C_2$–$C_{20}$ straight or branched chain alkenyl, —$C(O)$ $C_2$–$C_{20}$ straight or branched chain alkynyl, sulfate, or mono-, di- or tri-phosphate groups;

$R^2$ is selected from the group consisting of —$CO_2H$, —$CO_2(C_6H_5)$, —$CO_2(C_1$–$C_{20}$ straight or branched chain alkyl), —$CO_2(C_2$–$C_{20}$ straight or branched chain alkenyl), —$CO_2(C_2$–$C_{20}$ straight or branched chain alkynyl), —$CO_2$(myo-inosityl), —$CO_2$(scyllo-inosityl), —$CO_2$(cyclitol), —$CO_2$(conduritol A), —$CO_2$(quebrachitol), —$CO_2$(monosaccharide), —$CO_2$(disaccharide), —$CO_2$(oligosaccharide), —$CO(OCH_2CH_2)_nOH$, —$CO(OCH_2CH_2)_nOCH_3$, —$CO(OCH_2CH_2)_nOCH_2CH_3$, —$CH_2OH$, —$CH_2OSO_3H$, —$CH_2OPO_3H_2$, —$CH_2O(C_6H_5)$, —$CH_2O(C_1$–$C_{20}$ straight or branched chain alkyl), —$CH_2O(C_2$–$C_{20}$ straight or branched chain alkenyl), —$CH_2O(C_2$–$C_{20}$ straight or branched chain alkynyl), —$CH_2O_2C$ $(C_1$–$C_{20}$ straight or branched chain alkyl), —$CH_2O_2C$ $(C_2$–$C_{20}$ straight or branched chain alkenyl), —$CH_2O_2C(C_2$–$C_{20}$ straight or branched chain alkynyl), —$CH_2O$(myo-inosityl), —$CH_2O$(scyllo-inosityl), —$CH_2O$(cyclitol), —$CH_2O$(conduritol A), —$CH_2O$(quebrachitol), —$CH_2O$(monosaccharide), —$CH_2O$(disaccharide), —$CH_2O$(oligosaccharide), —$CH_2(OCH_2CH_2)_nOH$, —$CH_2(OCH_2CH_2)_nOCH_3$, —$CH_2(OCH_2CH_2)_nOCH_2CH_3$, —$CH_2O_2C$ $(OCH_2CH_2)_nOH$, —$CH_2O_2C(OCH_2CH_2)_nOCH_3$, and —$CH_2O_2C(OCH_2CH_2)_nOCH_2CH_3$; the myo-inosityl, scyllo-inosityl, cyclitol, conduritol A, quebrachitol, monosaccharide, disaccharide, oligosaccharide, —$CH_2(OCH_2CH_2)_nOH$ and —$CH_2O_2C(OCH_2CH_2)_nOH$ being optionally substituted with one or more —$C(O)$ $C_1$–$C_{20}$ straight or branched chain alkyl, —$C(O)$ $C_2$–$C_{20}$ straight or branched chain alkenyl, —$C(O)$ $C_2$–$C_{20}$ straight or branched chain alkynyl, sulfate, or mono-, di- or tri-phosphate groups;

R² is selected from the group consisting of —CO₂H, —CO₂(C₆H₅), —CO₂(C₁-C₂₀ straight or branched chain alkyl), —CO₂(C₂-C₂₀ straight or branched chain alkenyl), —CO₂(C₂-C₂₀ straight or branced chain alkynyl), —CO₂(myo-inosityl), —CO₂(scyllo-inosityl), —CO₂(cyclitol), —CO₂(conduritol A), —CO₂(quebrachitol), —CO₂(monosaccharide), —CO₂(disaccharide), —CO₂(oligosaccharide), —CO(OCH₂CH₂)$_n$OH, —CO(OCH₂CH₂)$_n$OCH₃, —CO(OCH₂CH₂)$_n$OCH₂CH₃, —CH₂OH, —CH₂OSO₃H, —CH₂OPO₃H₂, —CH₂O(C₆H₅), —CH₂O(C₁-C₂₀ straight or branched chain alkyl), —CH₂O(C₂-C₂₀ straight or branched chain alkenyl), —CH₂O(C₂-C₂₀ straight or branched chain alkynyl), —CH₂O₂C(C₁-C₂₀ straight or branched chain alkyl), —OH₂O₂C(C₂-C₂₀ straight or branched chain alkenyl), —CH₂O₂C(C₂-C₂₀ straight or branched chain alkynyl), —CH₂O(myo-inosityl), —CH₂O(scyllo-inosityl), —CH₂O(cyclitol), —CH₂O(conduritol A), —CH₂O(quebrachitol), —CH₂O(monosaccharide), —CH₂O(disaccharide), —CH₂O(oligosaccharide), —CH₂(OCH₂$_{CH2}$)$_n$OH, —CH₂(OCH₂CH₂)$_n$OCH₃, —CH₂(OCH₂CH₂)$_n$OCH₂CH₃, —CH₂O₂C(OCH₂CH₂)$_n$OH, —CH₂O₂C(OCH₂CH₂)$_n$OCH₃, and —CH₂O₂C(OCH₂CH₂)$_n$OCH₂CH₃; the myo-inosityl, scyllo-inosityl, cyclitol, conduritol A, quebrachitol, monosaccharide, disaccharide, oligosaccharide, —CH₂(OCH₂CH₂)$_n$OH and —CH₂O₂C(OCH₂CH₂)$_n$OH being optionally substituted with one or more =13 C(O)C₁-C₂₀ straight or branched chain alkyl, —C(O)C₂-C₂₀ straight or branched chain alkenyl, —C(O)C₂-C₂₀ straight or branched chain alkynyl, sulfate, or mono-, di- or tri-phosphate groups;

R³ is selected from the group consisting of —C(CH₃)(=CH₂) and —CH(CH₃)₂;

each n is independently an integer from 1 to 20;

a D-enantiomer, L-enantiomer, or racemate thereof;

or a pharmaceutically acceptable salt thereof.

In a preferred embodiment, the present methods comprise administering to a patient a compound of formula (I) selected from the group consisting of:

3β-3-hydroxylup-20(29)-en-28-oic acid ("betulinic acid");
3β-lup-20(29)-ene-3,28-diol ("betulin");
3β-lup-20(29)-ene-3,28-diol diacetate ("3,28-diacetylbetulin");
3β-3-(acetyloxy)lup-20(29)-en-28-oic acid ("3-acetylbetulinic acid");
3β-3-(1-oxobutoxy)lup-20(29)-en-28-oic acid ("3-butyrylbetulinic acid");
3β-3-(2,3-dihydroxycinnamoyl)lup-20(29)-en-28-oic acid ("3-(2,3-dihydroxycinnamoyl)betulinic acid");
3β-lup-20(29)-ene-3,28-diol 3-acetate ("3-acetylbetulin");
3β-lup-20(29)-ene-3,28-diol 28-acetate ("28-acetylbetulin");
3β-3-hydroxylup-20(29)-en-28-oic acid methyl ester ("methyl betulinate");
3β-3-(acetyloxy)lup-20(29)-en-28-oic acid methyl ester ("methyl 3-acetylbetulinate");
3β-3-hydroxylup-20(29)-en-28-oic acid ethyl ester ("ethyl betulinate");
3β-3-hydroxylup-20(29)-en-28-oic acid butyl ester ("butyl betulinate");
3β-lupane-3,28-diol ("dihydrobetulin");
3β-3-hydroxylupan-28-oic acid ("dihydrobetulinic acid");
3β-3-hydroxylupan-28-oic acid methyl ester ("methyl dihydrobetulinate");
3β-3-(acetyloxy)lupan-28-oic acid methyl ester ("methyl 3-acetyldihydrobetulinate");
3β-3-(acetyloxy)-lupan-28-oic acid ("3-acetyldihydrobetulinic acid");
3β-lupane-3,28-diol diacetate ("3,28-diacetyldihydrobetulin");
3β-lupane-3,28-diol dibutanoate ("3,28-dibutyryldihydrobetulin");
3β-3-(3-methyl-1-oxobutoxy)lupan-28-oic acid ("3-(3-methylbutryryl)dihydrobetulinic acid");
3β-3-((1-oxo-2-butenyl)oxy)lup-20(29)-en-28-oic acid ("3-(trans-2-butenyl)betulinic acid");
3β-3-(2,2-dimethyl-1-oxopropoxy)lupan-28-oic acid ("3-(2,2-dimethylpropionyl)dihydrobetulinic acid");
3α-28-hydroxylup-20(29)-en-3-yl-6-O-(6-deoxy-α-L-mannopyranosyl)-β-D-glucopyranoside;
3α-28-hydroxylup-20(29)-en-3-yl-β-D-glucopyranoside;
3α,4α-3-(β-D-glucopyranosyloxy)lup-20(29)-en-28-oic acid;
3-(β-D-glucopyranosyloxy)lup-20(29)-en-28-oic acid;
3β-28-hydroxylup-20(29)-en-3-yl-β-D-glucopyranoside;
3β-3-hydroxylup-20(29)-en-28-yl-β-D-glucopyranoside;
3β-28(acetyloxy)lup-20(29)-en-3-yl-2-deoxy-α-D-arabinohexopyranoside triacetate;
3β-28(acetyloxy)lup-20(29)-en-3-yl-2-deoxy-β-L-arabinohexopyranoside triacetate;
3β-28(acetyloxy)lup-20(29)-en-3-yl-2,6-dideoxy-β-L-arabinohexopyranoside diacetate;
3β-3-(acetyloxy)lup-20(29)-en-28-yl-2-deoxy-α-D-arabinohexopyranoside triacetate;
3β-3-(acetyloxy)lup-20(29)-en-28-yl-2,6-dideoxy-β-L-arabinohexopyranoside diacetate;
3β-28-hydroxylup-20(29)-en-3-yl-2-deoxy-α-D-arabinohexopyranoside;
3β-28-hydroxylup-20(29)-en-3-yl-2-deoxy-β-L-arabinohexopyranoside;
3β-28-hydroxylup-20(29)-en-3-yl-2,6-dideoxy-β-L-arabinohexopyranoside;
3β-3-hydroxylup-20(29)-en-28-yl-2-deoxy-α-D-arabinohexopyranoside;
3β-lup-20(29)-en-3,28-diyl-bis-β-D-glucopyranoside;
3β-lup-20(29)-en-3,28-diyl-bis-4-O-α-D-glucopyranosyl-β-D-glucopyranoside;
3β-lup-20(29)-en-3,28-diyl-bis-(4-O-(2,3,4,6-tetra-O-acetyl-α-D-glucopyranosyl)-β-D-glucopyranoside hexaacetate;
3β-3-((4-O-α-D-glucopyranosyl-β-D-glucopyranosyl)oxy)lup-20(29)-en-28-oic acid;
3β-3-((6-O-β-D-glucopyranosyl-β-D-glucopyranosyl)oxy)lup-20(29)-en-28-oic acid;
3β-3-hydroxylup-20(29)-en-28-yl-2,6-dideoxy-β-L-arabinohexopyranoside;
3β-3-((2-O-α-L-arabinopyranosyl-6-deoxy-β-D-glucopyranosyl)oxy)lup-20(29)-en-28-oic acid;
3β-3-((2-O-β-D-glucopyranosyl-β-D-glucopyranosyl)oxy)lup-20(29)-en-28-oic acid;
3β-3-hydroxylup-20(29)-en-28-oic acid 2,3,4,6-tetra-O-acetyl-β-D-glucopyranosyl ester;
3β-3-hydroxylup-20(29)-en-28-oic acid β-D-galactopyranosyl ester;
3β-3-hydroxylup-20(29)-en-28-oic acid 4-O-β-D-galactopyranosyl-β-D-glucopyranosyl ester;
3β-3-((2,3,4,6-tetra-O-acetyl-β-D-glucopyranosyl)oxy)lup-20(29)-en-28-oic acid methyl ester;
3β-3-(acetyloxy)lup-20(29)-en-28-oic acid 2,3,4,6-tetra-O-acetyl-β-D-glucopyranosyl ester;
3β-3-(acetyloxy)lup-20(29)-en-28-oic acid β-D-glucopyranosyl ester,
3β-3-((2,3,4,6-tetra-O-acetyl-β-D-glucopyranosyl)oxy)lup-20(29)-en-28-oic acid 3,4,6-tetra-O-acetyl-β-D-glucopyranosyl ester;

3β-3-((2,3,4,6-tetra-O-acetyl-β-D-glucopyranosyl)oxy) lupan-28-oic acid methyl ester;

3β-3-(acetyloxy)lupan-28-oic acid 2,3,4,6-tetra-O-acetyl-β-D-glucopyranosyl ester;

3α-3-((2,3,4,6-tetra-O-acetyl-β-D-glucopyranosyl)oxy)lup-20(29)-en-28-oic acid;

3β-3-((2,3,4,6-tetra-O-acetyl-β-D-glucopyranosyl)oxy)lup-20(29)-en-28-oic acid;

3β-3-(acetyloxy)lupan-28-oic acid β-D-glucopyranosyl ester,

3β-3-hydroxylup-20(29)-en-28-oic acid β-D-glucopyranosyl ester;

3β-3-hydroxylup-20(29)-en-28-oic acid β-D-xylopyranosyl ester;

3β-hydroxylup-20(29)-en-28-oic acid β-D-glucopyranosyl ester 2',3',4',6'-tetrabenzoate;

3β-lup-20(29)-en-28-oic acid (β-D-glucopyranosyloxy)-β-D-glucopyranosyl ester octabenzoate;

3β-lup-20(29)-en-28-oic acid (α-L-arabinopyranosyloxy)-α-L-arabinopyranosyl ester;

3β-lup-20(29)-en-28-oic acid (α-L-arabinopyranosyloxy)-α-L-arabinopyranosyl ester hexabenzoate;

3β-3-(β-D-glucopyranosyloxy)lup-20(29)-en-28-oic acid methyl ester;

3β-3-(β-D-glucopyranosyloxy)lupan-28-oic acid methyl ester;

3β-3-hydroxylupan-28-oic acid β-D-glucopyranosyl ester;

3β-17-carboxy-28-norlup-20(29)-en-3-yl-3-O-β-D-xylopyranosyl-β-D-glucopyranosiduronic acid;

3β-17-carboxy-28-norlup-20(29)-en-3-yl-2-O-β-D-xylopyranosyl-β-D-glucopyranosiduronic acid;

3β-3-(β-D-glucopyranosyloxy)lup-20(29)-en-28-oic acid 6-O-β-D-glucopyranosyl-β-D-glucopyranosyl ester;

3α-3-hydroxylup-20(29)-en-28-oic acid O-6-deoxy-α-L-mannopyranosyl-(1→4)-O-β-D-glucopyranosyl-(1→6)-O-β-D-glucopyranosyl ester;

3α-3-(β-D-glucopyranosyloxy)lup-20(29)-en-28-oic acid O-6-deoxy-α-L-mannopyranosyl-(1→4)-O-β-D-glucopyranosyl-(1→6)-O-β-D-glucopyranosyl ester;

3β-3-(β-D-glucopyranosyloxy)lup-20(29)-en-28-oic acid O-6-deoxy-α-L-mannopyranosyl-(1→4)-O-β-D-glucopyranosyl-(1→6)-O-β-D-glucopyranosyl ester;

3β-28-methoxy-28-oxolup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid methyl ester diacetate;

3β-17-carboxy-28-norlup-20(29)-en-3-yl-O-6-deoxy-α-L-mannopyranosyl-(1→2)-O-β-D-glucopyranosyl-(1→2)-β-D-glucopyranosiduronic acid;

3β-17-carboxy-28-norlup-20(29)-en-3-yl-O-6-deoxy-α-L-mannopyranosyl-(1→2)-O-β-D-xylopyranosyl-(1→2)-β-D-glucopyranosiduronic acid;

3β-17-carboxy-28-norlup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid diacetate;

3β-17-carboxy-28-norlup-20(29)-en-3-yl-O-2,3,4-tri-O-acetyl-6-deoxy-α-L-mannopyranosyl-(1→2)-O-3,4-di-O-acetyl-β-D-xylopyranosyl-(1→2)-β-D-glucopyranosiduronic acid diacetate;

3β-28-methoxy-28-oxolup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid methyl ester diacetate;

3β-28-methoxy-28-oxolup-20(29)-en-3-yl-O-2,3,4-tri-O-acetyl-6-deoxy-α-L-mannopyranosyl-(1→2)-O-3,4-di-O-acetyl-β-D-xylopyranosyl-(1→2)-β-D-glucopyranosiduronic acid methyl ester diacetate;

3β-3-((O-α-L-arabinofuranosyl-(1→2)-O-6-deoxy-α-L-mannopyranosyl-(1→4)-β-D-glucopyranosyl)oxy)-lup-20(29)-en-28-oic acid;

3β-3-((O-α-L-arabinofuranosyl-(1→2)-O-6-deoxy-α-L-mannopyranosyl-(1→4)-β-D-glucopyranosyl)oxy)-lup-20(29)-en-28-oic acid methyl ester;

3β-28-hydroxylup-20(29)-en-3-yl-4-O-β-D-glucopyranosyl-β-D-glucopyranoside;

3β-28-hydroxylup-20(29)-en-3-yl-4-O-α-D-glucopyranosyl-β-D-glucopyranoside;

3β-3-hydroxylup-20(29)-en-28-yl-4-O-α-D-glucopyranosyl-β-D-glucopyranoside;

3β-28-hydroxylup-20(29)-en-3-yl-β-D-xylopyranoside;

3-(β-D-glucopyranosyloxy)lup-20(29)-en-28-oic acid O-6-deoxy-α-L-mannopyranosyl-(1→4)-O-β-D-glucopyranosyl-(1 6)-O-β-D-glucopyranosyl ester;

3α-lup-20(29)-en-28-oic acid 3-(β-D-glucopyranosyloxy)-O-6-deoxy-α-L-mannopyranosyl-(1→4)-O-β-D-glucopyranosyl-(1→6)-O-β-D-glucopyranosyl ester;

3α,4-α-3-(β-D-glucopyranosyloxy)lup-20(29)-en-28-oic acid;

3α-lup-20(29)-en-28-oic acid 3-((O-6-acetyl-β-D-glucopyranosyl)oxy)-O-6-deoxy-α-L-mannopyranosyl-(1→4)-O-β-D-glucopyranosyl-(1→6)-O-β-D-glucopyranosyl ester;

3β-28-hydroxylup-20(29)-en-3-yl-O-α-D-glucopyranosyl-(1→4)-O-α-D-glucopyranosyl-(1→4)-O-β-D-glucopyranosyl-(1→4)-β-D-glucopyranoside;

3α-3-(sulfooxy)lup-20(29)-en-28-oic acid 28-O-6-deoxy-α-L-mannopyranosyl-(1→4)-O-β-D-glucopyranosyl-(1→6)-β-D-glucopyranosyl ester;

3-(sulfooxy)lup-20(29)-en-28-oic acid 28-(O-2,3,4-tri-O-acetyl-6-deoxy-α-L-mannopyranosyl-(1→4)-O-2,3,6-tri-O-acetyl-β-D-glucopyranosyl-(1→6)-2,3,4-tri-O-acetyl-β-D-glucopyranosyl) ester;

3α-3-(acetyloxy)lup-20(29)-en-28-oic acid O-2,3,4-tri-O-acetyl-6-deoxy-α-L-mannopyranosyl-(1→4)-O-2,3,6-tri-O-acetyl-β-D-glucopyranosyl-(1→6)-2,3,4-tri-O-acetyl-β-D-glucopyranosyl) ester;

28-(acetyloxy)lup-20(29)-en-3-yl-4-O-(2,3,4,6-tetra-O-acetyl-α-D-glucopyranosyl)-β-D-glucopyranoside triacetate;

3β-28-(acetyloxy)lup-20(29)-en-3-yl-4-O-(2,3,4,6-tetra-O-acetyl-β-D-glucopyranosyl)β-D-glucopyranoside triacetate;

3β-3-(acetyloxy)lup-20(29)-en-28-yl-4-O-(2,3,4,6-tetra-O-acetyl-α-D-glucopyranosyl)-β-D-glucopyranoside triacetate;

3β-3-((2,3,4,6-tetra-O-acetyl-β-D-glucopyranosyl)oxy)lup-20(29)-en-28-yl-β-D-glucopyranoside tetraacetate;

3β-28-(acetyloxy)lup-20(29)-en-3-yl-β-D-glucopyranoside tetraacetate;

3β-3-(acetyloxy)lup-20(29)-en-28-yl-β-D-glucopyranoside tetraacetate;

3β-lup-20(29)-en-3-yl-β-D-glucopyranoside tetraacetate;

3β-lup-20(29)-en-3-yl-6-deoxy-α-L-mannopyranoside;

3β-3-((6-deoxy-2-O-β-D-glucopyranosyl-α-L-mannopyranosyl)oxy)lup-20(29)-en-28-oic acid;

3β-3-((6-deoxy-α-L-mannopyranosyl)oxy)lup-20(29)-en-28-oic acid;

3β-lup-20(29)-en-3-yl-4-O-β-D-xylopyranosyl-β-D-glucopyranoside;

3β-28-(acetyloxy)lup-20(29)-en-3-yl-α-D-glucopyranoside tetraacetate;

3β-3-hydroxylup-20(29)-en-28-yl-β-D-glucopyranoside 2,3,4,6-tetraacetate;

3β-28-((6-O-D-apio-β-D-furanosyl-β-D-glucopyranosyl)oxy)-28-oxolup-20(29)-en-3-yl-4-O-β-D-galactopyranosyl-β-D-glucopyranosiduronic acid;

3β-3-((2-propenyl)oxy)lup-20(29)-en-28-oic acid ("3-O-allylbetulinic acid");

3β-3,28-dimethoxylup-20(29)-ene ("3,28-di-O-methyl-betulin");

3β-3,28-dimethoxylupane ("3,28-di-O-methyldihydro-betulin");

3β-28-methoxylupan-3-ol ("28-methyldihydrobetulin");

3β-3-methoxylup-20(29)-en-28-oic acid ("3-O-methyl-betulinic acid");

3β-3-methoxylup-20(29)-en-28-oic acid methyl ester ("methyl 3-O-methylbetulinate");

9ξ-2,6-anhydro-9-O-((3β,18β)-17-carboxy-28-norlupan-3-yl)-1,7,8-trideoxy-8-methyl-3,4,5-tris-O-(phenylmethyl)-L-glycero-D-galactononitol;

2,6-anhydro-9-O-((3β,18β)-17-carboxy-28-norlup-20(29)-en-3-yl)-1,7,8-trideoxy-8-methylene-3,4,5-tris-O-(phenylmethyl)-L-glycero-D-galactononitol;

3α-3-methoxylup-20(29)-en-28-oic acid;

3α-3-methoxylup-20(29)-en-28-oic acid methyl ester;

3β-28-(acetyloxy)lup-20(29)-en-3-yl-β-D-glucopyranoside ("28-acetyl-3-β-D-glucosylbetulin");

3β-28-(acetyloxy)lup-20(29)-en-3-yl-β-D-galactopyranoside ("28-acetyl-3-β-D-galactosylbetulin"); and 3β-3-(acetyloxy)lup-20(29)-en-28-yl-β-D-glucopyranoside ("3-acetyl-28-β-D-glucosylbetulin");

a D-enantiomer, L-enantiomer or racemate thereof, or a pharmaceutically acceptable salt thereof.

In one embodiment of the invention, the compound of formula (I) is administered within a composition comprising a pharmaceutically acceptable carrier or vehicle.

The compounds of formula (I) may be administered by a variety of methods including orally, sublingually, intranasally, intramuscularly, intravenously, subcutaneously, intravaginally, transdermally, rectally, by inhalation, or as a mouthwash.

The compositions of the invention and the methods disclosed herein are particularly advantageous for the treatment of neuroectodermal tumors that are resistant to most commonly used chemotherapeutic agents. In one embodiment, the method involves administering betulinic acid and derivatives thereof and/or compositions comprising the same to a subject systemically. In another embodiment, the method involves the application, of betulinic acid or its derivatives to a tumor locally. In some preferred embodiment, betulinic acid is systemically administered to a patient inflict with a doxorubin-resistant neuroectodermal tumor.

IV. BRIEF DESCRIPTION OF THE DRAWINGS

Figure 1B:
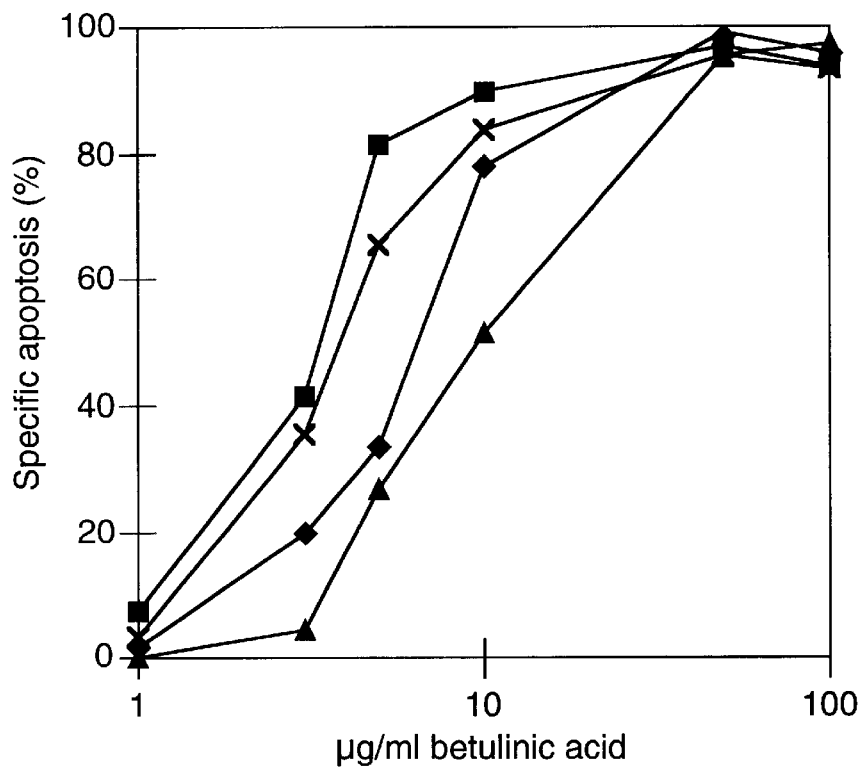
Figure 1C:
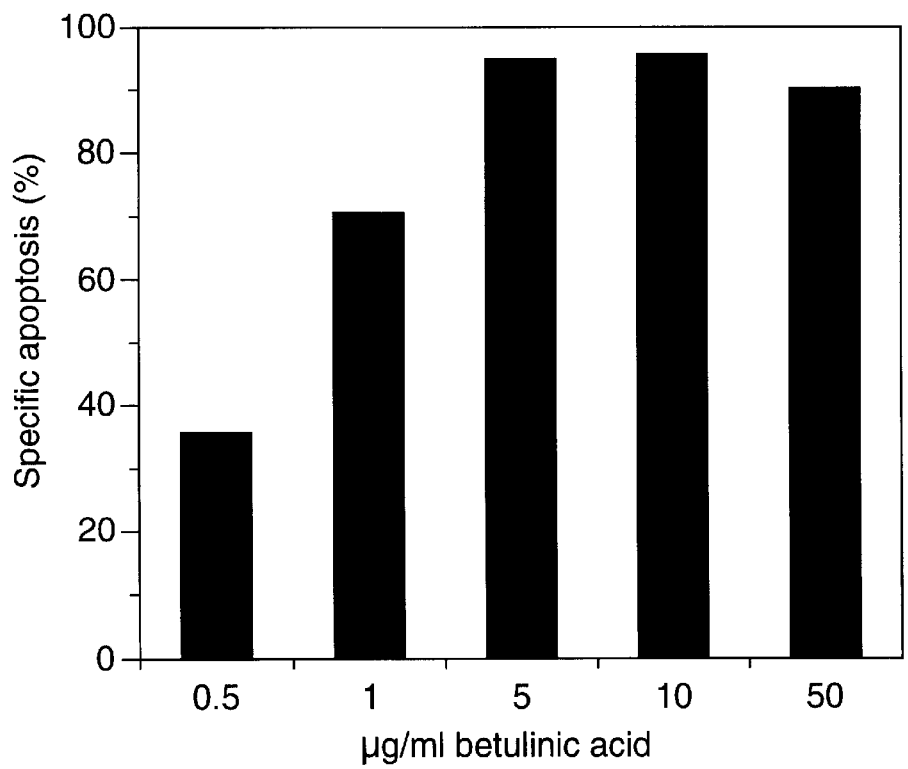

FIGS. 1A–C show the induction of apoptosis by betulinic acid.

FIGS. 2A–E show betulinic acid induced activation of caspase.

Figure 3A:
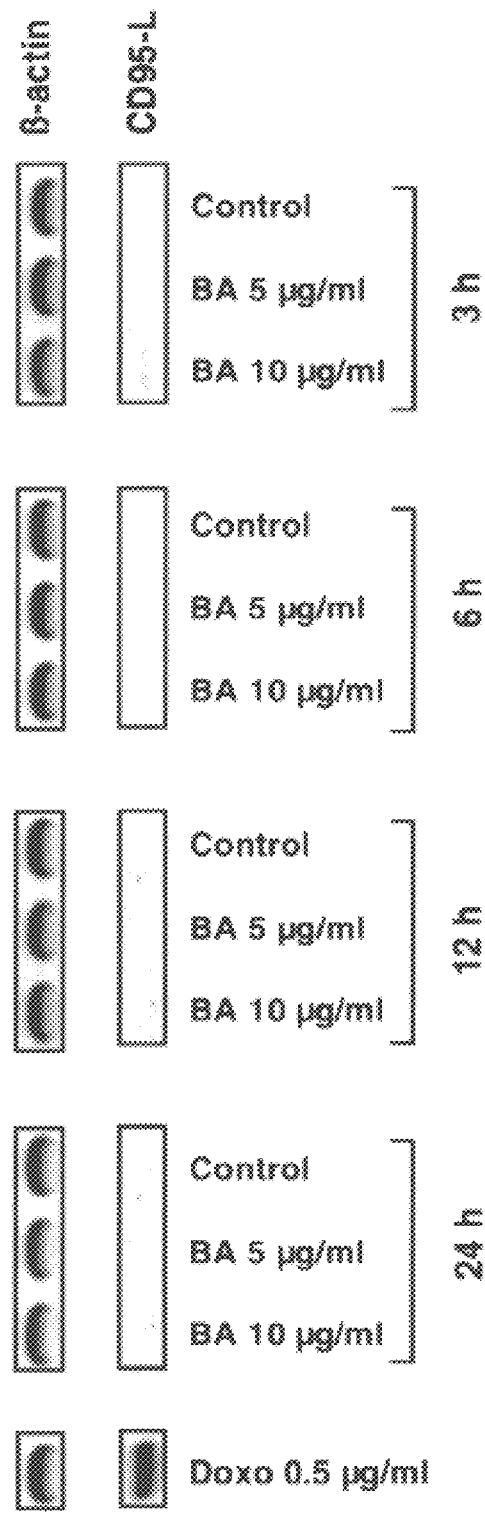
Figure 3B:
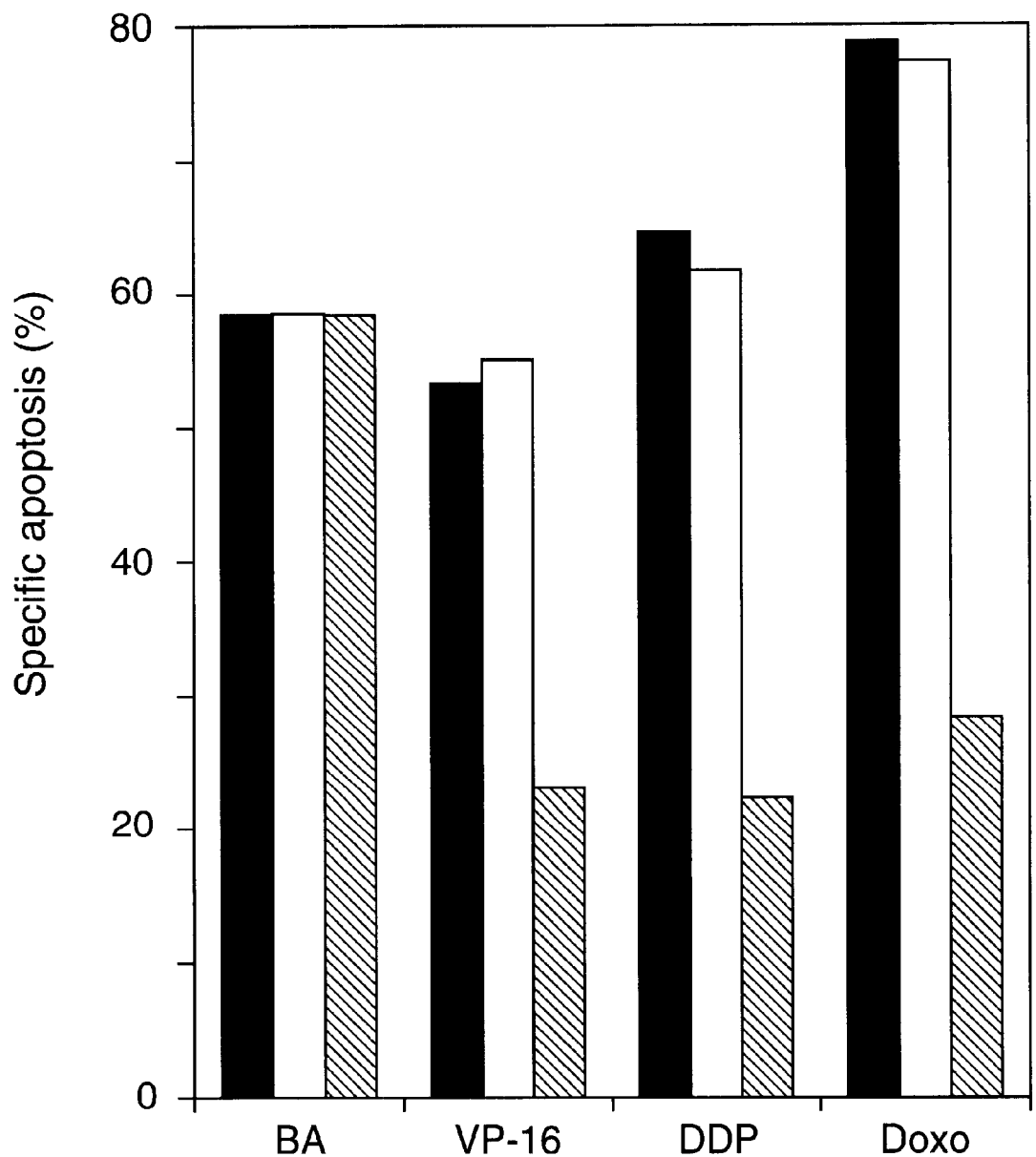

FIGS. 3A–B show CD95-independent induction of apoptosis.

Figure 4A:
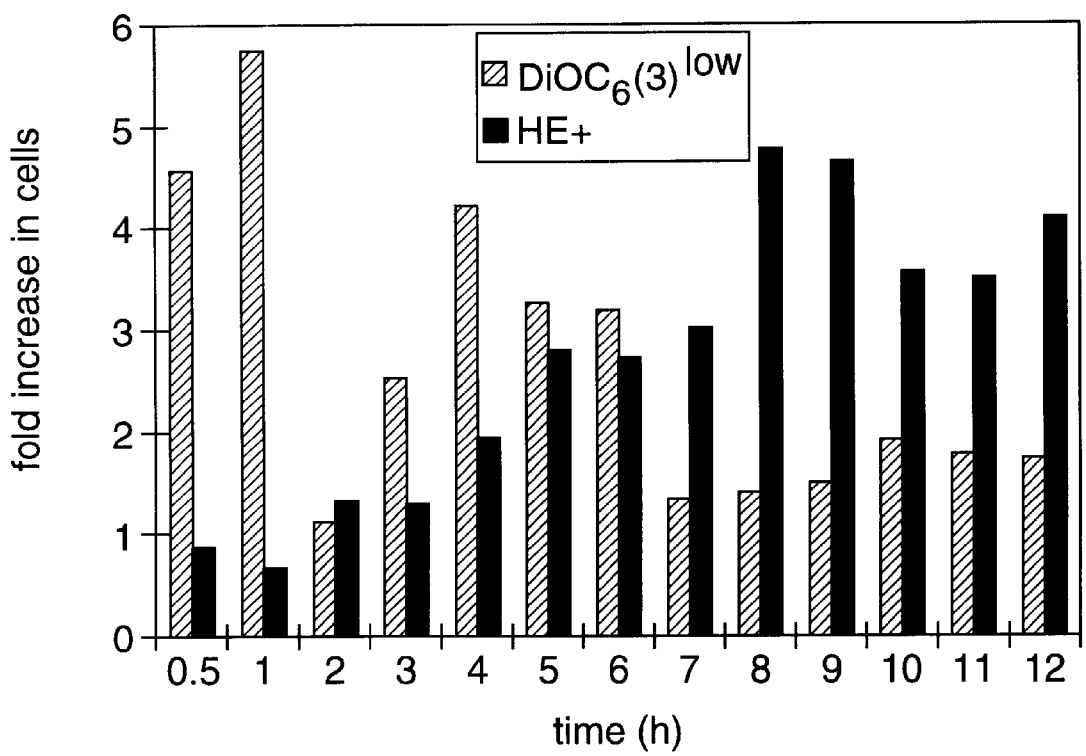
Figure 4B:
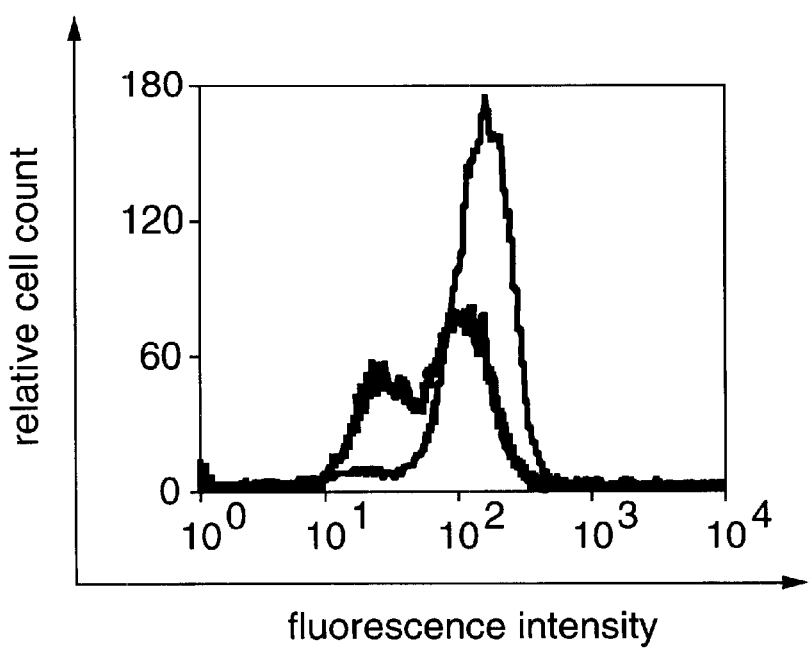

FIGS. 4A–B show betulinic acid induced disturbance of mitochondrial function.

FIGS. 5A-1, 5A-2 and 5B-D show the involvement of Bcl-2 related proteins and p53 in betulinic acid induced apoptosis.

Figure 6A:
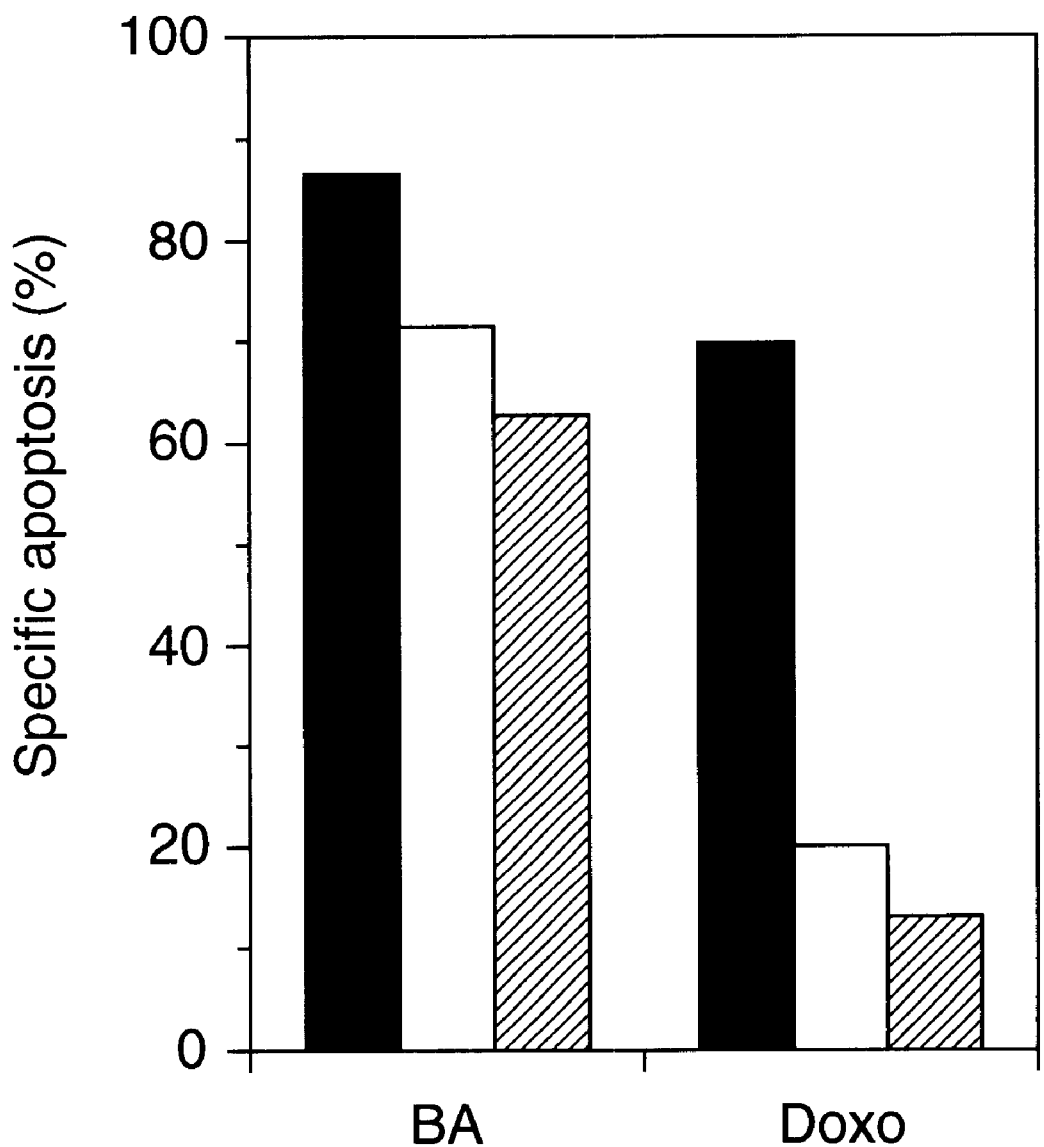
Figure 6B:
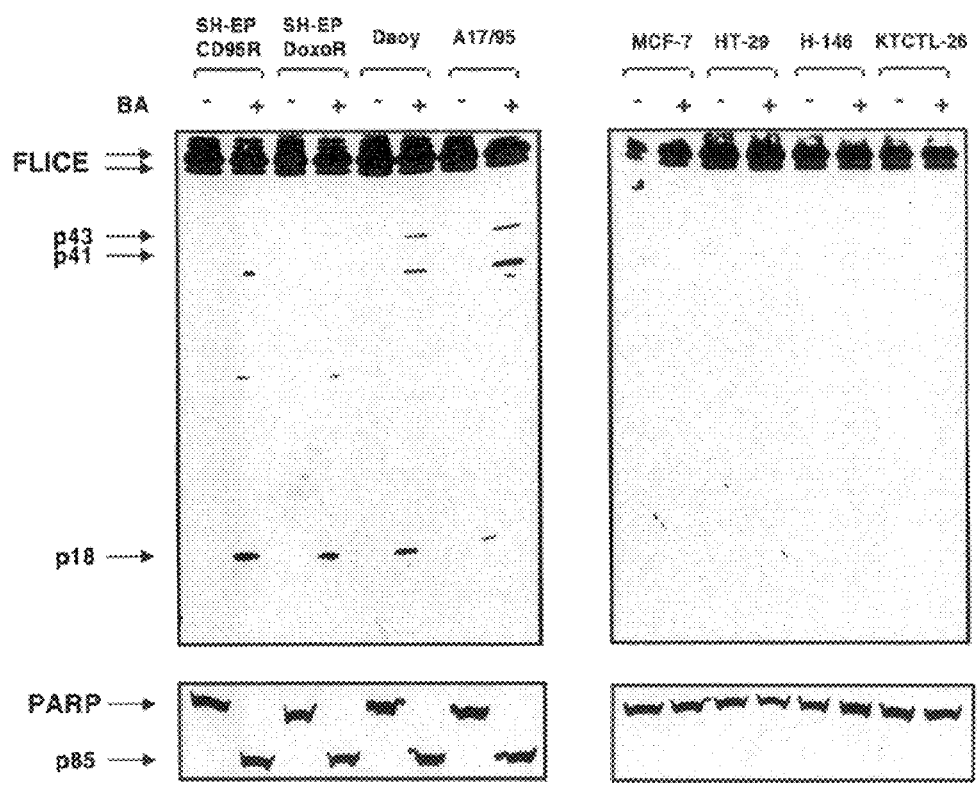

FIGS. 6A–B show the effect of betulinic acid on drug resistant cells.

Figure 7:
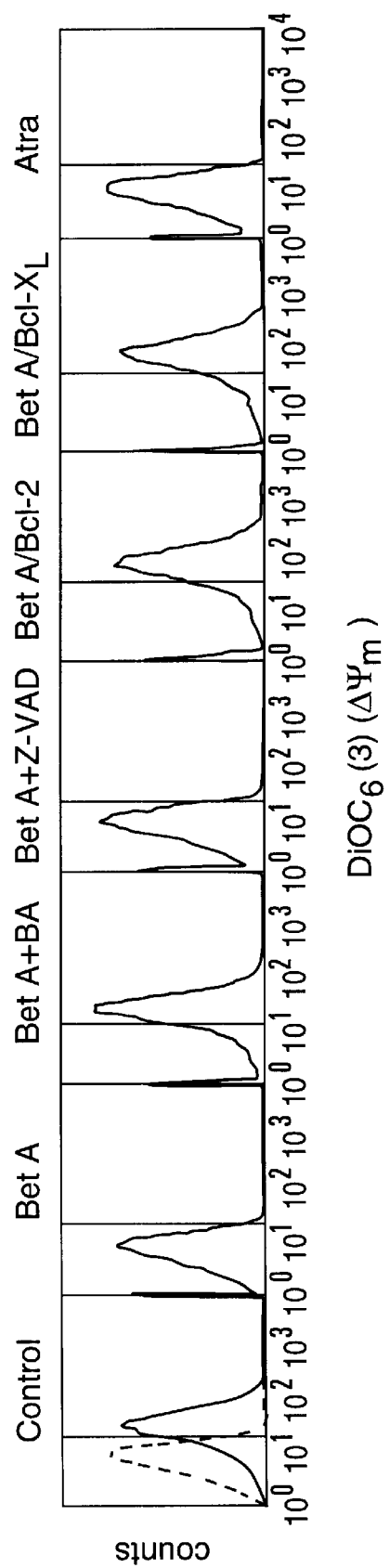

FIG. 7 shows that betulinic acid directly triggers mitochondrial permeability transition.

Figure 8A:
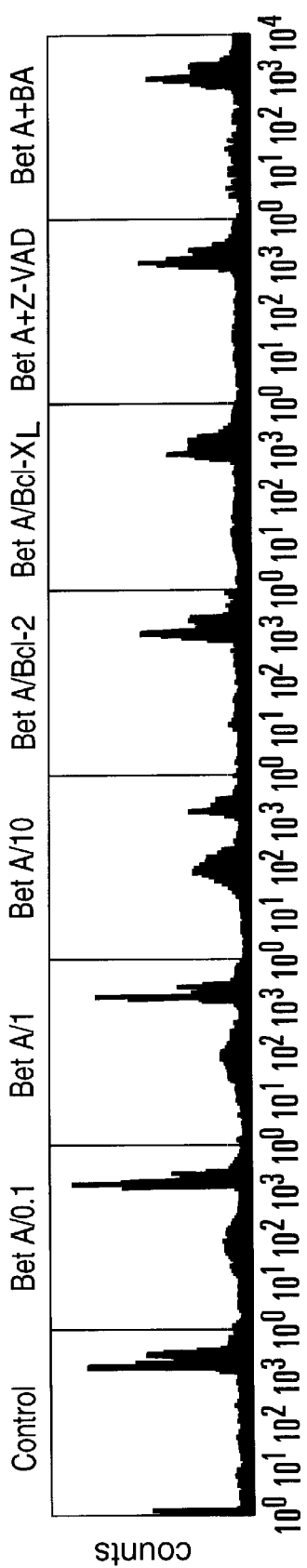
Figure 8B:
Figure 8C:
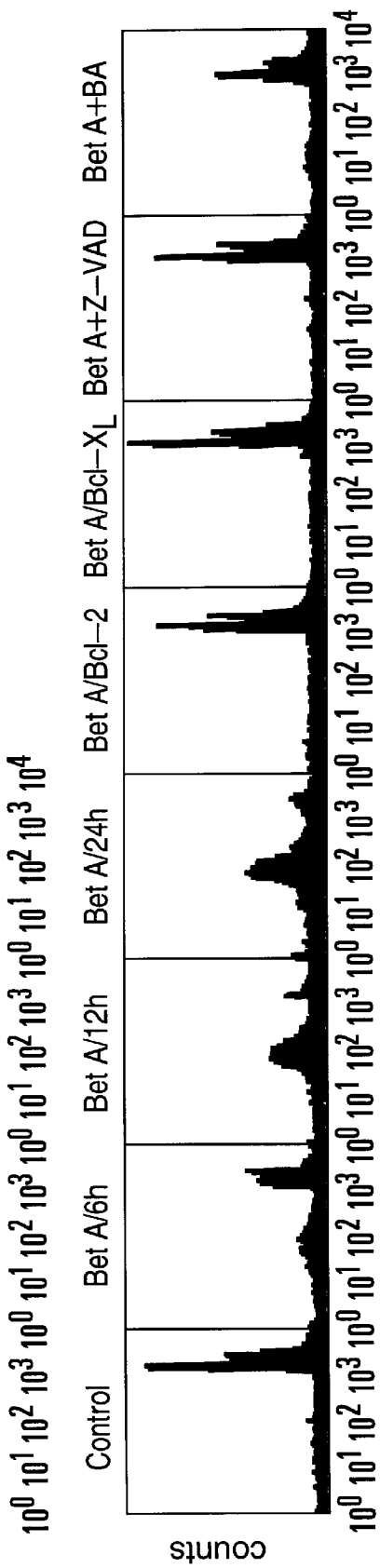

FIGS. 8A–C show that betulinic acid-induced mitochondrial permeability transition triggers nuclear fragmentation.

Figure 9A:
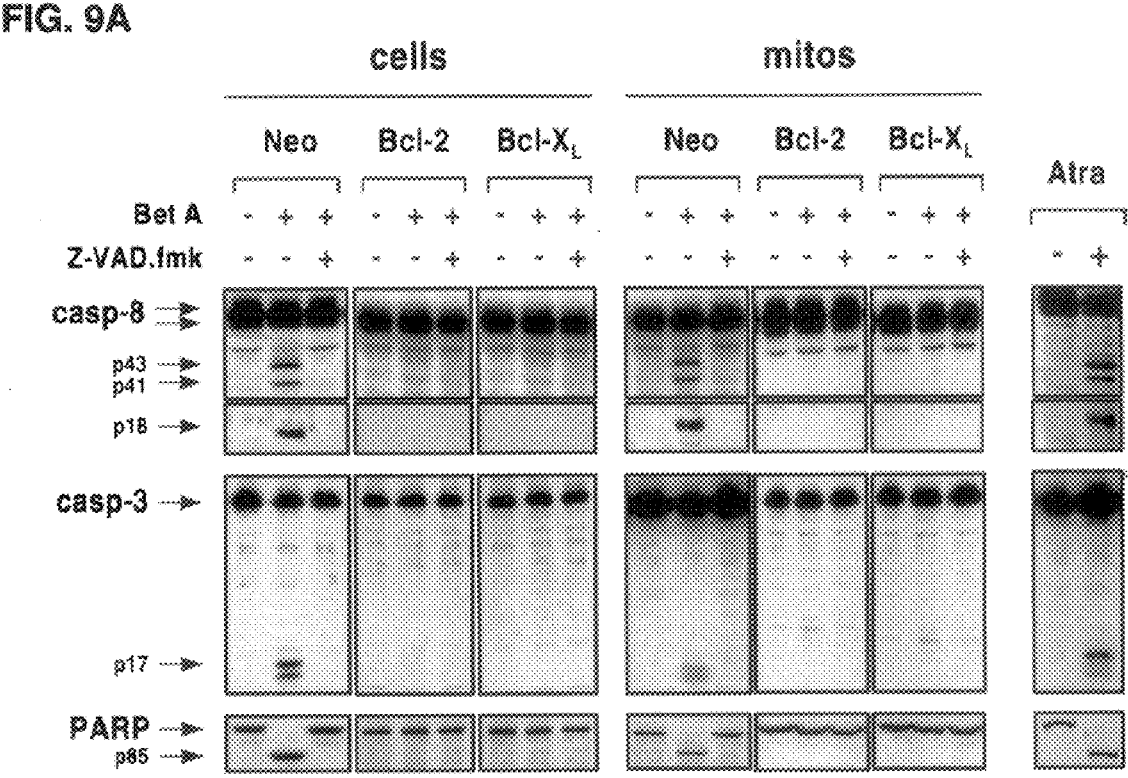

FIGS. 9A and B show that betulinic acid-induced cleavage caspases depends on mitochondrial permeability transition.

Figure 10A:
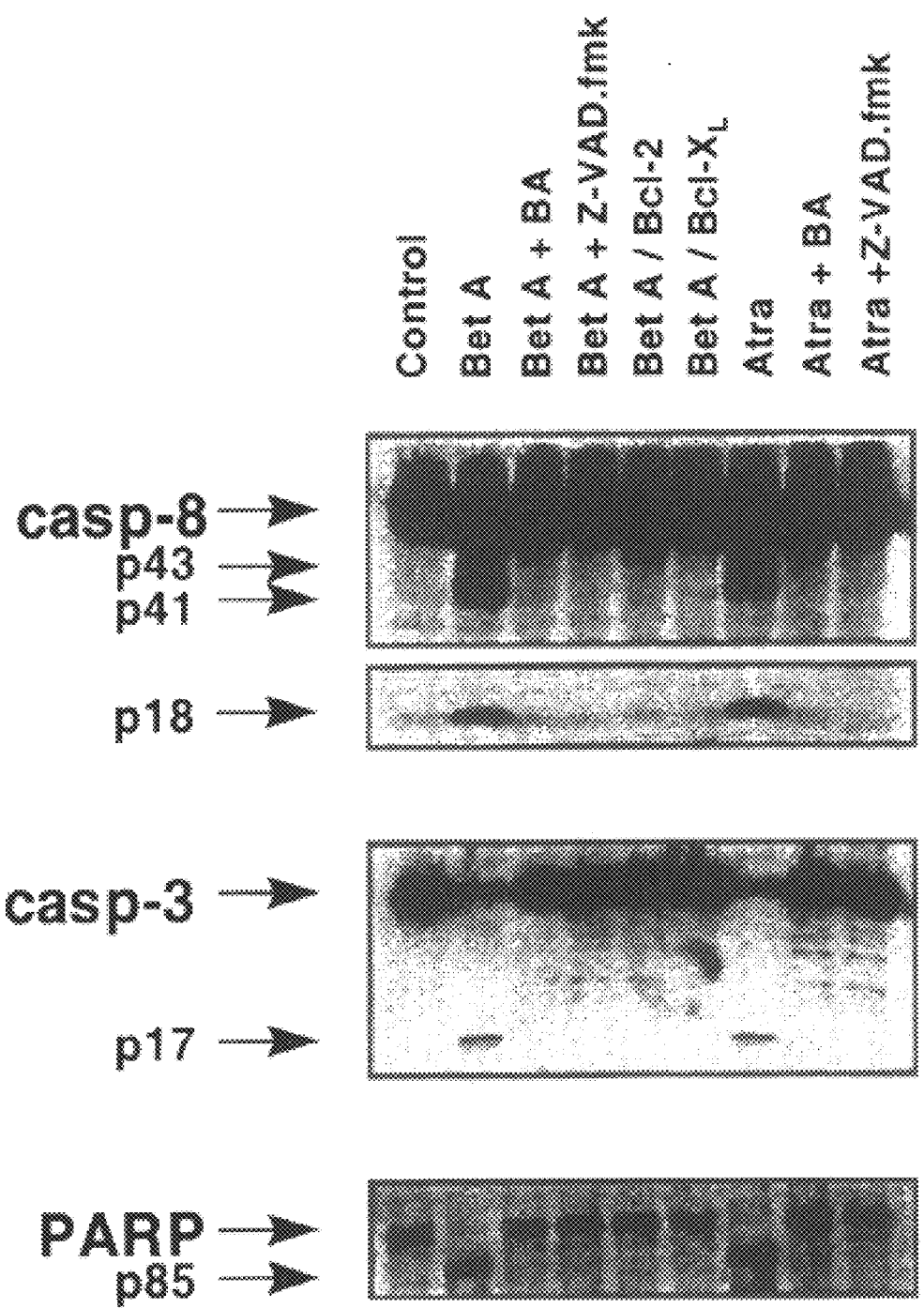
Figure 10B:
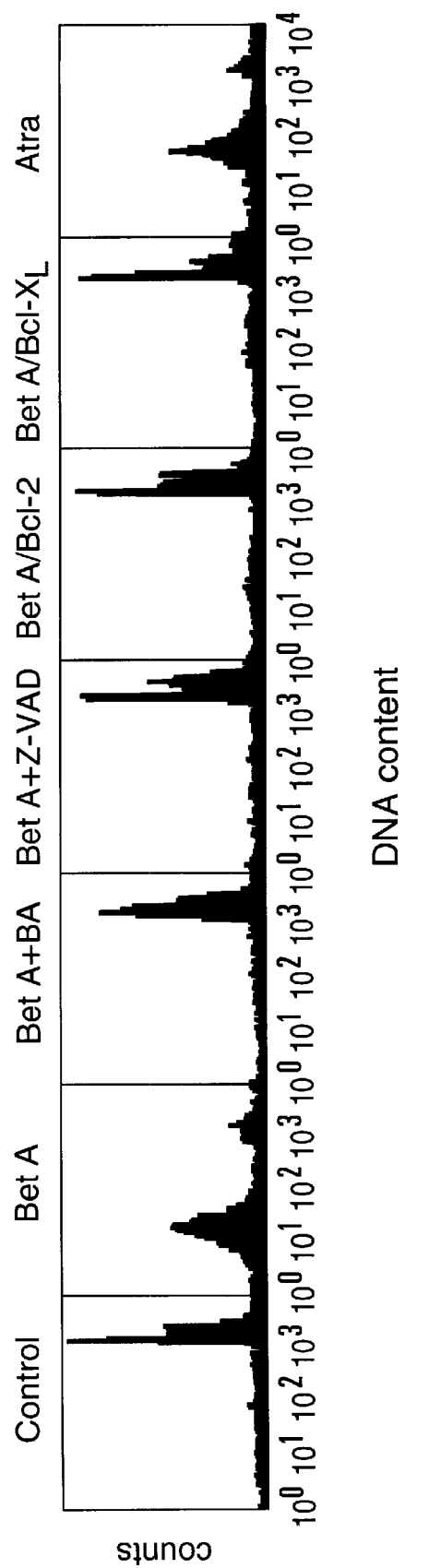
Figure 10C:
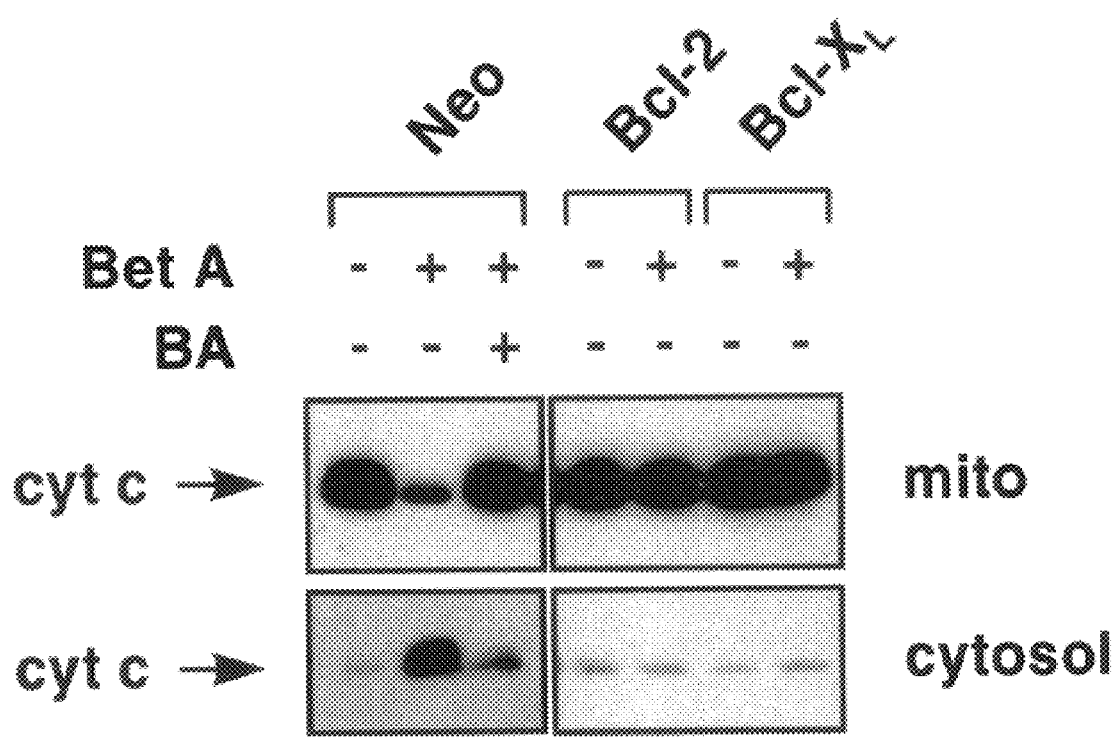

FIGS. 10A–C show that betulinic acid causes the release of apoptogenic factor(s) from isolated mitochondria.

Figure 11A:
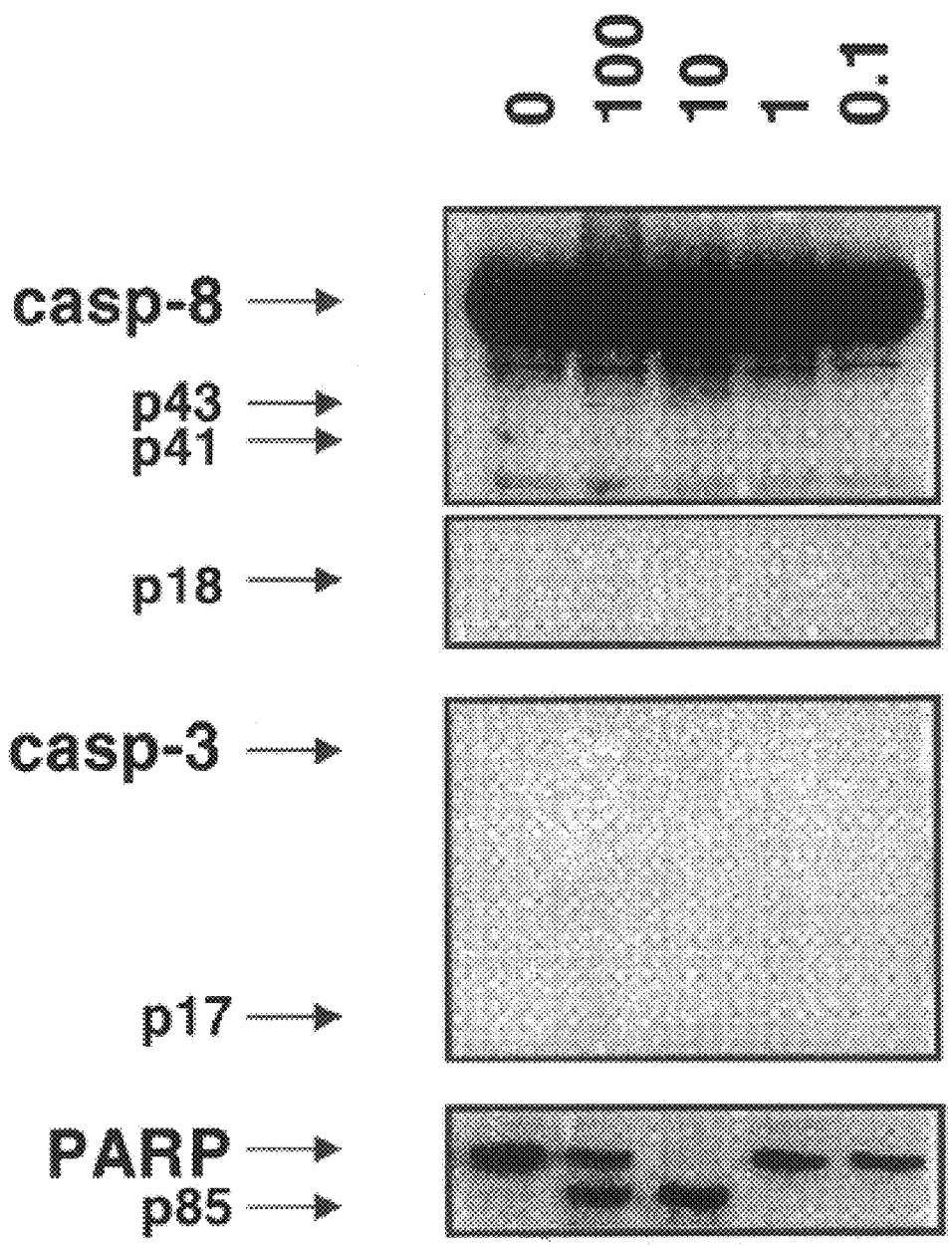
Figure 11B:
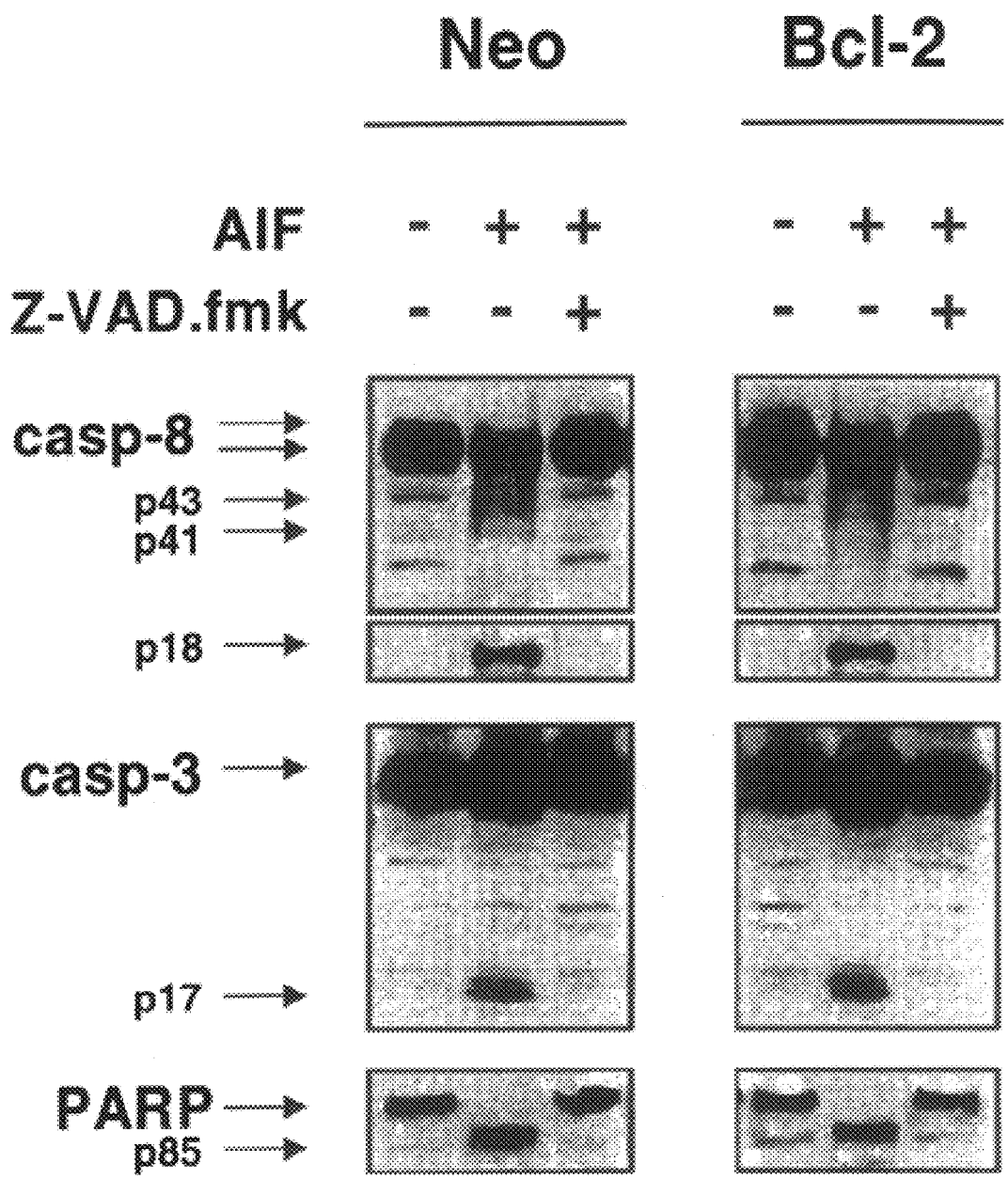
Figure 11C:
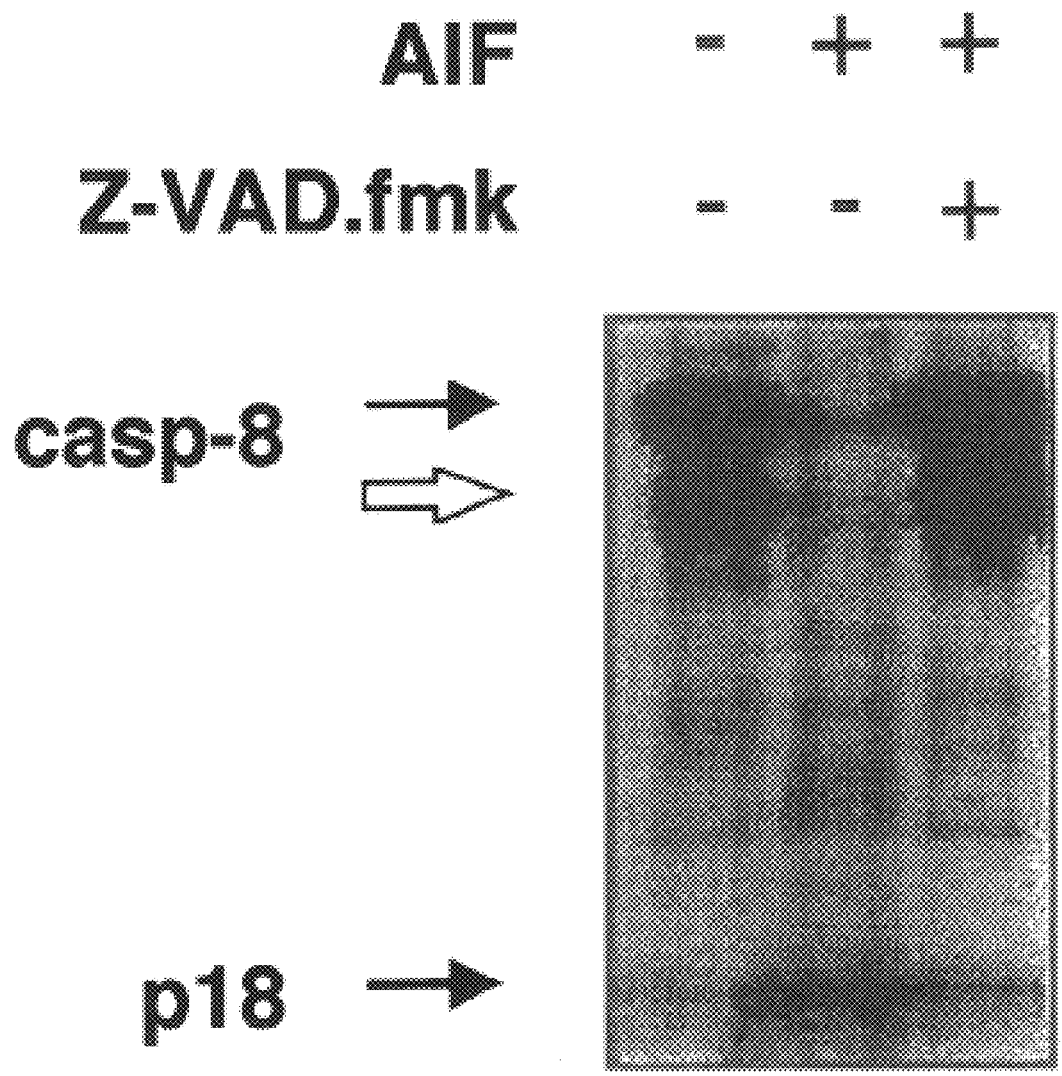

FIGS. 11A–C show that apoptogenic proteins released from mitochondria induce cleavage of caspases.

FIGS. 12A–D show drug-induced apoptosis and mitochondrial PT.

Figure 13A:
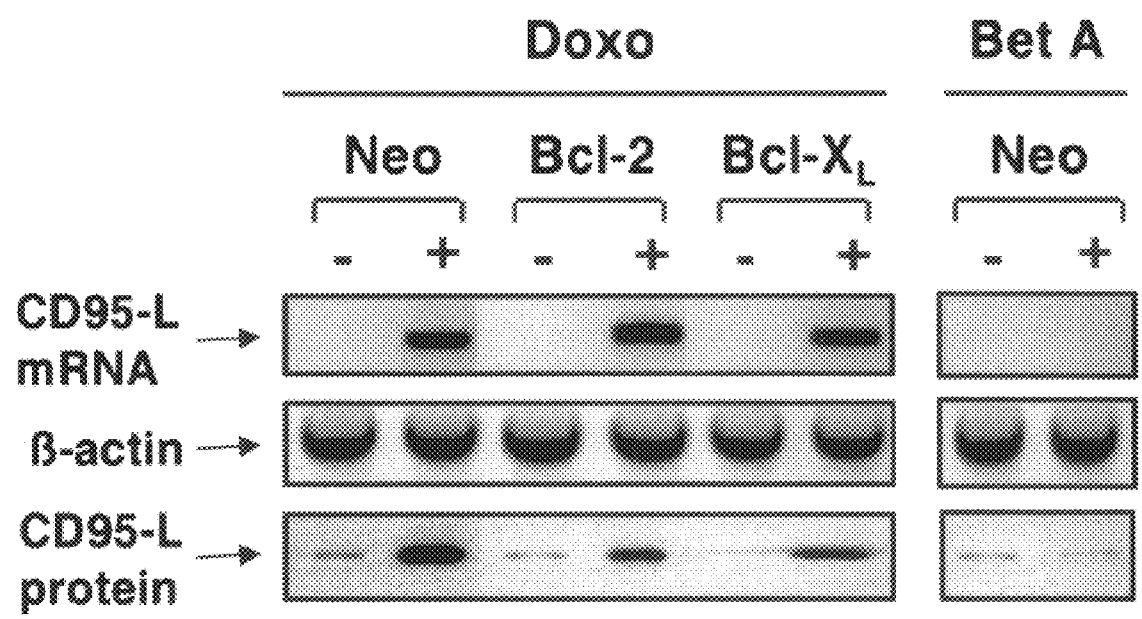
Figure 13B:
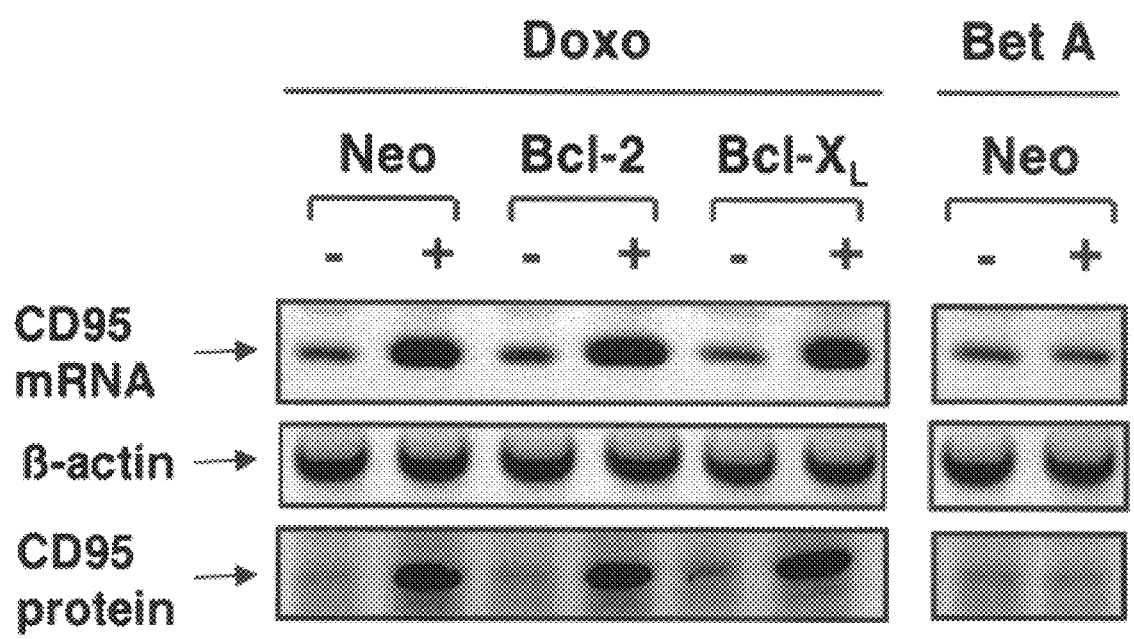
Figure 13C:
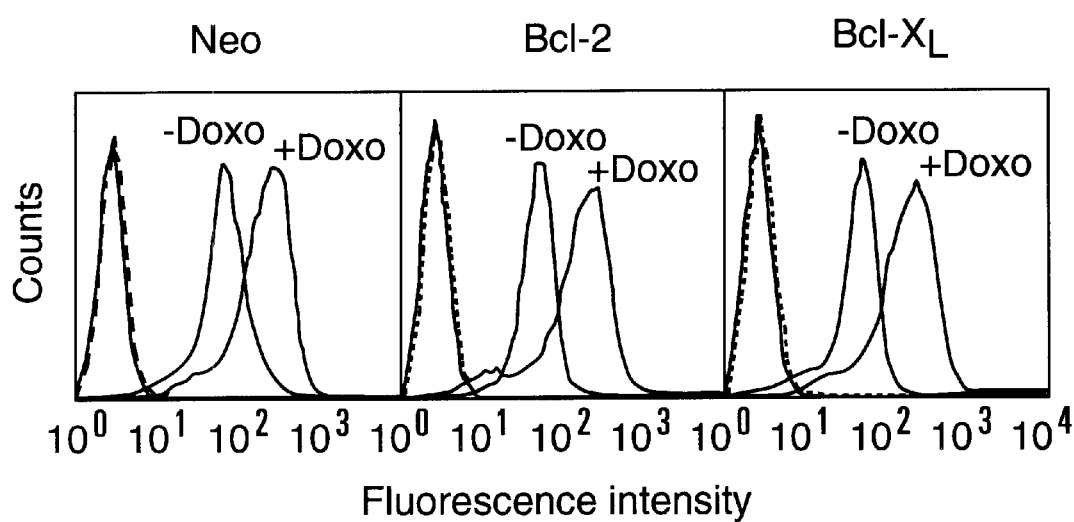

FIGS. 13A–C show that the activation of the CD95 system by Doxorubicin occurs upstream of mitochondria.

FIGS. 14A, 14B-1 and 14B-2 show the functional relationship between $\Delta\Psi_m$ disruption and activation of the caspase cascade.

Figure 15A:
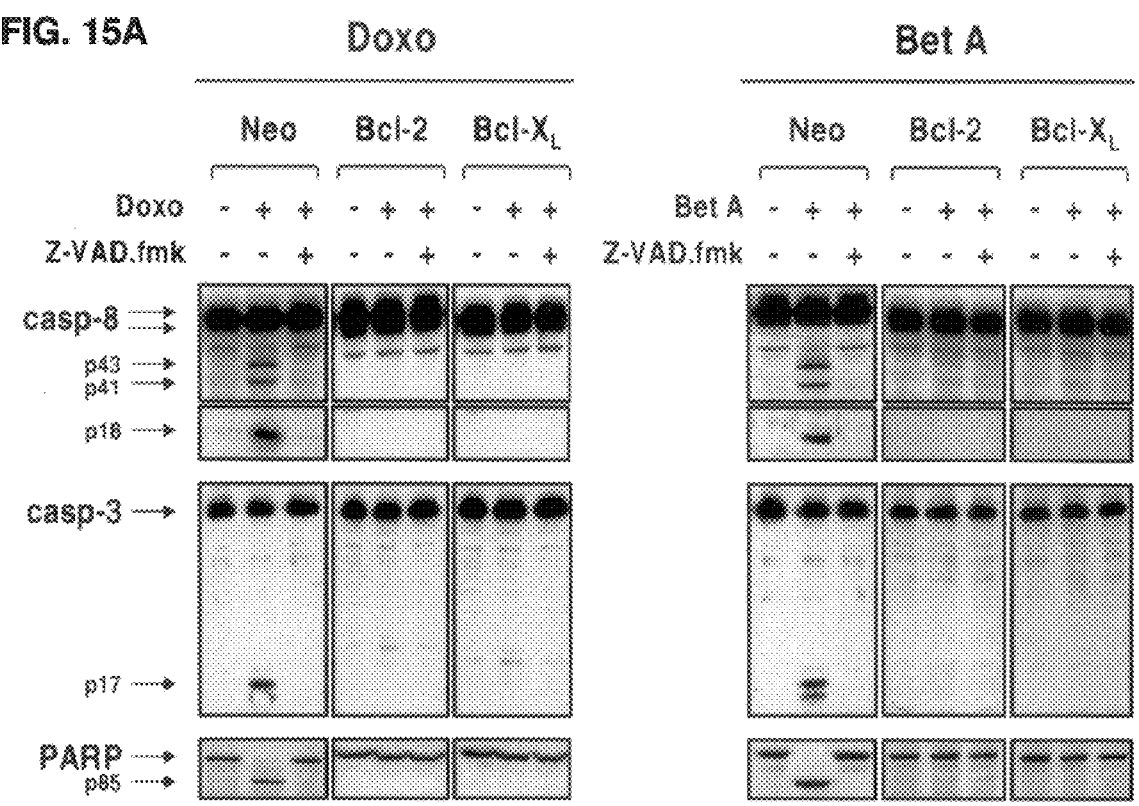
Figure 15B:
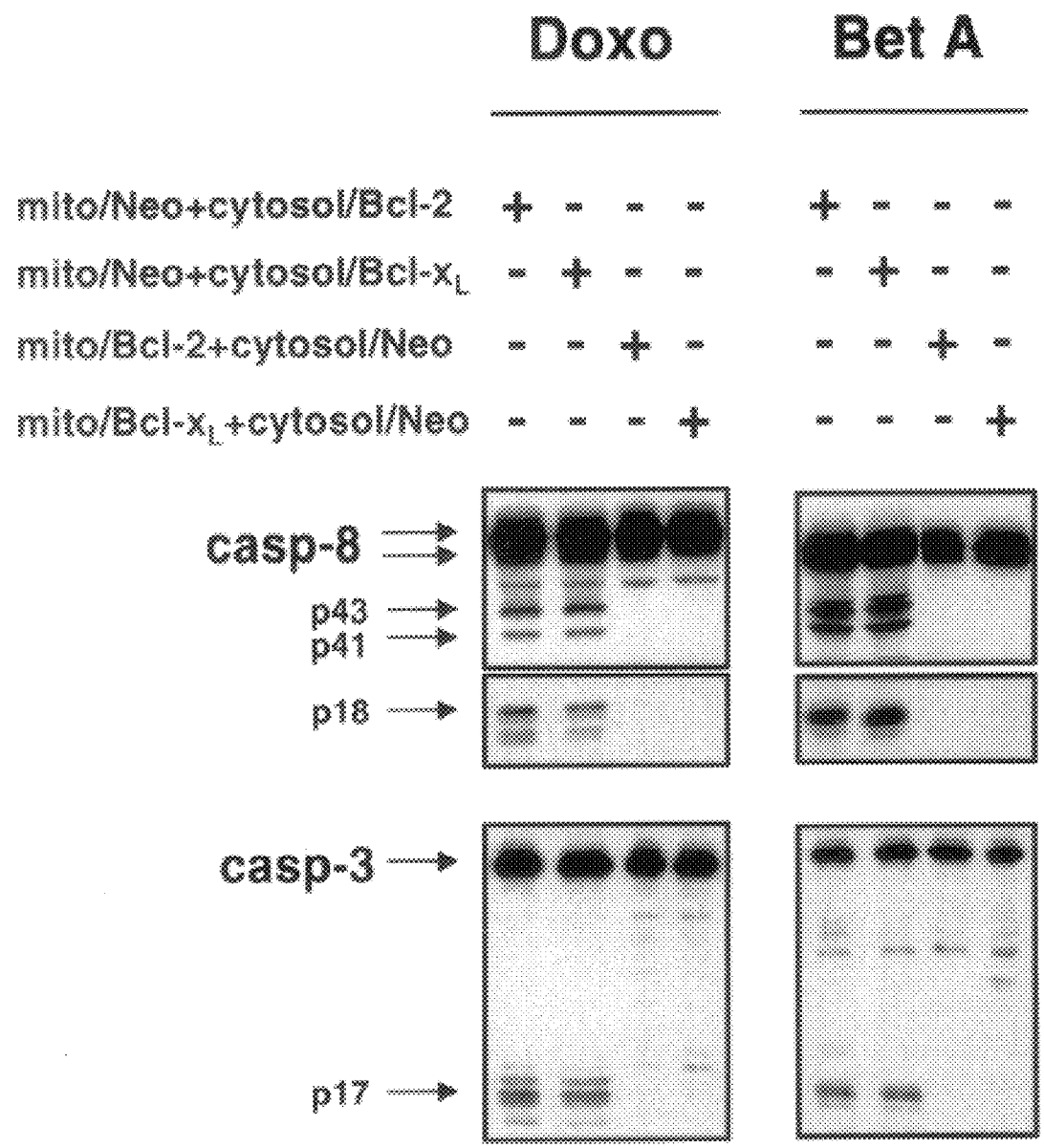

FIGS. 15A–B show the activation of caspases in CFS.

Figure 16A:
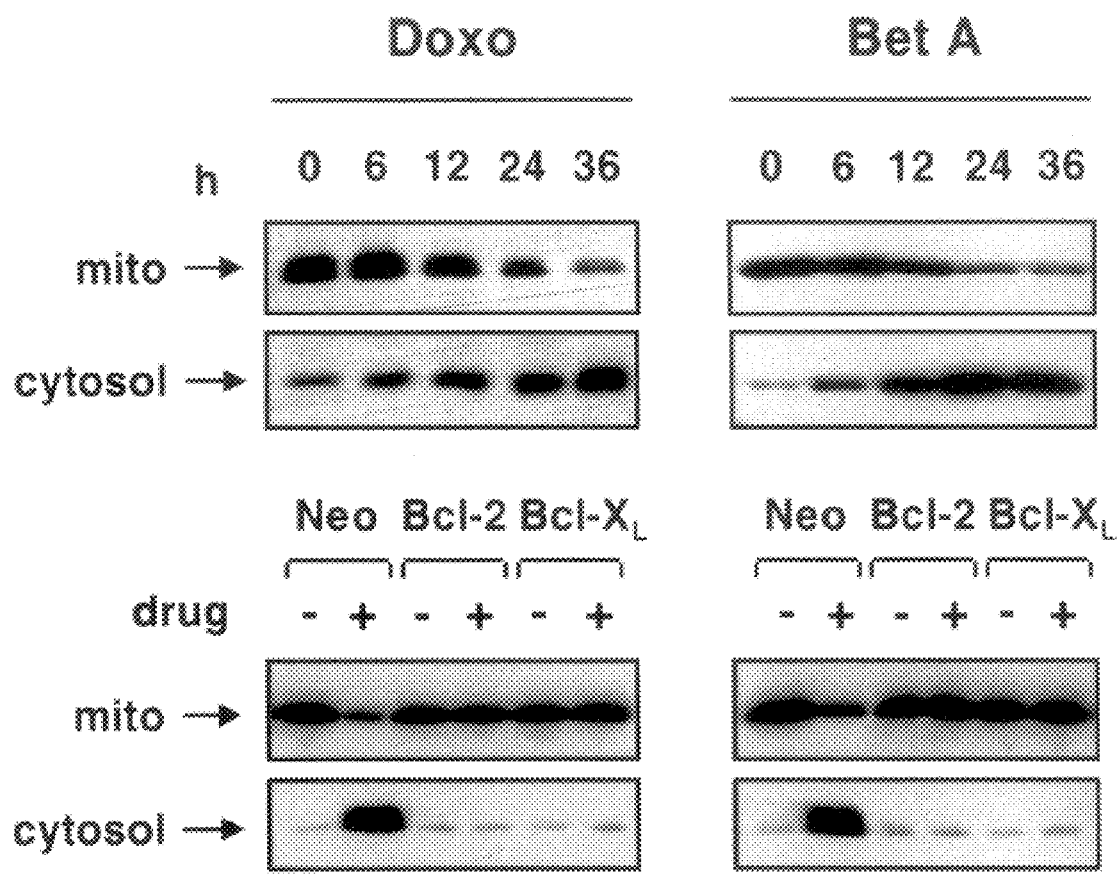
Figure 16B:
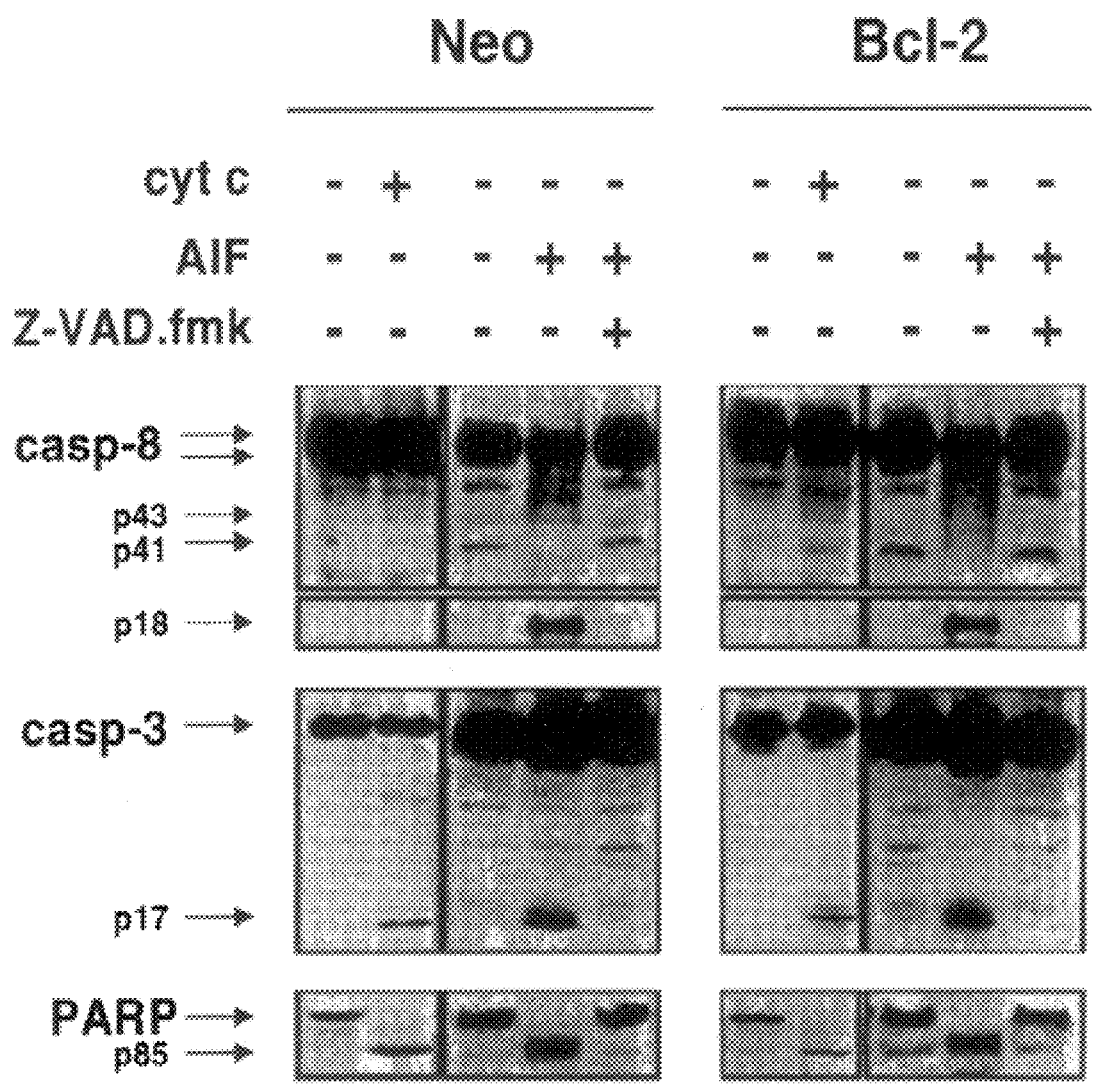

FIGS. 16A–B show the cleavage of caspases by cyt. c and AIF.

Figure 17A:
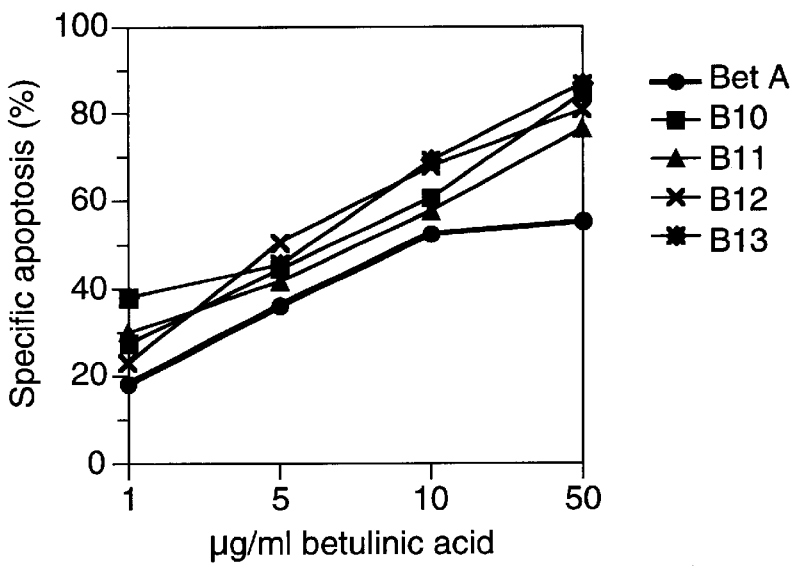
Figure 17B:
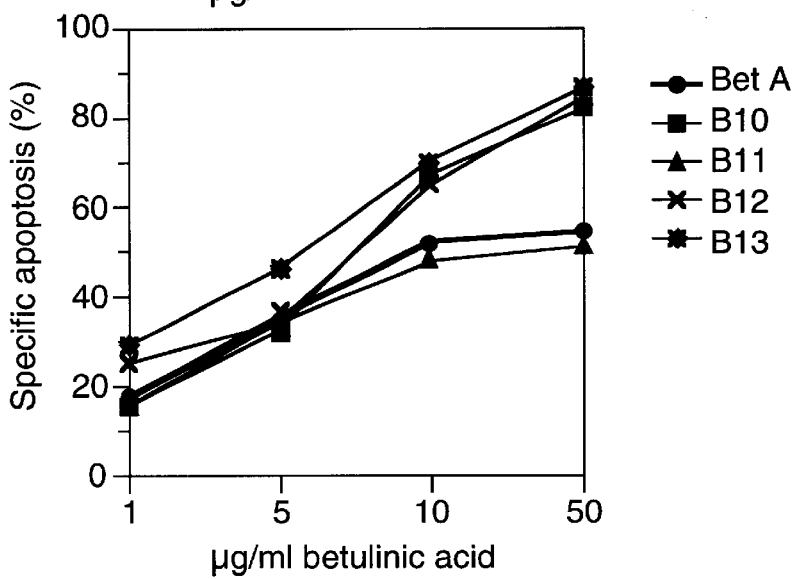
Figure 17C:
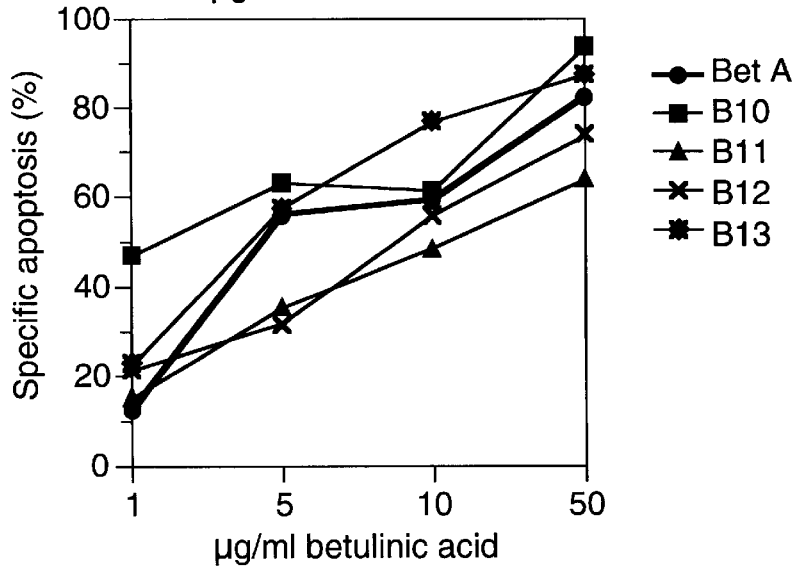

FIGS. 17A–C show the induction of apoptosis by betulinic acid derivatives.

V. DETAILED DESCRIPTION OF THE INVENTION

A. Overview of the Invention

The invention is based, in part, on the inventors' unexpected discovery that betulinic acid and derivatives thereof effectively inhibit the growth of a variety of neuroectodermal cells. The invention is further based, in part, on the unexpected discovery that betulinic acid and its derivatives exert their activity through different pathways than routinely used chemotherapeutical agents. As discussed, surpa, Section I., treatment of neuroectodermal tumors often requires long term, combination chemotherapy. Patients often develop resistance to chemotherapeutical agents after a long term use of such agents. Indeed, it is known many chemotherapeutical agents exert their anti-tumor activity by inducing apoptosis in target tumor cells. A large number of such agents induce tumor cell apoptosis through apoptosis signaling systems, in particular, the CD95 and p53 systems, in the target tumor cells. However, frequently the target tumor cells develop drug resistance by mutating the components of the apoptosis signaling pathway. For example, loss of either CD95 or p53 confers drug resistance to the tumor cells. Acting through an apoptosis pathway that is distinct and independent from the CD95 and p53 systems, the compositions and methods of the invention offer the advantage that they are effective against tumors that are resistant to the most commonly used chemotherapeutic agents that act through CD95 and/or p53.

Thus, generally, the present invention is directed to betulinic acid and derivatives thereof, and their use for the treatment of neuroectodermal tumors. More specifically, the present invention is directed to novel derivatives of betulinic acid, and methods of their synthesis. Further, the present invention is directed to pharmaceutical compositions comprising the novel compounds of the invention and a pharmaceutically acceptable carrier useful for the treatment of neuroectodermal tumors. Finally, the present invention is directed to methods for the treatment of neuroectodermal tumors in a subject in need of such treatment by administration of pharmaceutical compositions comprising the compounds disclosed herein.

B. The Antitumor Activity of Betulinic Acid and Derivatives Thereof

Betulinic Acid Induced Apoptosis

Induction of tumor cell apoptosis (programmed cell death) is a powerful therapeutic approach toward the treatment of tumors. The term apoptosis refers to a morphologically distinctive form of cell death associated with normal physiology. Kerr et al., 1972, *Brit. J. Cancer* 26:239. Apoptosis is distinguished from necrosis associated with acute injury to cells. Morphologically, apoptosis is characterized by nuclear chromatin condensation, cytoplasmic shrinking, dilated endoplasmic reticulum, and membrane blebbing.

It is the inventors' discovery that betulinic acid and derivatives thereof induce apoptosis in neuroblastoma (SH-EP), medulloblastoma (Daoy), Ewing's sarcoma (A 17/95), and melanoma (A-378) cell lines. Although betulinic acid had been previously reported to exert cytotoxicity against a melanoma cell line (MEL-2), it was neither known nor was it expected that betulinic acid would be active against a wide variety of cancer cells. See, Dascupta and Pezzuto, PCT/US96/04016, disclosing that betulinic acid had only cytotoxic effects on MEL-2, among ten different tumor cells tested. It is therefore a surprising discovery that betulinic acid and its derivatives induce apoptosis in neuroectodermal cells.

Betulinic Acid Induced Apoptosis is Independent of CD95 and P53

Apoptotic cell death can be triggered by a wide variety of stimuli, and not all cells necessarily will die in response to the same stimulus. Among the more studied death stimuli is DNA damage, i.e., by irradiation or drugs used for cancer chemotherapy, which in many cells leads to apoptotic death via a pathway dependent on p53. Some hormones such as corticosteroids lead to death in particular cells, e.g., thymocytes, although other cell types may be stimulated. Some cell types express Fas, a surface protein which initiates an intracellular death signal in response to crosslinking. In other cases cells appear to have a default death pathway which must be actively blocked by a survival factor in order to allow cell survival.

Cytotoxic drugs, irrespective of their intracellular target, have been shown to cause death of sensitive target cells by inducing apoptosis. Fisher, 1994, *Cell,* 78:539–542. The CD95 (APO-1/Fas) system is a key mediator of drug-induced apoptosis in leukemia and neuroblastoma cells. Friesen et al., 1996, *Nature Med.,* 2:574–577; Faldo et al., 1997, *Cancer Res.* 57:3823–3829. Upon treatment with cytotoxic drugs, CD95 ligand (CD95-L) was induced and caused apoptosis in an autocrine or paracrine manner. CD95-L is a M, 40,000 type II transmembrane molecule of the TNFlnerve growth factor family of ligands (Suda at al., 1993, *Cell* 75:1169–1178) that may also occur in a soluble form released after proteolytic cleavage from the cell surface. Tonaka et al., 1995, *EMBO J.* 14:1129–1135.

It is a surprising discovery of the inventors that betulinic acid and its derivatives induce apoptosis of a tumor cell independently of the status of CD95 in the tumor cell. For example, as disclosed herein, infra, betulinic acid induces apoptosis in the SH-EP neuroblastoma cells without inducing the expression of CD95-L, while doxorubicin treatment induces the expression of CD95-L. When cells are treated with anti-APO-1 (anti-CD95) antibodies to block the function of CD95, the induction of apoptosis by betulinic acid is not affected. See, infra. In contrast, doxorubicin induced apoptosis is significantly blocked by anti-CD95 antibodies.

Besides CD95, p53 gene also has a crucial role in the execution of apoptosis. A variety of evidence implicates p53 in apoptosis. If the p53 is mutated in a cancer cell, the cells are less likely to go into apoptosis when treated with these chemotherapeutic agents. Radiation and DNA-damaging chemotherapeutic drugs tend to work through pathways involving p53. Loss of p53 function could lead to a marked increase in cellular chemoresistance and may contribute to the significant proportion of treatment failure observed in these tumors. See. e.g., Buttitta et al., 1997, *Proc. Ann. Meet. Am. Assoc. Cancer Res.* 38:A713.

As shown, infra, doxorubicin treatment induces the accumulation of p53 protein. In contrast, betulinic acid does not induce the accumulation of p53 protein, which suggests that the apoptosis inducing activity of betulinic acid is independent of the p53 protein.

While not intending to be bound by a particular theory, Examples 3 and 4, infra, show that betulinic acid directly triggered permeability transition PT in isolated mitochondria and induction of PT appears to be the initial event in betulinic acid-triggered apoptosis. Mitochondria undergoing PT releases apoptoenic proteins such as cytochrome c or apoptosis-inducing factor (AIF) from the mitochondrial intermembrane space into the cytosol, where they activate caspases and endonucleases. Kroemet et al., 1997, *Immunol. Today* 18:44–51; Susin et al., *J. Exp. Med.* 186:25–37.

As Examples 3 and 4, infra, show, inhibition of PT by overexpression of Bcl-2 or BCl-$X_L$ or by the mitochondrion-specific inhibitor bongkrekic acid prevented all manifestations of apoptosis in intact cells and in a cell-free system such as disruption of mitchondria transmembrane potential ($\Delta\Psi_m$), activation of caspases, cleavage of substrates (PARP) and nuclear fragmentation. In contrast to betulinic acid, classical cytotoxic drugs such as doxorubicin, cisplatinum or etoposide did not induce mitochondrial perturbations in isolated mitochondria, suggesting that mitochondrial PT, which occurred in intact cells during apoptosis triggered by these substances, was the consequence of a primary activation of other pathways or systems.

When added to intact cells, betulinic acid specifically induced mitochondrial alterations in SHEP neuroblastoma cells, but not in lymphoid cell lines. However, betulinic acid-treated mitochondria isolated from the B lymphoblastoid cell line SKW6.4 triggered mitochondrial PT and mediated nuclear fragmentation similar to mitochondria from SHEP cells. Thus, the specificity of betulinic acid for neuroectodermal tumors may be explained by a cell specific uptake and/or translocation of the compound to the mitochondrial compartment rather than by differences in mitochondria themselves.

C. The Compounds

In accordance with the present invention, the compounds useful for the treatment of neuroectodermal tumors are represented by the general formula (I):

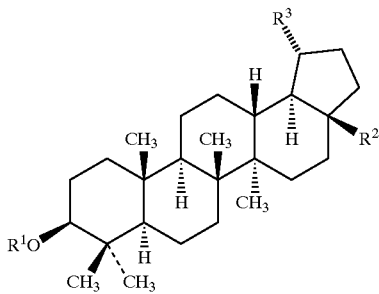

(I)

wherein $R^1$ is selected from the group consisting of hydrogen, —$SO_3H$, —$PO_3H_2$, —$C_1$–$C_{20}$ straight or branched chain alkyl, —$C_2$–$C_{20}$ straight or branched chain alkenyl, —$C_2$–$C_{20}$ straight or branched chain alkynyl, —$(CH_2CH_2O)_nH$, —$(CH_2CH_2O)_nCH_3$, —$(CH_2CH_2O)_nCH_2CH_3$, —$C(O)C_6H_5$, —$C(O)$ $C_1$–$C_{20}$ straight or branched chain alkyl, —$C(O)$ $C_2$–$C_{20}$ straight or branched chain alkenyl, —$C(O)$ $C_2$–$C_{20}$ straight or branched chain alkynyl, myo-inosityl, scyllo-inosityl, a cyclitol, conduritol A, quebrachitol, a monosaccharide, a disaccharide and an oligosaccharide; the —$(CH_2CH_2O)_nH$, myo-inosityl, scyllo-inosityl, cyclitol, conduritol A, quebrachitol, monosaccharide, disaccharide and oligosaccharide being optionally substituted with one or more —$C(O)$ $C_1$–$C_{20}$ straight or branched chain alkyl, —$C(O)$ $C_2$–$C_{20}$ straight or branched chain alkenyl, —$C(O)$ $C_2$–$C_{20}$ straight or branched chain alkynyl, sulfate, or mono-, di- or tri-phosphate groups;

$R^2$ is selected from the group consisting of —$CO_2H$, —$CO_2(C_6H_5)$, —$CO_2(C_1$–$C_{20}$ straight or branched chain alkyl), —$CO_2(C_2$–$C_{20}$ straight or branched chain alkenyl), —$CO_2(C_2$–$C_{20}$ straight or branched chain alkynyl), —$CO_2(myo$-inosityl), —$CO_2(scyllo$-inosityl), —$CO_2(cyclitol)$, —$CO_2(conduritol\ A)$, —$CO_2(quebrachitol)$, —$CO_2(monosaccharide)$, —$CO_2(disaccharide)$, —$CO_2(oligosaccharide)$, —$CO$ $(OCH_2CH_2)_nOH$, —$CO(OCH_2CH_2)_nOCH_3$, —$CO$ $(OCH_2CH_2)_nOCH_2CH_3$, —$CH_2OH$, —$CH_2OSO_3H$, —$CH_2OPO_3H_2$, —$CH_2O(C_6H_5)$, —$CH_2O(C_1$–$C_{20}$ straight or branched chain alkyl), —$CH_2O(C_2$–$C_{20}$ straight or branched chain alkenyl), —$CH_2O(C_2$–$C_{20}$ straight or branched chain alkynyl), —$CH_2O_2C$ ($C_1$–$C_{20}$ straight or branched chain alkyl), —$CH_2O_2C$ ($C_2$–$C_{20}$ straight or branched chain alkenyl), —$CH_2O_2C(C_2$–$C_{20}$ straight or branched chain alkynyl), —$CH_2O(myo$-inosityl), —$CH_2O(scyllo$-inosityl), —$CH_2O(cyclitol)$, —$CH_2O(conduritol\ A)$, —$CH_2O(quebrachitol)$, —$CH_2O(monosaccharide)$, —$CH_2O(disaccharide)$, —$CH_2O(oligosaccharide)$, —$CH_2(OCH_2CH_2)_nOH$, —$CH_2(OCH_2CH_2)_nOCH_3$, —$CH_2(OCH_2CH_2)_nOCH_2CH_3$, —$CH_2O_2C$ $(OCH_2CH_2)_nOH$, —$CH_2O_2C(OCH_2CH_2)_nOCH_3$, and —$CH_2O_2C(OCH_2CH_2)_nOCH_2CH_3$; the myo-inosityl, scyllo-inosityl, cyclitol, conduritol A, quebrachitol, monosaccharide, disaccharide, oligosaccharide, —$CH_2$ $(OCH_2CH_2)_nOH$ and —$CH_2O_2C(OCH_2CH_2)_nOH$ being optionally substituted with one or more —$C(O)$ $C_1$–$C_{20}$ straight or branched chain alkyl, —$C(O)$ $C_2$–$C_{20}$ straight or branched chain alkenyl, —$C(O)$ $C_2$–$C_{20}$ straight or branched chain alkynyl, sulfate, or mono-, di- or tri-phosphate groups;

$R^3$ is selected from the group consisting of —$C(CH_3)$ (=$CH_2$) and —$CH(CH_3)_2$;

each n is independently an integer from 1 to 20;

D-enantiomers, L-enantiomers, and racemates thereof;

and pharmaceutically acceptable salts thereof.

Such pharmaceutically acceptable salts are known to those skilled in the art and include, but are not limited to, sodium, potassium, lithium, calcium, magnesium, zinc and iron salts.

The compounds of formula (I), including pharmaceutically acceptable salts thereof, contain at least one chiral center and therefore can exist as single enantiomers, enantiomerically enriched mixtures of enantiomers, and racemates. Accordingly, as contemplated herein, the compounds of formula (I) are useful for the treatment of neuroectodermal tumors when in their D-enantiomeric, L-enantiomeric, or racemic form.

Where $R^1$ is myo-inosityl, scyllo-inosityl, a cyclitol, conduritol A, quebrachitol, a monosaccharide, a disaccharide or an oligosaccharide, it is to be understood that such myo-inosityl, scyllo-inosityl, cyclitol, conduritol A, quebrachitol, monosaccharide, disaccharide and oligosaccharide groups can form an ether linkage with the oxygen atom to which $R^1$ is bonded. Such an ether linkage can occur between an hydroxyl group of the myo-inosityl, scyllo-inosityl, cyclitol, conduritol A, quebrachitol, monosaccharide, disaccharide or oligosaccharide and the carbon atom of the ring system to which $R^1O$— is attached; alternatively, such an ether linkage can occur between the oxygen atom of $R^1O$— and a carbon atom of the myo-inosityl, scyllo-inosityl, cyclitol, conduritol A, quebrachitol, monosaccharide, disaccharide or oligosaccharide. In addition, to the extent that the monosaccharide, disaccharide and oligosaccharide groups contain an anomeric carbon atom available for glycosidic bond formation, such an anomeric carbon can form a glycosidic bond with the oxygen atom of $R^1O$—. Furthermore, monosaccharide, disaccharide and oligosaccharide groups that contain a carboxyl group can form an ester bond between such carboxyl group and the oxygen atom of $R^1O$—.

Where $R^2$ is —$CH_2O(myo$-inosityl), —$CH_2O(scyllo$-inosityl), —$CH_2O(cyclitol)$, —$CH_2O(conduritol\ A)$, —$CH_2O(quebrachitol)$, —$CH_2O(monosaccharide)$, —$CH_2O(disaccharide)$ or —$CH_2O(oligosaccharide)$, it is to be understood that such myo-inosityl, scyllo-inosityl, cyclitol, conduritol A, quebrachitol, monosaccharide, disaccharide and oligosaccharide groups can form an ether linkage with the —$CH_2O$— oxygen atom of $R^2$. Such an ether linkage can occur between the oxygen atom of an hydroxyl group of the myo-inosityl, scyllo-inosityl, cyclitol, conduritol A, quebrachitol, monosaccharide, disaccharide or oligosaccharide, and the —$CH_2$— group of —$CH_2O(myo$-inosityl), —$CH_2O(scyllo$-inosityl), —$CH_2O(cyclitol)$, —$CH_2O(conduritol\ A)$, —$CH_2(quebrachitol)$, —$CH_2O$ (monosaccharide), —$CH_2O(disaccharide)$ or —$CH_2O$ (oligosaccharide). Alternatively, such an ether linkage can occur between the oxygen atom of —$CH_2O(myo$-inosityl), —$CH_2O(scyllo$-inosityl), —$CH_2O(cyclitol)$, —$CH_2O$ (conduritol A), —$CH_2O(quebrachitol)$, —$CH_2O$ (monosaccharide), —$CH_2O(disaccharide)$ or —$CH_2O$ (oligosaccharide), and between a carbon atom of the myo-inosityl, scyllo-inosityl, cyclitol, conduritol A, quebrachitol, monosaccharide, disaccharide or oligosaccharide. In addition, to the extent that the monosaccharide, disaccharide and oligosaccharide groups contain an anomeric carbon atom available for glycosidic bond formation, such an anomeric carbon can form a glycosidic bond with the —CH$_2$O— oxygen atom of —CH$_2$O(monosaccharide), —CH$_2$O(disaccharide) or —CH$_2$O(oligosaccharide). Furthermore, monosaccharide, disaccharide and oligosaccharide groups that contain a carboxyl group can form an ester bond between that carboxyl group and the oxygen atom of —CH$_2$O(monosaccharide), —CH$_2$O(disaccharide) or —CH$_2$O(oligosaccharide).

Suitable monosaccharides include, but are not limited to, glucose, fructose, galactose, arabinose, mannose, glucoseamine, neuraminic acid, gulose, ribose, deoxyribose, fucose, xylose, lyxose, erythrose, threose, sorbose, D- or L-enantiomers thereof and racemates thereof.

Suitable disaccharides include, but are not limited to, cellobiose, lactose, maltose, sucrose, gentiobiose, lactobionic acid, D- or L-enantiomers thereof and racemates thereof.

Suitable oligosaccharides include, but are not limited to, amylose, starch, amylopectin, cyclodextrins, chitin, chitosan, partially hydrolyzed forms thereof, D- or L-enantiomers thereof and racemates thereof.

The compounds of formula (I) can be isolated directly from natural sources, or chemically synthesized from natural or synthetic starting materials or reagents, and subsequently isolated from a reaction mixture. Either way, the compounds of formula (I) can be obtained in purified form via standard purification techniques including, but not limited to, column chromatography, recrystallization, enzymatic recovery or other means known to those skilled in the art.

D. Methods of Preparation of the Compounds

The compounds of formula (I) can be obtained via conventional organic synthesis as described below.

In general, the compounds of formula (I) can be obtained from methods described in, for example, Ohara et al., 1994, *Mokuzai Gakkaishi* 40(4):444–51 and Uvarova et al., 1980, *Carbohydrate Research* 83:33–42.

In addition, the synthesis of the compounds of formula (I) can be performed by the following methods:

Synthetic access to the compounds of formula (I) begins with betulin or betulinic acid.

During the course of a synthesis of a compound of formula (I), the $R^1$- or $R^2$-positions can be temporarily protected. Examples of suitable protecting groups include acetyl- and other acyl-protecting groups for $R^1$, and for $R^2$ in the case where $R^2$=CH$_2$OH. If —CO$_2$H is selected for $R^2$, this group can be protected in the form of any ester, for example, a methyl, ethyl or isopropyl ester. The protecting groups can be introduced by standard procedures, for example, as described in Greene and Wuts, *Protective Groups in Organic Synthesis*, (2d ed., 1991) and citations cited therein. In addition, selective protection of the $R^2$ (—CH$_2$OH) group of betulin, in the presence of the C-3 hydroxyl group, can be achieved according to the procedure described by O. Pancharoen et al., 1994, *Phytochemistry* 35(4):987–92.

To obtain compounds of formula (I) where $R^1$ forms an ether bond with the oxygen atom to which $R^1$ is attached, or where $R^2$ contains a —CH$_2$O— ether linkage, for example, where $R^1$ or $R^2$ is —C$_1$–C$_{20}$ straight or branched chain alkyl, —C$_2$–C$_{20}$ straight or branched chain alkenyl, —C$_2$–C$_{20}$ straight or branched chain alkynyl, myo-inosityl, scyllo-inosityl, cyclitol, conduritol A, quebrachitol, or chains of polyethylenglycol (—(CH$_2$CH$_2$O)$_n$H, —(CH$_2$CH$_2$O)$_n$CH$_3$ or —(CH$_2$CH$_2$O)$_n$CH$_2$CH$_3$), a linkage via an ether bond is achieved.

For this purpose, betulin or betulinic acid can react under standard ether bond-forming conditions with the —C$_1$–C$_{20}$ straight or branched chain alkyl, —C$_2$–C$_{20}$ straight or branched chain alkenyl, —C$_2$–C$_{20}$ straight or branched chain alkynyl, myo-inosityl, scyllo-inosityl, cychtol, conduritol A, quebrachitol, or polyethylenglycol (—(CH$_2$CH$_2$O)$_n$H, —(CH$_2$CH$_2$O)$_n$CH$_3$ or —(CH$_2$CH$_2$O)$_n$CH$_2$CH$_3$) chain. The —C$_1$–C$_{20}$ straight or branched chain alkyl, —C$_2$–C$_{20}$ straight or branched chain alkenyl, —C$_2$–C$_{20}$ straight or branched chain alkynyl, myo-inosityl, scyllo-inosityl, cyclitol, conduritol A, quebrachitol, or polyethylenglycol (—(CH$_2$CH$_2$O)$_n$H, —(CH$_2$CH$_2$O)$_n$CH$_3$ or —(CH$_2$CH$_2$O)$_n$CH$_2$CH$_3$) chain can be activated ad a halo, for example, chloro, bromo or iodo, derivative, or as an activated ester, for example, tosylate, triflate, mesylate or brosylate, derivative. The etherification reaction can be performed according to a standard Williamson procedure, or according to improved protocols, for example, as disclosed in R. A. W. Johnston et al., *Tetrahedron* 35:2196 (1979).

To obtain derivatives having glycosidic linkages, for example, where $R^1$ is a monosaccharide or disaccharide, or an oligosaccharide, or where $R^2$ is —CH$_2$O (monosaccharide), —CH$_2$O(disaccharide), —CH$_2$O (oligosaccharide), —CO$_2$(monosaccharide), —CO$_2$ (disaccharide), or —CO$_2$(oligosaccharide), a suitably protected derivative of either betulin or betulinic acid can react under standard glycosidic-bond forming conditions with an activated and/or suitably protected saccharide derivative.

The saccharide derivative can be linked to the C-3 oxygen atom, or to the —CH$_2$— portion of $R^2$, of the compounds of formula (I) in a stereospecific manner. Preferably, the saccharide derivative is linked to the C-3 oxygen atom, or to the —CH$_2$— portion of $R^2$, in a formation such that a β-glycosidic bond is formed. This is particularly so in case of glucose and galactose. Protocols useful for this purpose include the Koenigs Knorr procedure (W. Koenigs et al., *Ber. Dtsch. Chem. Ges.* 34:957 (1901), in which a glycosyl bromide reacts in the presence of a silver catalyst, for example, silver carbonate) and the Helferich procedure (B. Helferich et al., *Ber. Dtsch. Chem. Ges.* 73:532 (1940) and N. I. Uvarova et al. *Carbohydrate Research* 83:33–42 (1980)).

In order to obtain ester derivatives, for example, where $R^2$ is —CO$_2$(C$_1$–C$_{20}$ straight or branched chain alkyl), —CO$_2$ (C$_2$–C$_{20}$ straight or branched chain alkenyl), —CO$_2$(C$_1$–C$_{20}$ straight or branched chain alkynyl),—CO$_2$(myo-inosityl), —CO$_2$(scyllo-inosityl),—CO$_2$(cyclitol),—CO$_2$(conduritol A), —CO$_2$(quebrachitol), —CO(OCH$_2$OCH$_2$)$_n$OH, —CO (OCH$_2$OCH$_2$)$_n$OCH$_3$, and —CO(OCH$_2$OCH$_2$)$_n$OCH$_2$CH$_3$, the carboxyl group of a suitably protected—for example, via $R^1$—betulinic acid derivative has to be activated. Suitable activation betulinic acid derivatives include, but are not limited to, carboxyl halide and dicyclohexylcarbodiimide derivatives. The activated carboxylic acid derivatives can react under standard ester bond-forming conditions with a group that contains an hydroxyl function. Such a reation can be performed according to a standard Schotten-Baumann procedure or according to protocols such as disclosed in Kaiser et al., 1770, *J. Org. Chem.* 35:1198.

Derivatives of inositol, which can be used for the synthesis of ether- and ester-bond inositol derivatives of the compounds of formula (I), can be obtained by selective protection of five of the six hydroxyl functions of inositol (see, for example, Meyer zu Reckendorf, 1968, *Chem. Ber.* 101:3652–3654).

Where protection of one or both of the hydroxyl groups of betulin, or the hydroxyl group or carboxyl group of betulinic acid, is required to obtain a compound of formula (I), protection or deprotection reactions can be performed according to standard procedures, for example, as described by Greene and Wuts, *Protective Groups in Organic Synthesis* (2d ed., 1991) and citations cited therein.

In the case where acyl protecting groups are employed for $R^2$ when in the form of —$CH_2OZ$, wherein Z is the acyl protecting group, aqueous solutions of sodium hydroxide at room temperature are preferably employed for deprotection of the Z group.

Glycosyl halides, which are useful for glycosidations, and aliphatic (alkanyl, alkenyl and alkynyl) and polyethylene glycol chains, as well as halide derivatives thereof, are commercially available from standard chemical suppliers.

The compounds of formula (I) wherein $R^3$=—$CH(CH_3)_2$ can be obtained from the compounds of formula (I) wherein $R^3$=—$C(CH_3)(=CH_2)$. To obtain compounds of formula (I) wherein $R^3$=—$CH(CH_3)_2$, the compounds wherein $R^3$=—$C(CH_3)(=CH_2)$ can be catalytically hydrogenated using palladium on charcoal according to the methods described in T. Fuijoka et al., 1994, *J. Nat. Prod.* 57(2):243–47.

In addition to the above methods, the compounds of formula (I) can be obtained by conventional organic synthesis commonly known to a person skilled in the art.

Once the compounds of formula (I) have been synthesized, they can be purified or substantially purified, using conventional chromatography, recrystallization or other purification techniques known to those skilled in the art.

E. Therapeutic Indications and Methods of Treatment

One aspect of the present invention are methods and compositions for the treatment of tumors, typically neuroectodermal tumors and their metastasis, in a subject in need of such treatment. The subject is typically a mammal, and most preferably a human.

As demonstrated herein, the disclosed compounds and pharmaceutical compositions are useful for the treatment of neuroectodemial tumors, including, but not limited to, neuroblastoma, medulloblastoma, and Ewing's sarcoma. Diagnosis of neuroectodermal tumors and their metastasis is known by those skilled in the art. The methods of the invention comprise administering pharmaceutical compositions that include a therapeutically effective amount of a selected compound of the invention and an acceptable pharmaceutical carrier, see, infra, to the subject in need, i.e., a subject afflicted with a neuroectodermal tumor.

In some specific embodiments, the methods and compositions of the invention are used for the treatment of neuroectodermal tumors that are resistant to certain chemotherapeutical agents. In one such embodiment, the methods and compositions of the invention are used to treat doxorubicin resistant neuroectodermals. In another such preferred embodiment, at least one of the compositions of the invention is administrated systemically, in conjunction with other chemotherapeutical agents, such as doxorubin.

Due to the activity of the compounds of the present invention, the compounds of formula (I):

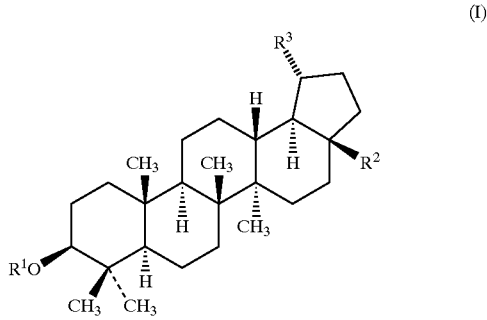

(I)

wherein $R^1$ is selected from the group consisting of hydrogen, —$(CH_2CH_2O)_nH$, —$(CH_2CH_2O)_nCH_3$, —$(CH_2CH_2O)_nCH_2CH_3$, —$C(O)C_6H_5$, —$C(O)C_1-C_{20}$ straight or branched chain alkyl, —$C(O)C_2-C_{20}$ straight or branched chain alkenyl, —$C(O)C_2-C_{20}$ straight or branched chain alkynyl, myo-inosityl, scyllo-inosityl, a monosaccharide, a disaccharide and an oligosaccharide; the —$(CH_2CH_2O)_nH$, myo-inosityl, scyllo-inosityl, monosaccharide, disaccharide and oligosaccharide being optionally substituted with one or more —$C(O)C_1-C_{20}$ straight or branched chain alkyl, —$C(O)C_2-C_{20}$ straight or branched chain alkenyl, —$C(O)C_2-C_{20}$ straight or branched chain alkynyl, sulfate, or mono-, di- or tri-phosphate groups;

$R^2$ is selected from the group consisting of —$CO_2H$, —$CO_2(C_6H_5)$, —$CO_2(C_1-C_{20}$ straight or branched chain alkyl), —$CO_2(C_2-C_{20}$ straight or branched chain alkenyl), —$CO_2(C_2-C_{20}$ straight or branched chain alkynyl), —$CO_2$(myo-inosityl), —$CO_2$(scyllo-inosityl), —$CO_2$(monosaccharide), —$CO_2$(disaccharide), —$CO_2$(oligosaccharide), —$CO(OCH_2CH_2)_nOH$, —$CO(OCH_2CH_2)_nOCH_3$, —$CO(OCH_2CH_2)_nOCH_2CH_3$, -$CH_2OH$, —$CH_2O(C_6H_5)$, —$CH_2O(C_1-C_{20}$ straight or branched chain alkyl), —$CH_2O(C_2-C_{20}$ straight or branched chain alkenyl), —$CH_2O(C_2-C_{20}$ straight or branched chain alkynyl), —$CH_2O$(myo-inosityl), —$CH_2O$(scyllo-inosityl), —$CH_2O$(monosaccharide), —$CH_2O$(disaccharide), —$CH_2O$(oligosaccharide), —$CH_2(OCH_2CH_2)_nOH$, —$CH_2(OCH_2CH_2)_nOCH_3$ and —$CH_2(OCH_2CH_2)_nOCH_2CH_3$; the myo-inosityl, scyllo-inosityl, monosaccharide, disaccharide, oligosaccharide and —$CH_2(OCH_2CH_2)_nOH$ being optionally substituted with one or more —$C(O)C_1-C_{20}$ straight or branched chain alkyl, —$C(O)C_2-C_{20}$ straight or branched chain alkenyl, —$C(O)C_2-C_{20}$ straight or branched chain alkynyl, sulfate, or mono-, di- or tri-phosphate groups;

$R^3$ is selected from the group consisting of —$C(CH_3)(=CH_2)$ and —$CH(CH_3)_2$;

each n is independently an integer from 1 to 20;

D-enantiomers, L-enantiomers, and racemates thereof; and pharmaceutically acceptable salts thereof, are advantageously useful in veterinary and human medicine for the treatment of neuroectodermal tumors.

In a preferred embodiment, the present methods comprise administering to a patient a compound of formula (I) selected from the group consisting of:

3β-3-hydroxylup-20(29)-en-28-oic acid ("betulinic acid");

3β-lup-20(29)-ene-3,28-diol ("betulin");

3β-lup-20(29)-ene-3,28-diol diacetate ("3,28-diacetylbetulin");

3β-3-(acetyloxy)lup-20(29)-en-28-oic acid ("3-acetylbetulinic acid");

3β-3-(1-oxobutoxy)lup-20(29)-en-28-oic acid ("3-butyrylbetulinic acid");

3β-3-(2,3-dihydroxycinnamoyl)lup-20(29)-en-28-oic acid ("3-(2,3-dihydroxycinnamoyl)betulinic acid");

3β-lup-20(29)-ene-3,28-diol 3-acetate ("3-acetylbetulin");

3β-lup-20(29)-ene-3,28-diol 28-acetate ("28-acetylbetulin");

3β-3-hydroxylup-20(29)-en-28-oic acid methyl ester ("methyl betulinate");

3β-3-(acetyloxy)lup-20(29)-en-28-oic acid methyl ester ("methyl 3-acetylbetulinate");

3β-3-hydroxylup-20(29)-en-28-oic acid ethyl ester ("ethyl betulinate");

3β-3-hydroxylup-20(29)-en-28-oic acid butyl ester ("butyl betulinate");

3β-lupane-3,28-diol ("dihydrobetulin");

3β-3-hydroxylupan-28-oic acid ("dihydrobetulinic acid");

3β-3-hydroxylupan-28-oic acid methyl ester ("methyl dihydrobetulinate");

3β-3-(acetyloxy)lupan-28-oic acid methyl ester ("methyl 3-acetyldihydrobetulinate");

3β-3-(acetyloxy)-lupan-28-oic acid ("3-acetyldihydro-betulinic acid");

3β-lupane-3,28-diol diacetate ("3,28-diacetyldihydrobetulin");

3β-lupane-3,28-diol dibutanoate ("3,28-dibutyryldihydrobetulin");

3β-3-(3-methyl-1-oxobutoxy)lupan-28-oic acid ("3-(3-methylbutryryl)dihydrobetulinic acid");

3β-3-((1-oxo-2-butenyl)oxy)lup-20(29)-en-28-oic acid ("3-(trans-2-butenyl)betulinic acid");

3β-3-(2,2-dimethyl-1-oxopropoxy)lupan-28-oic acid ("3-(2,2-dimethylpropionyl)dihydrobetulinic acid");

3α-28-hydroxylup-20(29)-en-3-yl-6-O-(6deoxy-α-L-mannopyranosyl)-β-D-glucopyranoside;

3α-28-hydroxylup-20(29)-en-3-yl-β-D-glucopyranoside;

3α,4α-3-(β-D-glucopyranosyloxy)lup-20(29)-en-28-oic acid;

3-(β-D-glucopyranosyloxy)lup-20(29)-en-28-oic acid;

3β-28-hydroxylup-20(29)-en-3-yl-β-D-glucopyranoside;

3β-3-hydroxylup-20(29)-en-28-yl-β-D-glucopyranoside;

3β-28(acetyloxy)lup-20(29)-en-3-yl-2-deoxy-α-D-arabinohexopyranoside triacetate;

3β-28(acetyloxy)lup-20(29)-en-3-yl-2-deoxy-β-L-arabinohexopyanoside triacetate;

3β-28(acetyloxy)lup-20(29)-en-3-yl-2,6-dideoxy-β-L-arabinohexopyranoside diacetate;

3β-3-(acetyloxy)lup-20(29)-en-28-yl-2-deoxy-α-D-arabinohexopyranoside triacetate;

3β-3-(acetyloxy)lup-20(29)-en-28-yl-2,6-dideoxy-β-L-arabinohexopyranoside diacetate;

3β-28-hydroxylup-20(29)-en-3-yl-2-deoxy-α-D-arabinohexopyranoside;

3β-28-hydroxylup-20(29)-en-3-yl-2-deoxy-β-L-arabinohexopyranoside;

3β-28-hydroxylup-20(29)-en-3-yl-2,6-dideoxy-β-L-arabinohexopyranoside;

3β-3-hydroxylup-20(29)-en-28-yl-2-deoxy-α-D-arabinohexopyranoside;

3β-lup-20(29)-en-3,28-diyl-bis-β-D-glucopyranoside;

3β-lup-20(29)-en-3,28-diyl-bis-4-O-α-D-glucopyranosyl-β-D-glucopyranoside;

3β-lup-20(29)-en-3,28-diyl-bis-(4-O-(2,3,4,6-tetra-O-acetyl-α-D-glucopyranosyl)-β-D-glucopyranoside hexaacetate;

3β-3-((4-O-α-D-glucopyranosyl-β-D-glucopyranosyl)oxy)lup-20(29)-en-28-oic acid;

3β-3-((6-O-β-D-glucopyranosyl-β-D-glucopyranosyl)oxy)lup-20(29)-en-28-oic acid;

3β-3-hydroxylup-20(29)-en-28-yl-2,6dideoxy-β-L-arabinohexopyranoside;

3β-3-((2-O-α-L-arabinopyranosyl-6-deoxy-β-D-glucopyranosyl)oxy)lup-20(29)-en-28-oic acid;

3β-3-((2-O-β-D-glucopyranosyl-β-D-glucopyranosyl)oxy)lup-20(29)-en-28-oic acid;

3β-3-hydroxylup-20(29)-en-28-oic acid 2,3,4,6-tetra-O-acetyl-β-D-glucopyranosyl ester;

3β-3-hydroxylup-20(29)-en-28-oic acid β-D-galactopyranosyl ester;

3β-3-hydroxylup-20(29)-en-28-oic acid 4-O-β-D-galactopyranosyl-β-D-glucopyranosyl ester;

3β-3-((2,3,4,6-tetra-O-acetyl-β-D-glucopyranosyl)oxy)lup-20(29)-en-28-oic acid methyl ester;

3β-3-(acetyloxy)lup-20(29)-en-28-oic acid 2,3,4,6-tetra-O-acetyl-β-D-glucopyranosyl ester;

3β-3-(acetyloxy)lup-20(29)-en-28-oic acid β-D-glucopyranosyl ester;

3β-3-((2,3,4,6-tetra-O-acetyl-β-D-glucopyranosyl)oxy)lup-20(29)-en-28-oic acid 2,3,4,6-tetra-O-acetyl-β-D-glucopyranosyl ester;

3β-3-((2,3,4,6-tetra-O-acetyl-β-D-glucopyranosyl)oxy)lupan-28-oic acid methyl ester;

3β-3-(acetyloxy)lupan-28-oic acid 2,3,4,6-tetra-O-acetyl-β-D-glucopyranosyl ester;

3α-3-((2,3,4,6-tetra-O-acetyl-β-D-glucopyranosyl)oxy)lup-20(29)-en-28-oic acid;

3β-3-((2,3,4,6-tetra-O-acetyl-β-D-glucopyranosyl)oxy)lup-20(29)-en-28-oic acid;

3β-3-(acetyloxy)lupan-28-oic acid β-D-glucopyranosyl ester;

3β-3-hydroxylup-20(29)-en-28-oic acid β-D-glucopyranosyl ester;

3β-3-hydroxylup-20(29)-en-28-oic acid β-D-xylopyranosyl ester;

3β-hydroxylup-20(29)-en-28-oic acid β-D-glucopyranosyl ester 2',3',4',6'-tetrabenzoate;

3β-lup-20(29)-en-28-oic acid (β-D-glucopyranosyloxy)-β-D-glucopyranosyl ester octabenzoate;

3β-lup-20(29)-en-28-oic acid (α-L-arabinopyranosyloxy)-α-L-arabinopyranosyl ester;

3β-lup-20(29)-en-28-oic acid (α-L-arabinopyranosyloxy)-α-L-arabinopyranosyl ester hexabenzoate;

3β-3-(β-D-glucopyranosyloxy)lup-20(29)-en-28-oic acid methyl ester;

3β-3-(β-D-glucopyranosyloxy)lupan-28-oic acid methyl ester;

3β-3-hydroxylupan-28-oic acid β-D-glucopyranosyl ester;

3β-17-carboxy-28-norlup-20(29)-en-3-yl-3-O-β-D-xylopyranosyl-β-D-glucopyranosiduronic acid;

3β-17-carboxy-28-norlup-20(29)-en-3-yl-2-O-β-D-xylopyranosyl-β-D-glucopyranosiduronic acid;

3β-3-(β-D-glucopyranosyloxy)lup-20(29)-en-28-oic acid 6-O-β-D-glucopyranosyl-β-D-glucopyranosyl ester, 3α-3-hydroxylup-20(29)-en-28-oic acid O-6-deoxy-α-L-mannopyranosyl-(1→4)-O-β-D-glucopyranosyl-(1→6)-O-β-D-glucopyranosyl ester;

3α-3-(β-D-glucopyranosyloxy)lup-20(29)-en-28-oic acid O-6-deoxy-α-L-mannopyranosyl-(1→4)-O-β-D-glucopyranosyl-(1→6)-O-β-D-glucopyranosyl ester;

3β-3-(β-D-glucopyranosyloxy)lup-20(29)-en-28-oic acid O-6-deoxy-α-L-mannopyranosyl-(1→4)-O-β-D-glucopyranosyl-(1→6)-O-β-D-glucopyranosyl ester;

3β-28-methoxy-28-oxolup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid methyl ester diacetate;

3β-17-carboxy-28-norlup-20(29)-en-3-yl-O-6-deoxy-α-L-mannopyranosyl-(1→2)-O-β-D-glucopyranosyl-(1→2)-β-D-glucopyranosiduronic acid;

3β-17-carboxy-28-norlup-20(29)-en-3-yl-O-6-deoxy-α-L-mannopyranosyl-(1 →)-O-β-D-xylopyranosyl-(1→2)-β-D-glucopyranosiduronic acid;

3β-17-carboxy-28-norlup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→)-β-D-glucopyranosiduronic acid diacetate;

3β-17-carboxy-28-norlup-20(29)-en-3-yl-O-2,3,4-tri-O-acetyl-6-deoxy-α-L-mannopyranosyl-(1→2)-O-3,4-di-O-acetyl-β-D-xylopyranosyl-(1→2)-β-D-glucopyranosiduronic acid diacetate;

3β-28-methoxy-28-oxolup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid methyl ester diacetate;

3β-28-methoxy-28-oxolup-20(29)-en-3-yl-O-2,3,4-tri-O-acetyl-6-deoxy-α-L-mannopyranosyl-(1→2)-O-3,4-di-O-acetyl-β-D-xylopyranosyl-(1→2)-β-D-glucopyranosiduronic acid methyl ester diacetate;

3β-3-((O-α-L-arabinofiranosyl-(1→2)-O-6-deoxy-α-L-mannopyranosyl-(1→4)-β-D-glucopyranosyl)oxy)-lup-20(29)-en-28-oic acid;

3β-3-((O-α-L-arabinofiiranosyl-(1→2)-O-6-deoxy-α-L-mannopyranosyl-(1→4)-β-D-glucopyranosyl)oxy)-lup-20(29)-en-28-oic acid methyl ester;

3β-28-hydroxylup-20(29)-en-3-yl-4-O-β-D-glucopyranosyl-β-D-glucopyranoside;

3β-28-hydroxylup-20(29)-en-3-yl-4-O-α-D-glucopyranosyl-β-D-glucopyranoside;

3β-3-hydroxylup-20(29)-en-28-yl-4-O-α-D-glucopyranosyl-β-D-glucopyranoside;

3β-28-hydroxylup-20(29)-en-3-yl-β-D-xylopyranoside;

3-(β-D-glucopyranosyloxy)lup-20(29)-en-28-oic acid O-6-deoxy-β-L-mannopyranosyl-(1→4)-O-β-D-glucopyranosyl-(1→6)-O-β-D-glucopyranosyl ester;

3α-lup-20(29)-en-28-oic acid 3-(β-D-glucopyranosyloxy)-O-6-deoxy-α-L-mannopyranosyl-(1→4)-O-β-D-glucopyranosyl-(1→6)-O-β-D-glucopyranosyl ester;

3α-4-α-3-(β-D-glucopyranosyloxy)lup-20(29)-en-28-oic acid;

3α-lup-20(29)-en-28-oic acid 3-((O-6-acetyl-β-D-glucopyranosyl)oxy)-O-6-deoxy-α-L-mannopyranosyl-1-(1→4)-O-β-D-glucopyranosyl-(1→6)-O-β-D-glucopyranosyl ester;

3β-28-hydroxylup-20(29)-en-3-yl-O-α-D-glucopyranosyl-(1→4)-O-α-D-glucopyranosyl-(1→4)-O-β-D-glucopyranosyl-(1→4)-β-D-glucopyranoside;

3α-3-(sulfooxy)lup-20(29)-en-28-oic acid 28-O-6-deoxy-α-L-mannopyranosyl-(1→4)-O-β-D-glucopyranosyl-(1→6)-β-D-glucopyranosyl ester;

3-(sulfooxy)lup-20(29)-en-28-oic acid 28-(O-2,3,4-tri-O-acetyl-6-deoxy-α-L-mannopyranosyl-(1→4)-O-2,3,6-tri-O-acetyl-β-D-glucopyranosyl-(1→6)-2,3,4-tri-O-acetyl-β-D-glucopyranosyl) ester;

3α-3-(acetyloxy)lup-20(29)-en-28-oic acid O-2,3,4-tri-O-acetyl-6-deoxy-α-L-mannopyranosyl-(1→4)-O-2,3,6-tri-O-acetyl-β-D-glucopyranosyl-(1→6)-2,3,4-tri-O-acetyl-β-D-glucopyranosyl) ester;

28-(acetyloxy)lup-20(29)-en-3-yl-4-O-(2,3,4,6-tetra-O-acetyl-α-D-glucopyranosyl)-β-D-glucopyranoside triacetate;

3β-28-(acetyloxy)lup-20(29)-en-3-yl-4-O-(2,3,4,6-tetra-O-acetyl-β-D-glucopyranosyl)-β-D-glucopyranoside triacetate;

3β-3-(acetyloxy)lup-20(29)-en-28-yl-4-O-(2,3,4,6-tetra-O-acetyl-α-D-glucopyranosyl)-β-D-glucopyranoside triacetate;

3β-3-((2,3,4,6-tetra-acetyl-βp-D-glucopyranosyl)oxy)lup-20(29)-en-28-yl-β-D-glucopyranoside tetraacetate;

3β-28-(acetyloxy)lup-20(29)-en-3-yl-β-D-glucopyranoside tetraacetate;

3β-3-(acetyloxy)lup-20(29)-en-28-yl-β-D-glucopyranoside tetraacetate;

3β-lup-20(29)-en-3-yl-β-D-glucopyranoside tetraacetate;

3β-lup-20(29)-en-3-yl-6-deoxy-α-L-mannopyranoside;

3β-3-((6-deoxy-2-O-β-D-glucopyranosyl-α-L-mannopyranosyl)oxy)lup-20(29)-en-28-oic acid;

3β-3-((6-deoxy-α-L-mannopyranosyl)oxy)lup-20(29)-en-28-oic acid;

3β-lup-20(29)-en-3-yl-4-O-β-D-xylopyranosyl-β-D-glucopyranoside;

3β-28-(acetyloxy)lup-20(29)-en-3-yl-α-D-glucopyranoside tetraacetate;

3β-3-hydroxylup-20(29)-en-28-yl-β-D-glucopyranoside 2,3,4,6-tetraacetate;

3β-28-((6-O-D-apio-β-D-furanosyl-β-D-glucopyranosyl)oxy)-28-oxolup-20(29)-en-3-yl-4-O-β-D-galactopyranosyl-β-D-glucopyranosiduronic acid;

3β-3-((2-propenyl)oxy)lup-20(29)-en-28-oic acid ("3-O-allylbetulinic acid");

3β-3,28-dimethoxylup-20(29)-ene ("3,28-di-O-methylbetulin");

3β-3,28-dimethoxylupane ("3,28-di-O-methyldihydrobetulin");

3β-28-methoxylupan-3-ol ("28-methyldihydrobetulin");

3β-3-methoxylup-20(29)-en-28-oic acid ("3-O-methylbetulinic acid");

3β-3-methoxylup-20(29)-en-28-oic acid methyl ester ("methyl 3-O-methylbetulinate");

8ξ-2,6-anhydro-9-O-((3β,18β)-17-carboxy-28-norlupan-3-yl)1,7,8-trideoxy-8methyl-3,4,5-tris-O-(phenylmethyl)-L-glycero-D-galactononitol;

2,6-anhydro-9-O-((3β,18β)-17-carboxy-28-norlup-20(29)-en-3-yl)-1,7,8-trideoxy-methylene-3,4,5-tris-O-(phenylmethyl)-L-glycero-D-galactononitol;

3α-3-methoxylup-20(29)-en-28-oic acid;

3α-3-methoxylup-20(29)-en-28-oic acid methyl ester;

3β-28-(acetyloxy)lup-20(29)-en-3-yl-β-D-glucopyranoside ("28-acetyl-3-β-D-glucosylbetulin");

3β-28-(acetyloxy)lup-20(29)-en-3-yl-β-D-galactopyranoside ("28-acetyl-3-β-D-galactosylbetulin"); and 3β-3-(acetyloxy)lup-20(29)-en-28-yl-β-D-glucopyranoside ("3-acetyl-28-β-D-glucosylbetulin"), a D-enantiomer, L-enantiomer or racemate thereof, or a pharmaceutically acceptable salt thereof.

In particular, the compounds of formula (I), betulinic acid, 28-acetyl-3-β-D-glucosyl betulin ("B10"), 3-β-28-hydroxylup-20(29)-en-3-yl-β-3-D-glucopyranoside ("B11"), 3-β-3-hydroxylup-20(29)-en-28-yl-β-D-glucopyranoside ("B12"), and 3-(β-D-glucopyranosyloxy) lup20(29)-en-28-oic acid ("B13"), or acceptable alts thereof, have been demonstrated to have high efficacy in activating apoptosis in tumor cells.

When administered to a patient, e.g., a mammal for veterinary use or to a human for clinical use, the compounds of formula (I) are preferably administered in isolated form. By "isolated" is meant that prior to formulation in a composition, the compounds of formula (I) are separated from other components of either (a) a natural source such as a plant or cell culture, or (b) a synthetic organic chemical reaction mixture. Preferably, via conventional techniques, the compounds of formula (I) are purified.

For successful treatment of indictations involving tumors in the brain, such as primary medulloblastoma, primary neuroblastoma or Ewing's sarcoma, the active compound may need to be capable to pass the blood/brain barrier, depending on how intact the blood/brain barrier is in a given case. Generally, small lipophilic compounds, such as betulinic acid and the disclosed derivatives, are well suited to passively pass the blood/brain barrier. However, of particular value may be compounds that have sugar residues, such as in particular glucose residues as they may pass the blood/brain barrier actively, through saccharide receptors and channels, in particular glucose channels. Therefore, compounds including 28-acetyl-3-β-D-glucosyl betulin ("B10"), 3-β-28-hydroxylup-20(29)-en-3-yl-β-D-glucopyranoside ("B11"), 3-β-3-hydroxylup-20(29)-en-28-yl-β-D-glucopyranoside ("B12"), and 3-(β-D-glucopyranosyloxy)lup-20(29)-en-28-oic acid ("B13") may be particularly advantageous for the treatment of tumors located in the brain.

When administered to a patient, e.g., a mammal for veterinary use or to a human for clinical use, the compounds of formula (I) can be used alone or in combination with any physiologically acceptable carrier or vehicle suitable for enteral or parenteral administration. Where used for parenteral administration, the physiologically acceptable carrier or vehicle should be sterile and suitable for in vivo use in a human, or for use in a veterinary clinical situation.

F. Formulations and Routes of Administration

The compounds described herein, or pharmaceutically acceptable addition salts or hydrates thereof, can be delivered to a patient using a wide variety of routes or modes of administration. Suitable routes of administration include, but are not limited to, inhalation, transdermal, oral, rectal, transmucosal, intestinal and parenteral administration, including intramuscular, subcutaneous and intravenous injections.

The compounds described herein, or pharmaceutically acceptable salts and/or hydrates thereof, may be administered singly, in combination with other compounds of the invention, and/or in cocktails combined with other therapeutic agents. Of course, the choice of therapeutic agents that can be co-administered with the compounds of the invention will depend, in part, on the condition being treated.

For example, when administered to patients suffering neuroectodermal tumors or drug resistant tumors, the compounds of the invention can be administered in cocktails containing agents used to treat the pain, infection and other symptoms and side effects commonly associated with such tumors. Such agents include, e.g., analgesics, antibiotics, etc. The compounds can also be administered in cocktails containing other agents that are commonly used to treat neuroectodermal tumors, such as vincristine, doxorubicin (or dactinomycin), and cyclophosphamide. Grier et al, 1994, *Proceedings of the American Society of Clinical Oncology* 13: A-1443, 421.

When administered to a patient undergoing cancer treatment, the compounds may be administered in cocktails containing other anti-cancer agents and/or supplementary potentiating agents. The compounds may also be administered in cocktails containing agents that treat the side-effects of radiation therapy, such as anti-emetics, radiation protectants, etc.

Anti-cancer drugs that can be co-administered with the compounds of the invention also include, e.g., Aminoglutethimide; Asparaginase; Bleomycin; Busulfan; Carboplatin; Carmustine (BCNU); Chlorambucil; Cisplatin (cis-DDP); Cyclophosphamide; Cytarabine HCl; Dacarbazine; Dactinomycin; Daunorubicin HCl; Doxorubicin HCl; Estramustine phosphate sodium; Etoposide (VP-16); Floxuridine; Fluorouracil (5-FU); Flutamide; Hydroxyurea (hydroxycarbamide); Ifosfamide; Interferon Alfa-2a, Alfa 2b, Lueprolide acetate (LHRH-releasing factor analogue); Lomustine (CCNU); Mechlorethamine HCl (nitrogen mustard); Melphalan; Mercaptopurine; Mesna; Methotrexate (MTX); Mitomycin; Mitotane (o.p'-DDD); Mitoxantrone HCl; Octreotide; Plicamycin; Procarbazine HCl; Streptozocin; Tamoxifen citrate; Thioguanine; Thiotepa; Vinblastine sulfate; Vincristine sulfate; Amsacrine (m-AMSA); Azacitidine; Hexamethylmelamine (HMM); Interleukin 2; Mitoguazone (methyl-GAG; methyl glyoxal bisguanylhydrazone; MGBG); Pentostatin; Semustine (methyl-CCNU); Teniposide (VM-26); paclitaxel and other taxanes; and Vindesine sulfate.

Supplementary potentiating agents that can be co-administered with the compounds of the invention include, e.g., Tricyclic anti-depressant drugs (e.g., imipramine, desipramine, amitriptyline, clomipramine, trimipramine, doxepin, nortriptyline, protriptyline, amoxapine and maprotiline); non-tricyclic and anti-depressant drugs (e.g., sertraline, trazodone and citalopram); $Ca^{++}$ antagonists (e.g., verapamil, nifedipine, nitrendipine and caroverine); Amphotericin (e.g., Tween 80 and perhexiline maleate); Triparanol analogues (e.g., tamoxifen); antiarrhythmic drugs (e.g., quinidine); antihypertensive drugs (e.g., reserpine); Thiol depleters (e.g., buthionine and sulfoximine); and calcium leucovorin.

The active compound(s) may be administered per se or in the form of a pharmaceutical composition wherein the active compound(s) is in admixture with one or more pharmaceutically acceptable carriers, excipients or diluents. Pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compound(s) with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethylcellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation or transcutaneous delivery (for example subcutaneously or intramuscularly), intramuscular injection or a transdermal patch. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols

G. Effective Dosages

Pharmaceutical compositions suitable for use with the present invention include compositions wherein the active ingredient is contained in a therapeutically effective amount, i.e., in an amount effective to achieve its intended purpose. Of course, the actual amount effective for a particular application will depend, inter alia, on the condition being treated. For example, when administered in methods to induce apoptosis in neuroectodermal tumors such compositions will contain an amount of active ingredient effective to achieve this result. When administered in methods to inhibit the growth of tumor cells lacking p53, such compositions will contain an amount of active ingredient effective to achieve this result. When administered to patients suffering from neuroectodermal tumors, such compositions will contain an amount of active ingredient effective to, inter alia, prevent the development of or alleviate the existing symptoms of, or prolong the survival of, the patient being treated. For use in the treatment of cancer that are resistant to other drugs, a therapeutically effective amount further includes that amount of compound or composition which arrests or regresses the growth of a tumor. Determination of an effective amount is well within the capabilities of those skilled in the art, especially in light of the detailed disclosure herein.

For any compound described herein, the therapeutically effective amount can be initially determined from cell culture arrays. Target plasma concentrations will be those concentrations of active compound(s) that are capable of inducing at least about 25% apoptosis and/or at least about 25% inhibition of cell proliferation in cell culture assays, depending, of course, on the particular desired application. Target plasma concentrations of active compound(s) that are capable of inducing at least about 50%, 75%, or even 90% or higher induction of apoptosis inhibition of cell proliferation in cell culture assays are preferred. The percentage of induction of apoptosis or inhibition of cell proliferation in the patient can be monitored to assess the appropriateness of the plasma drug concentration achieved.

Therapeutically effective amounts for use in humans can also be determined from animal models. For example, a dose for humans can be formulated to achieve a circulating concentration that has been found to be effective in animals. Useful animal models for diseases characterized by abnormal cell proliferation are well-known in the art. In particular, the following references provide suitable animal models for cancer xenografts (Corbett et al, 1996, *J. Exp. Ther. Oncol.* 1:95–108; Dykes et aL, 1992, *Contrib. Oncol. Basel. Karger* 42:1–22), restenosis (Carter et al., 1994, *J. Am. Coll. Cardiol.* 24(5):1398–1405), atherosclerosis (Zhu et al, 1994, *Cardiology* 85(6):370–377) and neovascularization (Epstein et al., 1987, *Cornea* 6(4):250–257). The dosage in humans can be adjusted by monitoring the size of tumors.

A therapeutically effective dose can also be determined from human data for compounds which are known to exhibit similar pharmacological activities, such as doxorubicin (see, eg., Brugnara et al., 1995, *JPET* 273:266–272; Benzaquen et al, 1995, *Nature Medicine* 1:534–540; Brugnara et al., 1996, *J. Clin. Invest.* 97(5):1227–1234). The applied dose can be adjusted based on the relative bioavailability and potency of the administered compound as compared with doxorubicin.

Adjusting the dose to achieve maximal efficacy in humans based on the methods described above and other methods as are well-known in the art is well within the capabilities of the ordinarily skilled artisan.

Of course, in the case of local administration, the systemic circulating concentration of administered compound will not be of particular importance. In such instances, the compound is administered so as to achieve a concentration at the local area effective to achieve the intended result.

For use in the prophylaxis and/or treatment of neuroectodermal tumors, a circulating concentration of administered compound of about 0.001 $\mu$M to 20 $\mu$M is considered to be effective, with about 0.1 $\mu$M to 5 $\mu$M being preferred.

Patient doses for oral administration of the compounds described herein, which is the preferred mode of administration for treatment of neuroectodermal tumors, typically range from about 80 mg/day to 16,000 mg/day, more typically from about 800 mg/day to 8000 mg/day, and most typically from about 800 mg/day to 4000 mg/day. Stated in terms of patient body weight, typical dosages range from about 1 to 200 mg/kg/day, more typically from about 10 to 100 mg/kg/day, and most typically from about 10 to 50 mg/kg/day. Stated in terms of patient body surface areas, typical dosages range from about 40 to 8000 mg/m$^2$/day, more typically from about 400 to 4000 mg/m$^2$/day, and most typically from about 400 to 2000 mg/m$^2$/day.

For use in the treatment of tumors characterized by being resistant to other chemotherapeutic agents, including tumors lacking p53 wild type proteins or having defects in the CD95 system, a circulating concentration of administered compound of about 0.001 $\mu$M to 20 $\mu$M is considered to be effective, with about 0.1 $\mu$M to 5 $\mu$M being preferred.

Patient doses for oral administration of the compounds described herein for the treatment or prevention of cancers typically range from about 80 mg/day to 16,000 mg/day, more typically from about 800 mg/day to 8000 mg/day, and most typically from about 800 mg/day to 4000 mg/day. Stated in terms of patient body weight, typical dosages range from about 1 to 200 mg/kg/day, more typically from about 10 to 100 mg/kg/day, and most typically from about 10 to 50 mg/kg/day. Stated in terms of patient body surface areas, typical dosages range from about 40 to 8000 mg/m$^2$/day, more typically from about 400 to 4000 mg/m$^2$/day, and most typically from about 400 to 2000 mg/m$^2$/day.

For other modes of administration, dosage amount and interval can be adjusted individually to provide plasma levels of the administered compound effective for the particular clinical indication being treated. For use in the treatment of tumorigenic cancers, the compounds can be administered before, during or after surgical removal of the tumor. For example, the compounds can be administered to the tumor via injection into the tumor mass prior to surgery in a single or several doses. The tumor, or as much as possible of the tumor, may then be removed surgically. Further dosages of the drug at the tumor site can be applied post removal. Alternatively, surgical removal of as much as possible of the tumor can precede administration of the compounds at the tumor site.

Combined with the teachings provided herein, by choosing among the various active compounds and weighing factors such as potency, relative bioavailability, patient body weight, severity of adverse side-effects and preferred mode of administration, an effective prophylactic or therapeutic treatment regimen can be planned which does not cause substantial toxicity and yet is entirely effective to treat the clinical symptoms demonstrated by the particular patient. Of course, many factors are important in determining a therapeutic regimen suitable for a particular indication or patient. Severe indications warrant administration of higher dosages as compared with less severe indications.

H. Toxicity

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds which exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al, 1975, In: *The Pharmacological Basis of Therapeutics*, Ch. 1 p1).

I. Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition. Suitable conditions indicated on the label may include the treatment of neuroectodermal tumors, medulloblastoma, neuroblastoma, Ewing's sarcoma, and the like.

The following examples for the generation and use of the selection systems of the invention are given to enable those skilled in the art to more clearly understand and to practice the present invention. Some materials in the following examples have been published in Fulda et al, 1997, *Cancer Res.* 57:4956–4964 and Fulda et al., 1998, *Cancer Res.* 58:4453–4460, incorporated herein by reference for all purposes. The present invention, however, is not limited in scope by the exemplified embodiments, which are intended as illustrations of single aspects of the invention only, and methods which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims.

VI. EXAMPLES

A. Example 1

Synthesis of Compounds of Formula I
28-Acetyl-3-β-D-glucosylbetulin

1 Eq. of betulin was treated with an excess of acetic anhydride in pyridine solvent, at room temperature, and for 12 hours, to afford 3,28-diacetylbetulin. 1 Eq. of 3,28-diacetylbetulin was treated with 1 eq. of NaOH in ethanol to afford 28-acetylbetulin in 61% yield. 28-Acetylbetulin was obtained according to the procedure of S. Ohara et al., *Mokuzai Gakkaishi* 40(4):4444–51 (1994). Specifically, 1 eq. of 28-acetylbetulin was treated with 3 eq. of 2,3,4,6-tetraacetyl-α-D-glucopyranosyl bromide in the presence of excess $Hg(CN)_2$, and in nitromethane solvent, to afford a crude reaction product that was purified via column chromatography to provide 28-acetyl-3-β-D-(2,3,4,6-tetraacetyl) glucosylbetulin in 62% yield. 1 Eq. of the 28-acetyl-3-β-D-(2,3,4,6-tetraacetyl)glucosylbetulin so obtained was then treated with an excess of a 4:2:1 mixture of $MeOH:H_2O:Et_3N$ at 40–50° C. for 1 h to afford the above-titled compound in 62% yield.

28-Acetyl-3-β-D-galactosylbetulin

28-Acetyl-3-β-D-galactosylbetulin was prepared according to the procedure of Example 1, above, except that 2,3,4,6-tetraacetyl-α-D-galactopyranosyl bromide was used in place of 2,3,4,6-tetraacetyl-α-D-glucopyranosyl bromide, and that 28-acetyl-3-β-D-galactosylbetulin was not purified from its reaction mixture.

3-Acetyl-28-β-D-glucosybetulin

1 Eq. of betulin is treated with an excess of acetic anhydride in pyridine solvent, at 0° C., for 0.5 to 1 h, or until thin layer chromatography indicates that the reaction is complete, to afford 3-acetylbetulin.

1 Eq. of β-D-Glucose is treated with excess trichloroacetyl chloride in the presence of pyridine solvent to afford a mixture of pertrichloroacetyl-α-D-glucose and pertrichloroacetyl-β-D-glucose. 1 Eq. of the mixture of pertrichloroacetyl-β-D-glucose and pertrichloroacetyl-β-D-glucose so obtained is treated with HBr in acetic acid solvent to afford 2,3,4,6-tetratrichloroacetyl-α-D-glucopyranosyl bromide.

1 Eq. of 3-acetylbetulin is treated with an excess of 2,3,4,6-tetratrichloroacetyl-α-D-glucopyranosyl bromide in the presence of excess $Hg(CN)_2$, and in nitromethane solvent, to afford a crude reaction product that is purified via column chromatography to provide 3-acetyl-3-acetyl-28-β-D-(2,3,4,6-tetratrichloroacetyl)glucosylbetulin. 1 Eq. of 3-acetyl-28-β-D-(2,3,4,6-tetratrichloroacetyl) glucosylbetulin is then treated with $NH_3/EtOH$ in chloroform solvent (V. Schwarz, *Coll. Czech. Commun.* 27:2567 (1962)) to afford the above-titled compound.

B. Example 2

Betuilnic Acid Induces Apoptosis in Neuroectodermal Cells

This example illustrates that betulinic acid induces apoptosis in neuroectodermal tumors, such as neuroblastoma, medulloblastoma, and Ewing's sarcoma, representing the most common solid tumors of childhood. This example also shows that betulinic acid triggered an apoptosis pathway different from the one previously identified for standard chemotherapeutic drugs. Betulinic acid-induced apoptosis was independent of CD95-ligand/receptor interaction and accumulation of wild-type p53 protein, but it critically depended on activation of caspases (interleukin 1β-converting enzyme/Ced-3-like proteases). FLICE/MACH (caspase-8), considered to be an upstream protease in the caspase cascade, and the downstream caspase CPP32/YAMA/A popain (caspase-3) were activated, resulting in cleavage of the prototype substrate of caspases PARP. The broad-spectrum peptide inhibitor benzyloxycarbonyl-Val-Ala-Asp-Fluoromethylketone, which blocked cleavage of FLICE and PARP, also completely abrogated betulinic acid-triggered apoptosis. Cleavage of caspases was preceded by disturbance of mitochondrial membrane potential and by generation of reactive oxygen species. Overexpression of Bcl-2 and Bcl-$x_L$ conferred resistance to beutilinic acid at the level of mitochondrial dysfunction, protease activation, and nuclear fragmentation. This suggested that mitochondrial alterations were involved in betulinic acid-induced activation of caspases. Furthermore, Bax and Bcl-$x_m$, two death-promoting proteins of the Bcl-2 family, were up-regulated following betulinic acid treatment. Most importantly, neuroblastoma cells resistant to CD95- and doxorubicin-mediated apoptosis were sensitive to treatment with betulinic acid, suggesting that betulinic acid may bypass some forms of drug resistance. Betulinic acid also induces apoptosis in neuroectodermal cells derived from patient ex vivo, which indicates that betulinic acid should be active in vivo.

1. Materials And Methods

Drugs

Betulinic acid (Aldrich; Steinheim, Germany) and doxorubicin (Farmitalia, Milan, Italy) were provided as pure substances and dissolved in DMSO (4 mg/ml betulinic acid) or sterile water (1 mg/ml doxorubicin) before each experiment.

Cell Culture

Neuroblastoma (SH-EP, IMR-32, Kelly, and LAN-5, kindly provided by Professor M. Schwab, German Cancer Research Center, Heidelberg, Germany), medulloblastoma cells (Daoy, kindly provided by Dr. T. Pietsch, Department of Neuropathology, University of Bonn Medical Center, Bonn, Germany), Ewing's sarcoma cells (A17/95, kindly provided by Dr. U. Anderer, Institute of Pathology, Humboldt University, Berlin, Germany), melanoma (A-378), breast carcinoma (MCF-71), colon carcinoma (HT-29), small cell lung carcinoma (H-126), renal cell carcinoma (KTCTL-26, kindly provided by H. Lörke, German Cancer Research Center, Heidelberg, Germany) and T-cell leukemia (CEM) cells were cultured in RPMI 1640 (Life Technologies, Inc., Eggenstein, Germany) supplemented with 10% heat-inactivated fetal bovin serum (FCS) from Conco. (Wiesbaden, Germany), 10 mM HEPES, pH 7.3 (Biochrom, Berlin, Germany), 100 units/ml penicillin (Life Technologies, Inc.), 100 μg/ml streptomycin (Life Technologies, Inc.), and 2 mM L-glutamine (Biochrom, Berlin, Germany). SH-EP neuroblastoma cells stably transfected with bcl-2, bcl-$X_L$, or vector control were cultured in Dulbecco's minimal Eagle's medium (Life Technologies, Inc.) containing 500 μg/ml G418 (Geneticin, Life Technologies, Inc.) as described in Dole et al., 1994, *Cancer Res.* 54: 3253–3259 and Dole et al., 1995, *Cancer Res.* 55: 2576–2582. SH-EP$^{CD95R}$ and SH-EP$^{DoxoR}$ cells, variants of SH-EP neuroblastoma cells resistant to anti-CD95 and doxorubicin, respectively, were generated by continuous culture in the presence of the agonistic anti-APO-1 (anti-CD95) antibody (1 μg/ml; Trauth et al, 1989, *Science* (Washington D.C.). 245: 301–305.) or doxorubicin (0.1 μg/ml) for more than 6 months. For experiments, resistant cells were washed and cultured in medium without anti-APO-1 (anti-CD95) for 24 h or without doxorubicin for 2 weeks.

Determination of Apoptosis

Quantification of DNA fragmentation was performed by FACS analysis of propidium iodide stained nuclei as described in Nicoletti et al, 1991, *J. Immunol. Methods.* 139: 271–279. Cells were analyzed for DNA content by flow. cytometry (FACScan, Becton Dickinson, Heidelberg, Germany) using CELLQuest software. Early apoptotic changes were identified by staining with biotinylated annexin V (Bender Med Systems, Vienna, Austria) following the manufacturer's instructions. Annexin V binds to exposed phosphatidylserine on the surface of apoptotic cells. Koopman et al, 1994, *Blood.* 84:1415–1420. Cells were analyzed by flow cytometry (FAC-Scan. Becton Dickinson) using CELLQuest software.

Preparation of Neuroblastoma Tumor Samples

Fresh tumor samples from two patients with neuroblastoma stages IV5 and IV, respectively, were obtained from surgical resections prior to chemotherapy and immediately analyzed. Single-cell suspensions were prepared using DNase (0.154 mg/ml), collagenase (0.416 mg/ml), and hyaluronidase (0.33 mg/ml; Boehringer Mannheim). Two-color fluorescence using FITC-conjugated mouse antihuman GD2 antibody (IgG2a. 0.2 mg/ml, kindly provided by R. Handgretinger, University of Tuebingen, Tuebingen, Germany) and biotinylated annexin V (Bender Med Systems) followed by streptavidin-phycoerythrin was performed to detect apoptotic neuroblastoma cells. Wu et al., 1986, *Cancer Res.* 46:440–443.

Incubation with Tripeptide Inhibitor of Caspases or F(ab')$_2$ Anti-APO-1 (Anti-CD95); Antibody Fragments The broad range tripeptide inhibitor of caspases $_2$VAD-tmk (Enzyme Systems Products, Dublin, CA) was used at a concentration of 60 μm. Preparation of F(ab')$_2$ anti-APO-1 (anti-CD95) antibody fragments and isotype-matched antibody F1123 (1gG3) were performed as described in Dhein et al., 1995, *Nature (Lond.)* 375: 81–83. Cells were incubated with 10 μg/ml F(ab')$_2$ anti-APO-1 antibody fragments or 10 μg/ml F(ab')$_2$ F1123 antibody fragments for 1 h at 37° C. prior to addition of betulinic acid.

Determination of Caspase Activity

Caspase activity was measured by FACS analysis as described in Los et al., 1995, *Nature (Lond.)* 375:81–83. Briefly, cells were loaded in hypotonic medium with the fluorogenic substrate Val-Ala-Asp-[2(4-methoxynaphthylamide)] at a final concentration of 50 μm (Enzyme Systems Products). Fluorescence was measured by flow cytometer (FACVantage, Becton Dickinson) using an excitation wavelength of 365 nm and an emission wavelength of 425 nm.

Assessment of Mitochondrial Potential, Intracellular Peroxides and Membrane Peroxidation The cationic lipophilic fluorochrome DiOC$_6$(3)(460 ng/ml, Molecular Probes, Eugene, Oreg.) was used to measure the ΔΨ$_m$. HE(126 ng/ml. Molecular probes) was used to determine ROS generation, and NAO (94 ng/ml, Molecular Probes) was used to determine lipid peroxidation. Kroemer et al, 1997, *Immunol. Today.* 18:44–51. Cells were incubated for 12 min at 37° C. in the presence of the fluorochromes, washed in PBS/1% FCS, and immediately analyzed by flow cytometry (FACScan, Becton Dickinson). DiOC$_6$(3) and NAO fluorescence were recorded in fluorescence 1; He fluorescence was assessed in fluorescence 3. The percentage of cells with low mitochondrial potential or enhanced ROS production was calculated in comparison to untreated control cells.

RT-PCR for CD95-L mRNA

Total RNA was prepared using the Qiagen total RNA kit (Qiagen, Hilden, Germany). RNA was converted to cDNA by reverse transcription and amplified for 38 cycles by PCR in a thermocycler (Stratagene, Heidelberg, Germany) using the Gene Amplification RNA-PCR kit (Perkin-Elmer, Branchburg, N.J.) following the manufacturer's instructions. Primers used for amplification of the CD95-L fragment are according to the sequence of human CD95-L (Suda et al., 1995, Cell 75:1169–1178; Herr et al., 1996, Cell Death Diff., 5:299–305). Expression of β-actin (MWG-Biotech, Ebersberg, Germany) was used as an internal standard for RNA integrity and equal gel loading. PCR products were run at 60 V for 2 h on a 1.5% agarose gel stained with ethidium bromide and visualized by UV illumination.

Western Blot Analysis

Cells were lysed for 30 min at 4° C. in PBS with 0.5% Triton X (Serva, Heidelberg, Germany) and 1 mM phenylmethylsulfonyl fluoride (Sigma, Deisenhofen, Germany) followed by high-speed centrifugation. Membrane proteins were eluted in buffer containing 0.1 M glycine. PH 3.0 and 1.5 M Tris, pH 8.8. Protein concentration was assayed using bicinchoninic acid (Pierce Chemical Co., Rockford, Ill.). Forty μg of protein per lane were separated by 12% SDS-PAGE and electroblotted onto nitrocellulose (Amersham, Braunschweig, Germany). Equal protein loading was controlled by Ponceau red staining of membranes. After blocking for 1 h in PBS supplemented with 2% BSA (Sigma) and 0.1% Tween 20 (Sigma), immunodetection of FLICE, CPP32, PARP, Bax, Bcl-x, Bcl-2, and p53 protein was done using mouse anti-FLICE monoclonal antibody C15 (1:5 dilution of hybridoma supernatant), mouse anti-CPP32 monoclonal antibody (1:1000, Transduction Laboratories, Lexington, KY), rabbit anti-PARP polyclonal antibody (1:10000, Enzyme Systems Products), rabbit anti-Bax polyclonal antibody (1:500, Calbiochem, Bad Soden, Germany), rabbit anti-Bcl-x polyclonal antibody (1:1000, Santa Cruz Biotechnology, Santa Cruz, Calif.), mouse anti-p53 monoclonal antibody (1:10000, Transduction Laboratories), and goat anti-mouse 1gG or goat antirabbit IgG (1:5000, Santa Cruz Biotechnology), ECL (Amersham) was used for detection.

2. Results

Betulinic Acid Induces Apoptosis in Neuroectodermal Cells

FIG. 1A shows the induction of apoptosis by betulinic acid in various tumor cell lines. Cells were treated with 10 μg/ml betulinic acid for 72 h. Apoptosis was assessed by FACS analysis of propidium iodide-stained nuclei. Percentage of specific apoptosis was calculated as follows: experimental apoptosis (%) −spontaneous apoptosis in medium (%)/[100%−spontaneous apoptosis in medium (%)]×100%.

Cell lines tested were neuroblastoma (SH-EP), medulloblastoma (Daoy). Ewing's sarcoma (A17195), melanoma (A.378). breast carcinoma (MCF-7), colon carcinoma (HT-29), small cell lung carcinoma (H-146), renal cell carcinoma (KTCTL-26), and T-cell leukemia (CEM). Each column is a mean of triplicates. Standard deviations (Sds) were less than 10%. Similar results were obtained in three separate experiments.

FIG. 1B shows dose response of betulinic acid-induced apoptosis. SH-EP (♦), LAN-5 (▲), IMR-32 (x) and Kelly (■) neuroblastoma cells were treated with betulinic acid for 72 h at the indicated concentrations. Apoptosis was assessed by FACS analysis of propidium iodide-stained nuclei. Percentage of specific apoptosis was calculated as described for FIG. 1A Each data point is a mean of triplicates. SDs were less than 10%. Similar results were obtained in three separate experiments.

FIG. 1C shows dose response of betulinic acid-induced apoptosis in neuroblastoma cells ex vivo. Single-cell suspensions were prepared from tumor samples obtained from surgical resection prior to chemotherapy and incubated with indicated concentrations of betulinic acid for 18 h. Two-color fluorescence staining using FITC-conjugated mouse anti-human GD2 antibody and biotinylated annexin V followed by streptavidin-phycoerytrin was performed on a flow cytometer. Specific apoptosis was calculated as described for FIG. 1A. Representative data from one of two patients are shown. Experiments were done in triplicate. SDs were less than 10%.

Neuroblastoma, medulloblastoma, and Ewing's sarcoma cells were found to be highly responsive to betulinic acid, in addition to melanoma cells that had previously been reported to respond to betulinic acid. In contrast, epithelial tumors, such as breast carcinoma, colon carcinoma, small cell lung carcinoma, and renal cell carcinoma, as well as T-cell leukemia cells, were almost completely refractory to treatment with betulinic acid (FIG. 1A).

Neuroblastoma cells treated with betulinic acid displayed typical morphological features of apoptotic cells, with shrinkage, membrane blebbing, and nuclear fragmentation. The dose response of bongkrekic acid-induced apoptosis was assessed by flow cytometry staining DNA with propidium iodide (FIG. 1B). DNA fragmentation of neuroblastoma cells treated with betulinic acid was also found by agarose gel electrophoresis (data not shown). In addition to DNA analysis, apoptosis was also assessed by annexin V staining, leading to similar results (data not shown). To investigate whether or not betulinic acid was active against neuroblastoma cells ex vivo, we analyzed cell preparations obtained from tumor specimens by FACS analysis using two-color fluorescence to identify apoptosis in tumor cells by anti-GD2 staining. Wu et al, 1986, *Cancer Res.* 46:440–443. Patients' derived neuroblastoma cells rapidly underwent apoptosis even at low concentrations of 0.5 μg/ml betulinic acid (FIG. 1C). These results suggest that betulinic acid could exert potent antitumor activity in vivo.

Caspases Mediate Bongkrekic Acid-Induced Apoptosis

Activation of the CD95 receptor-proximal caspase FLICE and the downstream caspase CPP32 was monitored to assess different components of the caspase cascade.

Figure 2A:
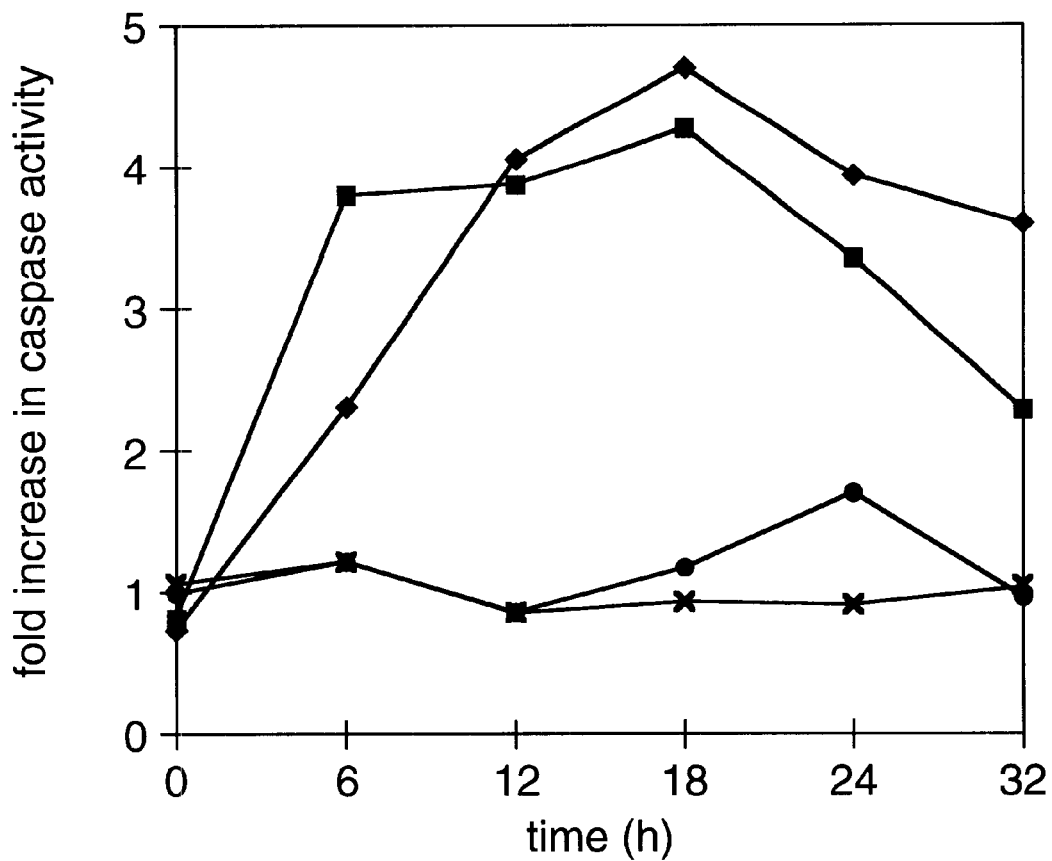

FIG. 2A shows caspase activity as affected by betulinic acid. SH-EP neuroblastoma cells were incubated with 1(x), 5 (●), 10 (♦), and 50 (■) μg/ml betulinic acid for the times indicated. Cells were permeabilized by hypotonic shock, incubated with 50 μM of the fluorogenic substrate Val-Ala-Asp-[2(4-methoxynaphthylaroide)], and analyzed with a flow cytometer. Each data point is a mean from three independent experiments in triplicate. SDs were less than 10%.

Figure 2B:
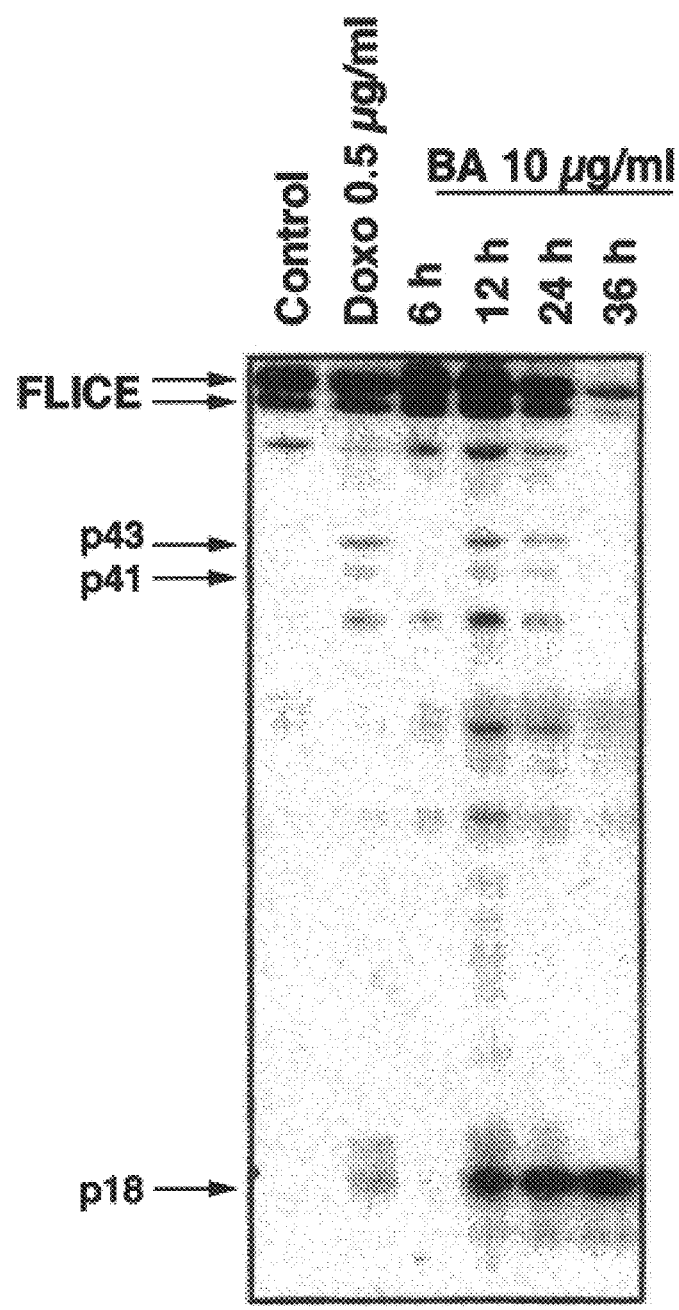
Figure 2C:
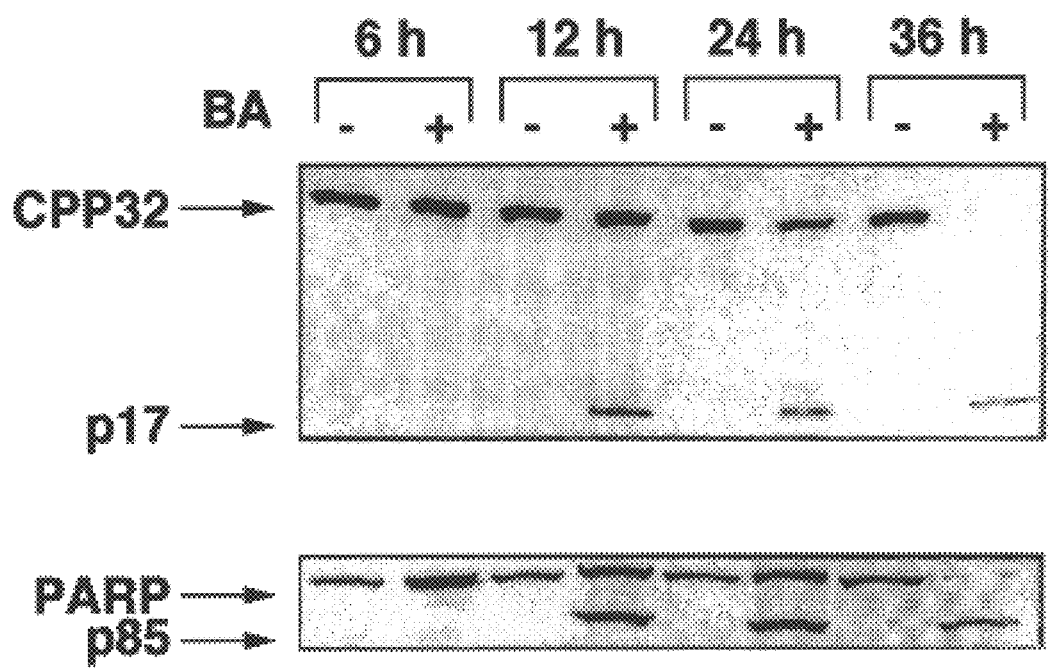

FIG. 2B and FIG. 2C show the cleavage of FLICE, CPP32 and PARP. SH-EP neuroblastoma cells were treated with 10 μg/ml betulinic acid for indicated times or with 0.5 μg/ml doxorubicin for 24 h. Forty μg of protein per lane, isolated from cell lysates, were separated by 12% SDS-PAGE, Immunodetection of FLICE (FIG. 2B). CPP32 (FIG. 2C), and PARP (C) proteins was performed by mouse anti-FLICE monoclonal antibody, mouse anti-CPP32 monoclonal antibody, or rabbit anti-PARP polyclonal antibody and ECL. Processing of FLICE, which was detected as a double band corresponding to two FLICE isoforms (caspase-8/a and 8/b) resulted in the p43 and p4 (cleavage intermediates derived from caspase-8/a and 8/b, respectively, and the p18 active subunit.

Figure 2D:
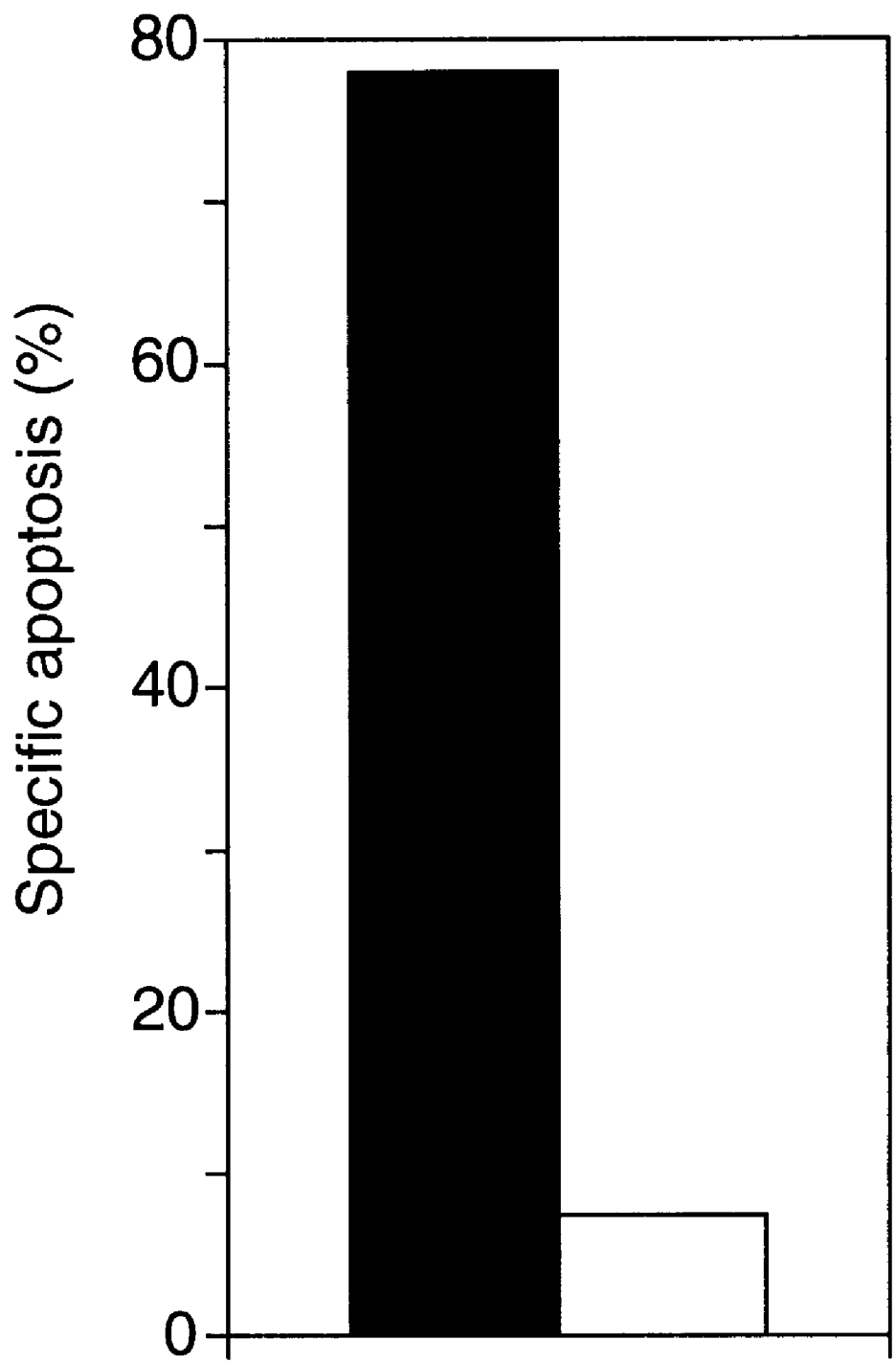

FIG. 2D shows the inhibition of betulinic acid-induced apoptosis by zVAD-fmk. SH-EP neuroblastoma cells were treated with 10 μg/ml betulinic acid for 72 h in the absence (■) or presence (□) of 60 μM zVAD-fmk. Specific apoptosis was determined and calculated as described in the legend to FIG. 1A. Each column is a mean from three independent experiments in triplicate. SDs were less than 10%.

Figure 2E:
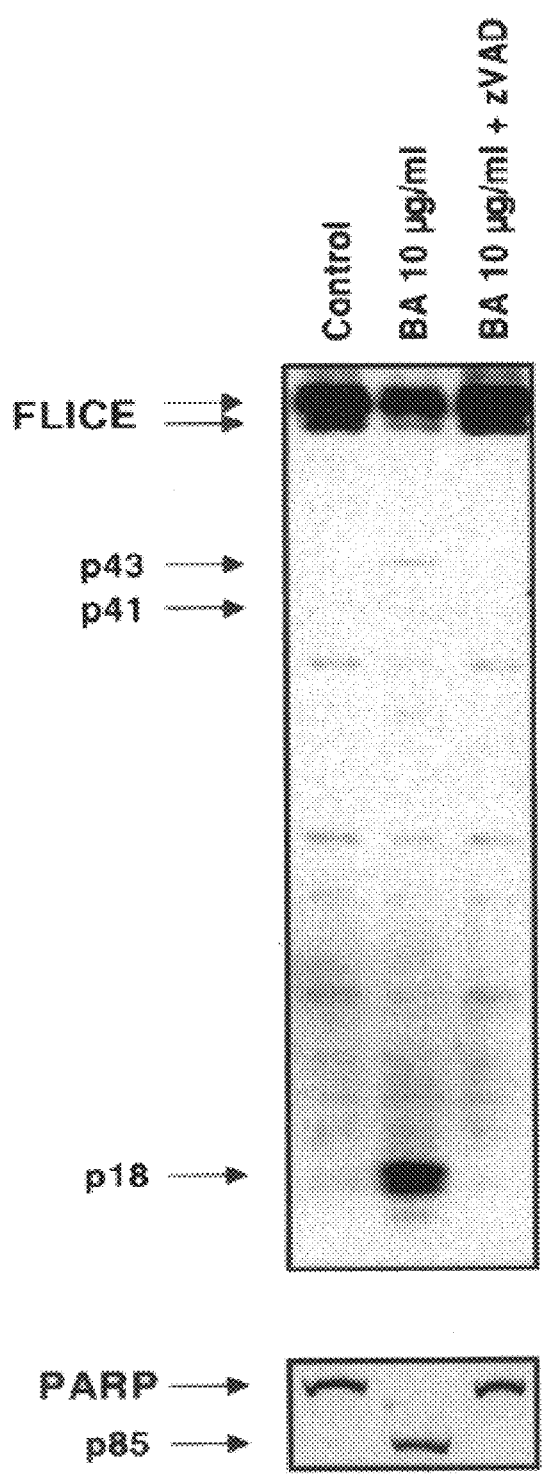

FIG. 2E shows the inhibition of betulinic acid-induced cleavage of FLICE and PARP by zVAD-fmk. SH-EP neuroblastoma cells were treated with 10 μg/ml betulinic acid for 24 h with or without 60 μM zVAD-frnk. Western blot analysis for FLICE and PARP cleavage was performed as described for FIG. 2B.

Betulinic acid caused a strong increase in caspase activity, which peaked at 18 h after addition of betulinic acid (FIG. 2A). FLICE was cleaved into p18 active subunits upon treatment with betulinic acid (FIG. 2B). In addition, CPP32 was proteolytically processed, and PARP, one of the known substrates for CPP32 was proteolytically processed, and PARP, one of the known substrates for CPP32 (35), was cleaved to its characteristic M, 85,000 fragment (FIG. 2C). Incubation with zVAD-fmk almost completely abrogated apoptosis following treatment with betulinic acid (FIG. 2D) and inhibited cleavage of FLICE and PARP (FIG. 2E), indicating that caspases were crucially involved in betulinic acid-induced apoptosis. To investigate whether or not betulinic acid could directly cleave FLICE, an in vitro cleavage assay was performed. After incubating in vitro- translated $^{35}$S-labeled FLICE with betulinic acid for 24 h at 4 or 37° C., no cleavage products were detected, demonstrating that betulinic acid did not directly cleave FLICE (data not shown), whereas the activated CD95 DISC cleaved FLICE when used in an in vitro FLICE assay. Medema et al., 1997, *EMBO J.*, 16:2794–2804.

Betulinic Acid Induces Apoptosis Independently of the CD95 System

FIG. 3A shows the analysis of CD95-L MRNA expression by RT-PCR. SH-EP neuroblastoma cells were incubated with 5 and 10 μg/ml betulinic acid for the indicated times or with 0.5 μg/ml doxorubicin for 24 h. CD95-L mRNA expression was determined by RT-PCR. Expression of μ-actin was used to control RNA integrity and equal gel loading.

FIG. 3B shows the luck of inhibition of betulinic acid-induced apoptosis by F(ab')$_2$ anti-APO-1 (anti-CD95). SH-EP neuroblastoma cells were treated with 10 μg/ml betulinic acid, 50 μg/ml VP-16, 10 μg/ml cisplatinum (DDP), or 0.5 μg/ml doxorubicin for 72 h after preincubation for 1 h with medium (■), 10 μg/ml F(ab')$_2$FII23 (IgG3 control antibody: □). or 10 μg/ml F(ab')$_2$ anti-APO-1 (anti-CD95: blocking antibody: ▯). Specific apoptosis was determined and calculated as described in the legend to FIG. 1A. Each column is a mean from three independent experiments in triplicate. SDs were less than 10%.

Betulinic acid did not induce CD95-L mRNA as assessed by RT-PCR, whereas doxorubicin strongly up-regulated CD95-L mRNA and also stimulated FLICE cleavage (FIGS. 3A and 2B). Moreover, no up-regulation of the CD95 protein could be detected following incubation with betulinic acid (data not shown), whereas up-regulation of CD95 has been reported in response to cytotoxic drugs. See., e.g., Debatin et al., 1997, *J. Natl. Cancer Inst.* 89:750–751; Micheau, 1997, *J. Natl. Cancer Inst.* 89: 783–789. Blockage of CD95 by F(ab')$_2$ anti-APO-1 antibody fragments previously shown to inhibit autocrine/paracrine death in T cells and drug-triggered apoptosis did not inhibit bongkrekic acid-induced cell death, whereas apoptosis following treatment with doxorubicin, cisplatinum, and VP-16 was markedly reduced (FIG. 3B). Taken together, these findings indicate that bongkrekic acid-mediated apoptosis was independent of CD95-L/receptor interaction.

Betulinic Acid Induces Disturbance of Mitochondrial Function

FIG. 4A shows a reduction of mitochondrial membrane potential and hyperproduction of ROS. SH-EP neuroblastoma cells were treated with 10 μg/ml betulinic acid for the indicated times. Cells were stained with the fluorochrome DiOC$_6$(3) to determine $\Delta\Psi_m$ and with HE to determine ROS generation and analyzed by flow cytometry. Fold increase in cells with low $\Delta\Psi_m$ [DiOC$_6$(3)$^{low}$] or with enhanced ROS production (HE+) is shown.

FIG. 4B shows lipid peroxidation. SH-EP neuroblastoma cells treated with 10 μg/ml bongkrekic acid for 24 h (heavy line) or control cells (thin line) were strained with NAO to assess oxidized cardiolipin and analyzed by flow cytometry.

Treatment of SH-EP cells with betulinic acid caused a disruption of the $\Delta\Psi_m$ followed by hyperproduction of ROS (FIG. 4A). The early loss of mitochondrial potential may reflect a direct effect of betulinic acid on mitochondrial function. $\Delta\Psi_m$ collapse and generation of ROS preceded cleavage of caspases, suggesting that mitochondrial events might be involved in activation of caspases. To determine whether ROS generated in mitochondria had a direct local effect on mitocyhondrial membranes, the amount of intact cardiolipin, a molecule restricted to the inner mitochondrial membrane, was assessed by means of the fluorochrome NAO. As shown in FIG. 4B, mitochondrial ROS generation was accompanied by reduced staining with NAO, suggesting that production of ROS caused an immediate damage of the inner mitochondrial membrane. Thus, bongkrekic acid-induced apoptosis seemed to be associated with mitochondrial dysfunction.

Figures 1, 5A:
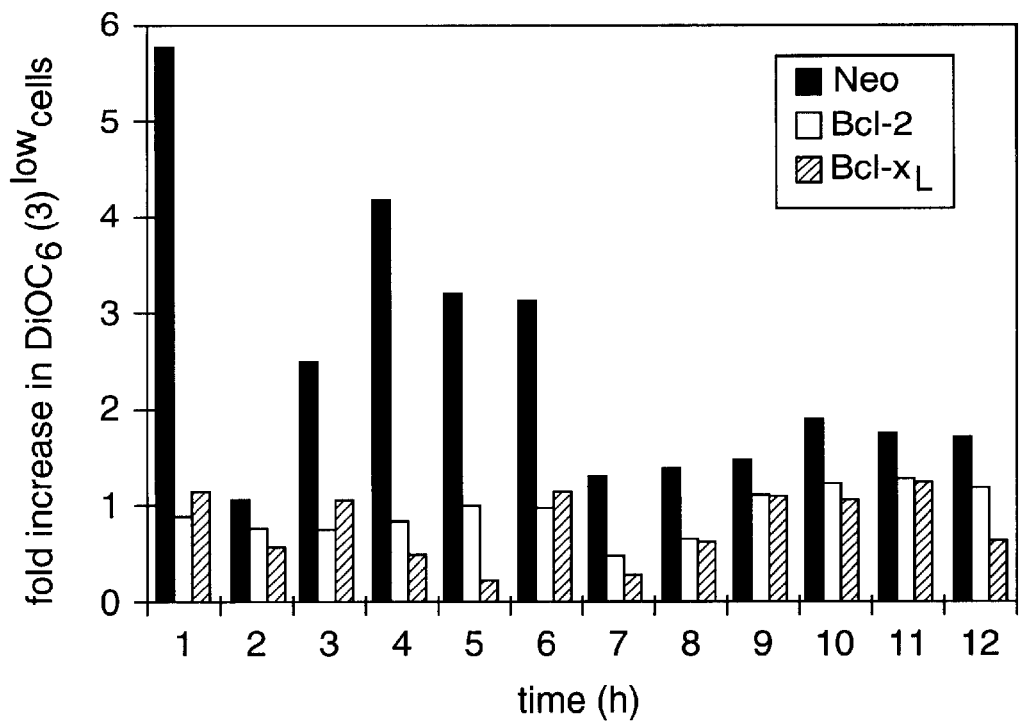
Figures 2, 5A:
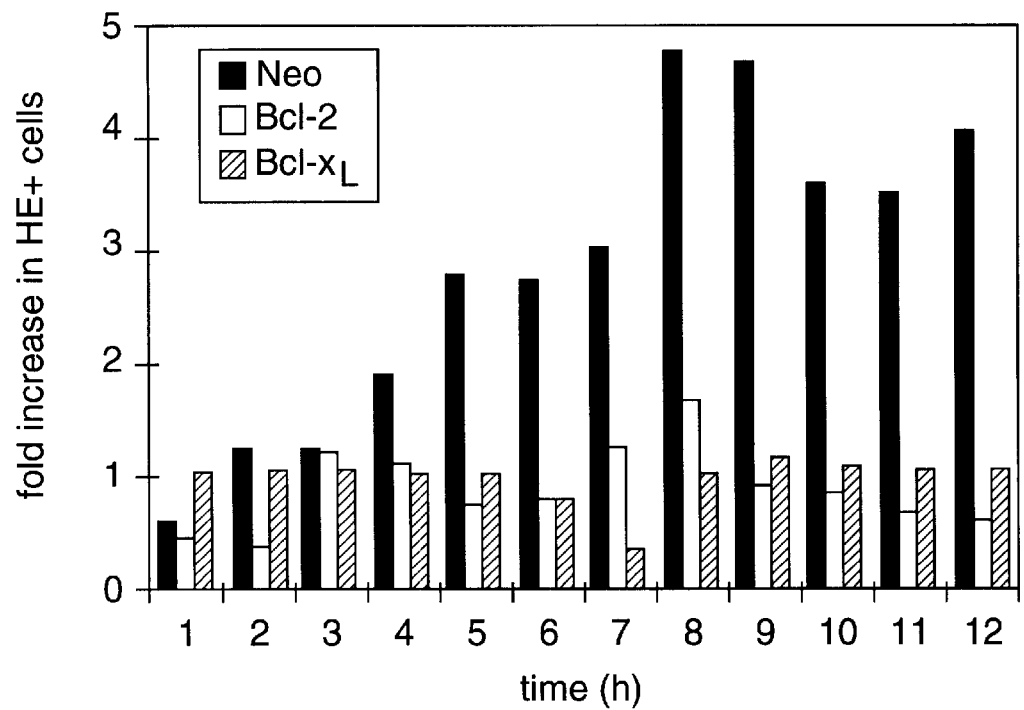

Involvement of Bcl-2 Family Proteins and p53 in Bongkrekic Acid-Induced Apoptosis FIGS. 5A-1 and 5A-2 show the inhibition of betulinic acid-induced disturbance of mitochondrial function by overexpression of Bcl-2 and Bcl-X$_L$. SH-EP neuroblastoma cells transfected with a neomycin resistance vector only, bcl-2, or bcl-X$_L$. were treated with 10 μg/ml betulinic acid for the indicated times. Cells were stained with the fluorochrome DiOC$_6$(3) to determine $\Delta\Psi_m$ and with HE to determine ROS generation and analyzed by flow cytometry. Fold increase in cells with low $\Delta\Psi_m$ (DiOC$_6$(3)$^{low}$ cells. FIG. 5A-1) or with enhanced ROS production (HE+cells, FIG. 5A-2) is shown.

Figure 5B:
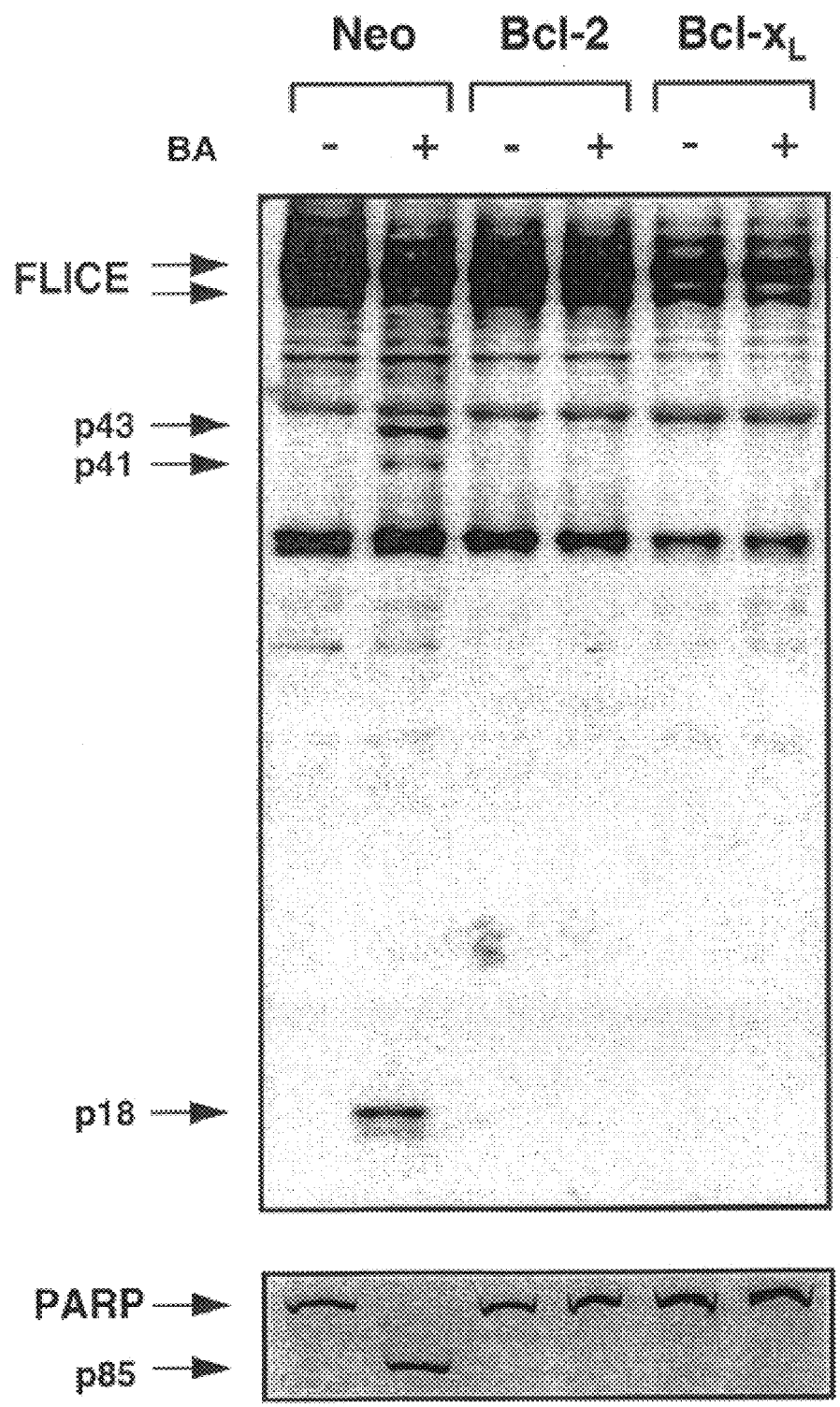

FIG. 5B shows the inhibition of betulinic acid-induced FLICE and PARP cleavage by overexpression of Bcl-2 and Bcl-X$_L$. neuroblastoma cells transfected with a neomycin resistance vector only (Neo), bcl-2, or bcl-X$_L$, were left untreated (−) or were treated with 10 μg/ml bongkrekic acid for 24 h (+). Western blot analysis for FLICE and PARP cleavage was performed as described in FIG. 2B.

Figure 5C:
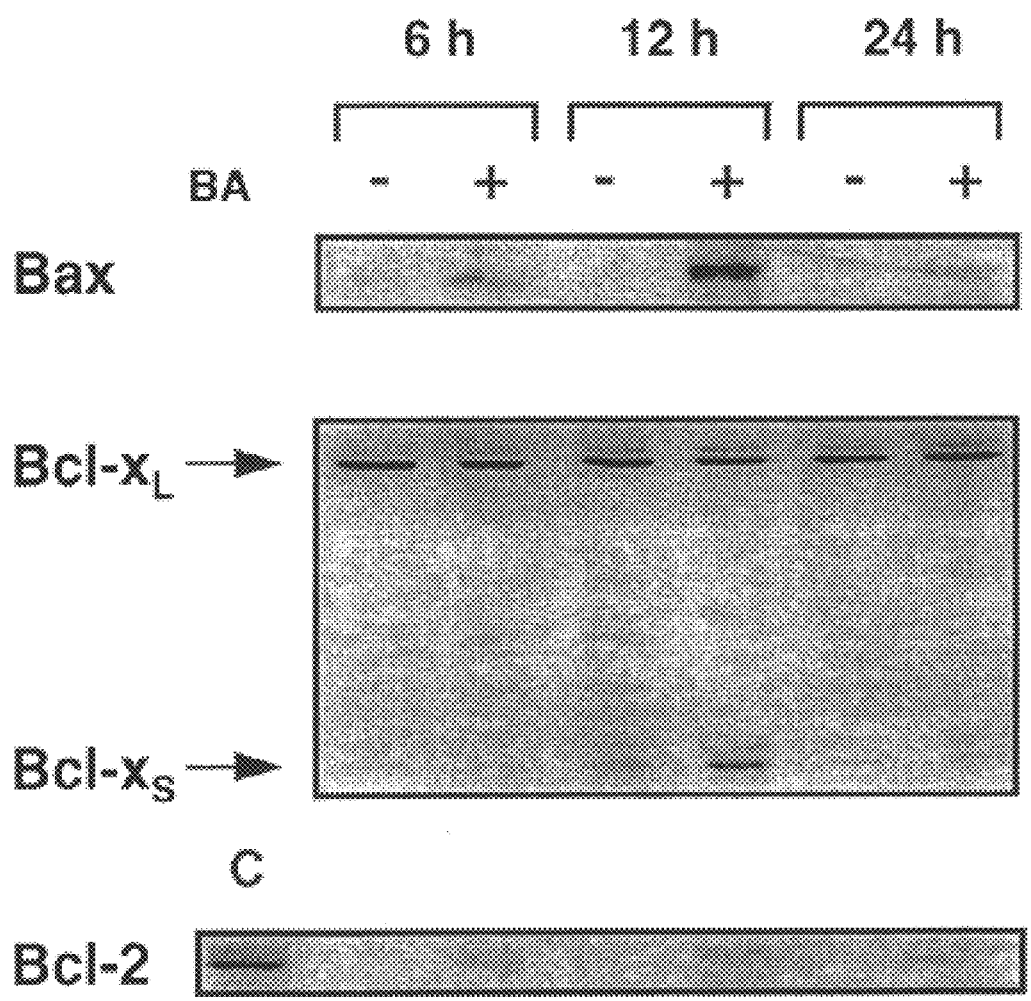

FIG. 5C. shows the induction of Bax and Bcl-X$_s$. SH-EP neuroblastoma cells were treated with 10 μg/ml betulinic acid for the indicated times. Forty μg of protein per lane, isolated from cell lysates, were separated by 12% SDS-PAGE. Immunodetection of Bax, Bcl-x, and Bcl-2 was performed by rabbit anti-Bax polyclonal antibody, rabbit anti-Bcl-x polyclonal antibody, and mouse anti-Bcl-2 monoclonal antibody using ECL. Untreated KM3 cells were used as positive control fro Bcl-2 expression.

Figure 5D:
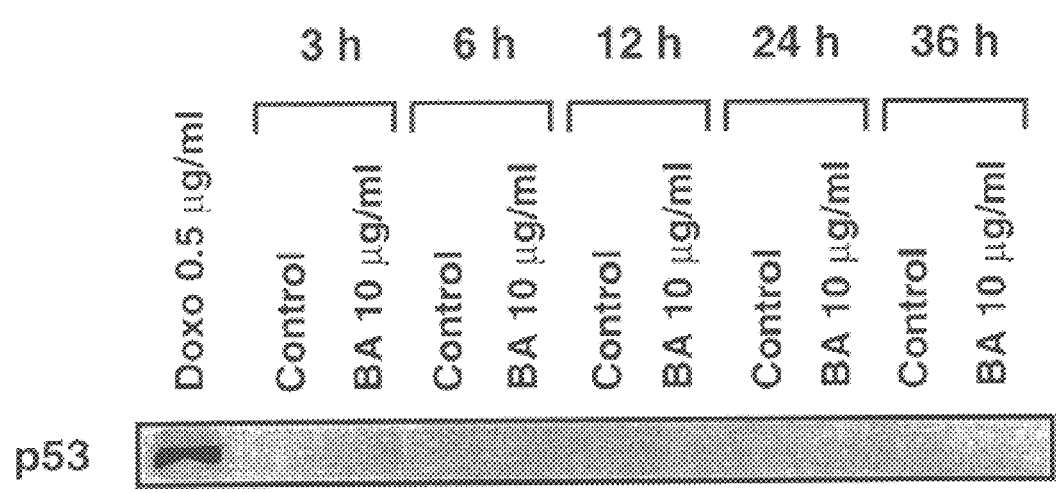

FIG. 5D. shows the lack of p53 accumulation during betulinic acid-induced apoptosis. SH-EP neuroblastoma cells were treated with 10 μg/ml betulinic acid for indicated times or 0.5 μg/ml doxorubicin for 12 h. Forty μg of protein per lane, isolated from cell lysates, were separated by 12% SDS-PAGE. Immunodetection of p53 was performed by mouse anti-p53 monoclonal antibody using ECL.

Bcl-2 and BCl-X$_L$ have recently been involved to maintain cell viability by preventing loss of mitochondrial membrane potential. Kroemer et al, 1997, *Immunol. Today.* 18:44–51. Overexpression of Bcl-2 and BCl-2x$_L$ strongly inhibited disruption of $\Delta\Psi_m$ and hyperproduction of ROS (FIGS. 5A-1 and 5A-2) and blocked cleavage of FLICE and PARP (FIG. 5B), further supporting the hypothesis that mitochondrial alterations might be involved in activation of caspases. Furthermore, pro-apoptotic Bcl-2-related proteins, such as Bax and Bcl-X$_s$, were up-regulated after incubation with betulinic acid, whereas expression levels of Bcl-2 and Bcl-x$_L$ were unaffected by treatment with betulinic acid (FIG. 5C), p53 was previously shown to be involved in the process of drug-induced apoptosis following DNA damage and may act as a direct transcriptional activator of the bax gene. Lowe et al, 1994, Science (Washington D.C.), 266:807–810; Miyashita et al., 1995, Cell 80: 293–299.

However, no accumulation of wild-type p53 protein strongly increased after treatment of SH-EP cells with doxorubicin (FIG. 5D). These findings indicate that betulinic acid-mediated apoptosis and up-regulation of Bax occurred independently of p53 protein in neuroblastoma cells.

Betulinic Acid Bypasses Resistance of CD95 and Doxorubicin-Mediated Apoptosis

FIG. 6A shows the induction of apoptosis by bongkrekic acid in CD95- and doxorubicin-resistant neuroblastoma cells. SH-EP neuroblastoma cells (■). CD95-resistant SH-EP$^{CD95R}$ cells (□) were treated with 10 μg/ml bongkrekic acid or 0.5 μg/ml doxorubicin for 72 h. Specific apoptosis was determined and calculated as described in the legend to FIG. 1A. Each column is a mean from three independent experiments in triplicate, SDs were less than 10%.

FIG. 6B shows the cleavage of FLICE and PARP in bongkrekic acid-sensitive cells. Cells (CD95-resistant neuroblastoma, SH-EP$^{CD95R}$), doxorubicin-resistant neuroblastoma (SH-EP$^{DoxoR}$), medulloblastoma (Daoy), Ewing's sarcoma (A17195), breast carcinoma (MCF-7), colon carcinoma (HT-29), small cell lung carcinoma (H-146), and renal cell carcinoma cells (KTCTL-26)] were left untreated (−) or were treated with 10 μg/ml bongkrekic acid for 24 h (+). Forty μg of protein per lane, isolated from cell lysates, were separated by 12% SDS-PAGE. Western blot analysis for FLICE and PARP cleavage was performed as described in the legend to FIG. 2B.

Because the molecular mechanism of bongkrekic acid-induced death appeared to be different from activation of CD95-L/receptor interactivation induced by other conventional cytotoxic agents, we asked whether or not betulinic acid could overcome drug resistance of tumor cells. Parental SH-EP cells and variant cell lines resistant to anti-CD95 or doxorubicin were responsive toward betulinic acid, whereas anti-CD95- and doxorubicin-resistant cells were partially resistant to doxorubicin (FIG. 6A). Moreover, incubation with betulinic acid led to cleavage of FLICE and PARP in partially resistant neuroblastoma cells (FIG. 6B). These findings show that betulinic acid mediated apoptosis in CD95- and doxorubicin-resistant SH-EP cells independently of the CD95 system and via activation of caspases. In addition, FLICE and PARP were also processed in other tumor cell lines responsive to betulinic acid, such as medulloblastoma (Daoy) and Ewing's sarcoma (A17/95), but not in tumor cells resistant to betulinic acid (MCF-7, HT-29, H-146, and KTTL-26; FIG. 6B).

C. Example 3

Betulinic Acid Induces Activation of Mitochondria and AIF-Mediated Caspase-8

This example shows that betulinic acid is a cytotoxic agent that triggers apoptosis by a direct effect on mitochondria. In isolated Mitochondria, betulinic acid directly induces loss of transmembrane potential independent of a zVAD-fmk-inhabitable caspase. This is inhibited by bongkrekic acid, an agent which stabilizes the permeability transition pore complex. Mitochondria undergoing betulinic acid induced permeability transition mediate cleavage of caspase-8 (FLICE/MACH/Mch5) and caspase-3 (CPP32/YAMA) in a cell-free system. Soluble factors such as cytochrome c or apoptosis-inducing factor (AIF) released from betulinic acid-treated mitochondria are sufficient for cleavage of caspases and nuclear fragmentation. Addition of cyrocbrome c to cyrosolic extracts results in cleavage of caspase-3, but not of caspase-8. However, supernarants of mitochondria, which have undergone permeability transition, and partially purified AIF activate both caspase-8 and -3 in cytosolic extracts and suffice to activate recombinant caspase-8. These findings show that induction of mitochondrial permeability transition alone is sufficient to trigger the full apoptosis program and that some cytotoxic drugs such as betulinic acid may induce apoptosis via a direct effect on mitochondria.

1. Materials and Methods

Drugs

Betulinic acid (Sigma, Deisenhofen, Germany) was provided as pure substance and dissolved in dimethysulfoxide.

Cell Culture

The human neuroblastoma cell line SHEP was kindly provided by M. Schwab (German Cancer Research Center, Heidelberg, Germany) and maintained in monolayer culture in 75 cm$^2$ tissue culture flasks (Falcon, Heidelberg, Germany) in RPMI 1640 medium (Life Technologies, Inc., Eggenstein, Germany) supplemented with 10% heat inactivated FCS (Conco, Wiesbaden, Germany), 10 mM HEPES, pH 7.4 (Biochrom. Berlin, Germany), 100 U/ml penicillin (Life Technologies, Inc.), 100 µg/ml streptomycin (Life Technologies, Inc.) and 2 mM L-glutamine (Biochrom) and incubated at 37° C. in 95% air/5% $CO_2$. SHEP neuroblastoma cells stably transfected with bcl-2, bcl-$X_L$ or vector control were cultured in Dulbecco's minimal Eagle's medium (Life Technologies, Inc.) containing 500 µg/ml G418 (Geneticin, Life Technologies, Inc.). See, Dole et al., 1994, *Cancer Res.* 54:3253–3259; Dole et al., 1995, *Cancer Res.* 55:2576–2582.

Determination of Apoptosis

Cells were incubated for indicated times with betulinic acid and harvested by trypsinization using 0.05% trypsin and 0.02% EDTA without $Ca^{2+}$ and $Mg^+$ (Life Technologies, Inc.). Quantification of DNA fragmentation was performed by FACS analysis of propidium iodide stained nuclei as previously described in Nicoletti et al., 1991, *J. Immunol. Methods* 139, 271–279, using CELLQuest software (Becton Dickinson, Heidelberg, Germany).

Inhibition of Drug-Induced Apoptosis By Benzyloxycarbonyl-Va-Ala-Asp-fluoromethyl Ketone (ZVAD-fmk) or Bongkrekic Acid The broad spectrum tripeptide inhibitor of caspases zVAD-fmk (Enzyme Systems Products, Dublin, USA) was used at a concentration of 60 µM and the mitochondrion-specific inhibitor bongkrekic acid at a concentration of 50 µM (kindly provided by Dr. Duine, University of Delft, Delft, The Netherlands).

Western Blot Analysis

Cells were lysed for 30 min at 4° C. in PBS with 0.5% Triton X (Serva, Heidelberg, Germany) and 1 mM PMSF (Sigma, Deisenhofen, Germany) followed by high-speed centrifugation. Membrane proteins were eluted in buffer containing 0.1 M glycine, pH 3.0 and 1.5 M Tris, pH 8.8. Protein concentration was assayed using bicinchoninic acid (Pierce, Rockford, Ill.). 40 µg protein per lane was separated by 12% or 15% SDS-PAGE and electro blotted onto nitrocellulose (Amersharn, Braunschweig, Germany). Equal protein loading was controlled by Ponceau red staining of membranes. After blocking for 1 h in PBS supplemented with 2% BSA (Sigma) and 0.1% Tween 20 (Sigma), immunodetection of caspases-3 and -8, PARP, and cytochrome c protein was done using mouse anti-caspase-8 mAb C15 (Scaffidi et al., 1997, *J. Biol. Chem.* 272, 26953–26958, 1:5 dilution of hybridoma supernatant), mouse anti-caspase-3-specific mAb (1:1000, Transduction Laboratories, Lexington, Ky.), rabbit anti-PARP polyclonal antibody (1:10000, Enzyme Systems Products) or mouse anti-cytochrome c mAb (1:5000, PharMingen, San Diego, Calif.). Goat anti-mouse IgG or goat anti-rabbit IgG (1:5000, Santa Cruz Biotechnology) followed by ECL (Amersham) was used for detection.

Preparation of Mitochondria, Cytosolic Extracts, Nuclei and Mitochondrial Supernatant For isolation of mitochondria, cells ($3 \times 10^5$ per sample) were washed twice with ice-cold PBS and resuspended with five volumes of buffer A (50 mM Tris, 1 mM EGTA, 5 mM 2-mercaproethanol, 0.2% BSA, 10 mM $KH_2PO_4$, pH 7.6, 0.4 M sucrose) and allowed to swell on ice for 20 min. Cells were homogenized with 30 strokes of a Teflon homogenizer and centrifuged at 10000 g for 10 min at 4° C. The resulting pellets were resuspended in buffer B (10 mM $KH_2PO_4$, pH 7.2, 0.3 mM mannitol, 0.1% BSA). Mitochondria were separated by sucrose gradient (lower layer: 1.6 M sucrose, 10 mM $KH_2PO_4$, pH 7.5, 0.1% BSA; upper layer: 1.2 M sucrose, 10 mM $KH_2PO_4$, pH 7.5, 0.1% BSA). Interphases containing mitochondria were washed with buffer B at 18000 g for 10 min at 4° C. and the resulting mitochondrial pellets were resuspended in buffer B. For preparation of cytosolic extracts, cells ($1 \times 10^8$ per sample) were washed twice with ice-cold PBS, resuspended with one volume of buffer A and allowed to swell on ice for 20 min. Cells were homogenized with 30 strokes of a Dounce homogenizer and centrifuged at 15000×g for 15 min ax 4° C. The protein concentration of mitochondria or cytosolic extracts was determined by Bradford method (Bio-Rad). For isolation of nuclei, cells were washed twice in ice-cold PBS, resuspended in 10 volumes of buffer C (10 mM PIPES, pH 7.4, 10 mM KCl, 2 mM $MgCl_2$, 1 mM DDT, 1 mM PMSF, 10 µM cytochalasin B), allowed to swell on ice for 20 min and homogenized using a Teflon homogenizer. Homogenates were layered over 30% sucrose in buffer C and centrifuged at 800 g for 10 min. The resulting nuclear pellets were resuspended in buffer C and washed three times. Nuclei were scored at −80° C. in aliquots of $10^8$ nuclei/ml until required. AIF-containing mitochondrial supernatant was prepared as described in Susin et aL, 1997, *J. Exp. Med.* 186, 5–37 and Susin et al., 1996, *J. Exp. Med.* 184, 1331–41.

Cell-Free System of Apoptosis

For determination of nuclear fragmentation, nuclei ($10^3$/µl) were incubated with mitochondria (1 µg/µl) in buffer D (10 mM HEPES, pH 7.4, 50 mM NaCl, 2 mM $MgCl_2$, 5 mM EGTA, 1 mM DDT, 2 mM ATP, 10 mM phosphocreatine, 50 µg/ml creatine kinase, 10 µM cytochalasin B) for 2 h at 37° C. Nuclei were stained with propidium iodide (10 µg/µl) and analyzed by flow cytometry. For determination of caspase activation, cytosolic extracts (2 µg/µl) were incubated with mitochondria (1 µg/µl), cytochrome c (0.1–100 µM) or AIF-containing mitochondrial supernatant (0.5 µg/µl) in buffer D for 2 h at 37° C. Partially purified AIF (cytochrome c-free) was prepared as previously described (0.5 mg/ml, Susin et al., 1997, *J. Exp. Med.* 186, 5–37; Susin et al., 1996, *J. Exp. Med.* 184, 1331–41). Proteins were separated by 15% SDS-PAGE and Western blot analysis was performed as described above. To confirm equal loading of mitochondrial protein, all Western blots were also developed with an antibody directed against a 60 kDa mitochondrial antigen (data not shown).

Determination of Mitochondrial Membrane Potential

Mitochondria ($5 \times 10^5$/ml) were treated with 10 µg/ml betulinic acid for 30 min, incubated with 3,3'-dihexyloxacarbocyanine iodide ($DiOC_6(3)$, 40 nM, Molecular Probes, Inc., Eugene, Oreg.) for 15 min at 37° C. and analyzed on a flow cytometer (FACS Vantage, Becton Dickinson). As a control, cells were treated with the uncoupling agent carbonyl cyanide m-chlorophenylhydrazone (mClCCP, 200 µM, Sigma).

In Vitro Translation and In Vitro Cleavage Assay

In vitro translation and in vitro cleavage assay of caspase-8 was performed as previously described in Medema et al., 1997, *EMBO J.* 16, 2794–2804.

2. Results

Betulinic Acid Triggers Mitochondrial PT in Isolated Mitochondria

Isolated mitochondria were incubated with betulinic acid and stained with the dye $DiOC_6(3)$ to assess the mitochondrial membrane potential (FIG. 7). Mitochondria isolated from SHEP cells transfected with bcl-2 or Bcl-$X_L$ or a neomycin resistance vector only were left untreated (control) or were treated with 10 µg/ml betulinic acid for 30 min in the presence or absence of 50 µM bongkrekic acid or 60 pM zVAD-fmk,. 5 mM atracryloside, a direct mitochondrial activator, was used as a positive control. $\Delta\psi_m$ was determined by staining mitochondria with the fluorochrome $DiOC_6(3)$. The dotted line in histogram 1 indicates the staining profile obtained in the presence of the $\Delta\psi_m$-dissipating agent mClCCP.

As FIG. 7 shows, Mitochondria isolated from wild type SHEP cells or from vector-only transfected cells underwent a loss of the $\Delta\psi_m$ within 30 mm of treatment with betulinic acid. betulinic acid-induced $\Delta\psi_m$ dissipation was inhibited by bongkrekic acid, a ligand of the adenine nucleotide translocator (ANT), which inhibits permeability transition (PT), and betulinic acid had no effect on mitochondria isolated from cells which bad been transfected with Bcl-2 or Bcl-$X_L$ (FIG. 7), two endogenous inhibitors of PT. However, the caspase inhibitor zVAD-fmk did not interfere with the betulinic acid-induced $\Delta\psi_m$ loss (FIG. 7). Thus, betulinic acid can directly trigger mitochondrial permeability transition without involvement of a Z-VAD-frnk-inhabitable caspase.

Betulinic Acid-Induced Mitochondrial PT-Induced Apoptosis

FIG. 8 shows nuclear fragmentation following coincubation of isolated nuclei with isolated mitochondria in the presence of betulinic acid. Mitochondria isolated from SHEP cells, transfected with bcl-2 or bcl-$X_L$ or a neomycin resistance vector only, were incubated for 6 h with nuclei and 0.1–10 µg/ml betulinic acid (FIG. 8A) or 5 mM atractyloside (FIG. 8B) in the presence or absence of 50 µM bongkrekic acid or 60 µMZ-VAD-fnk. Nuclei incubated with either mitochondria from vector only cells or with betulinic acid were used as control. Nuclear apoptosis was determined by FACS analysis of propidium iodide stained DNA content.

SHEP cells transfected with bcl-2 or bcl-$X_L$ or a neomycin resistance vector only were treated with 10 µg/ml betulinic acid or 5 mM atractyloside for 6–24 h (FIG. 8C). Mitochondria were isolated and incubated with nuclei in the presence or absence of 50 µM bongkrekic acid or 60 µMZ-VAD-fmk. Nuclei incubated with either mitochondria front vector only cells or with betulinic acid were used as control. Nuclear apoptosis was determined by FACS analysis of propidium iodide stained DNA content.

In this experimental set-up, the combination of mitochondria from Neo control cells plus nuclei and betulinic acid resulted in nuclear DNA fragmentation (FIG. 8A). Removal of mitochondria from this mixture abolished the effect of betulinic acid, indicating that mitochondria were required for betulinic acid-induced nuclear apoptosis in this cell-free system. Mitochondria without addition of betulinic acid bad no effect on nuclei. No DNA fragmentation was observed using a combination of mitochondria plus nuclei to which apoptogenic doses of standard cytotoxic drugs such as doxorubicin, cisplatinum or etoposide were added (data not shown). In contrast, atractyloside (Atra), which specifically triggers mitochondrial PT by binding to the adenine nucleotide translocator at the inner mitochondrial membrane, Kroemer et al., 1997, *Immunol. Today,* 18:44–51, had the same effect as betulinic acid (FIG. 8B). Fragmentation of nuclei induced by betulinic acid was inhibited by zVAD-fmk, by bongkrekic acid or when mitochondria were obtained from cells overexpression Bcl-2 or Bcl-$X_L$ (FIG. 8A). Nuclear fragmentation could also be induced by mitochondria isolated from cells pretreated with betulinic acid (FIG. 8C). This effect was again blocked by zVAD-fmk, by bongkrekic acid or by overexpression of Bcl-2 or Bcl-$X_L$ (FIG. 8C). These findings indicate that betulinic acid has a direct and specific effect on mitochondria leading to fragmentation of nuclei and apoptotic DNA degradation.

Betulinic Acid-Induced Cleavage of Caspases Depends on Mitochondrial PT

FIG. 9A shows that Caspases are cleaved by mitochondria undergoing PT. SHEP cells transfected with bcl-2 or Bcl-$X_L$ or a neomycin resistance vector only were treated with 10 µg/ml betulinic acid for 16 h. Mitochondria were isolated and incubated with cytosolic extracts for 6 h in the presence or absence of 60 µM zVAD-fmk (left panel, cells). Alternatively, mitochondria isolated from untreated cells were incubated with 10 µg/ml betulinic acid or 5 mM atractyloside together with cytosolic extracts for 6 h in the presence or absence of 60 µMZ-VAD-fmk (right panel, mitos, Atra). Cytosolic extracts incubated with mitochondria isolated from untreated cells or with untreated mitochondria were used as control. 40 µg protein per lane isolated front cell lysates were separated by 15% SDS-PAGE. Immunodetection of caspases-3, -8 and PARP protein was performed by mouse anti-caspase-3 mAb, mouse anti-caspase-8 mAb, rabbit anti-PARP polyclonal antibody and ECL.

Figure 9B:
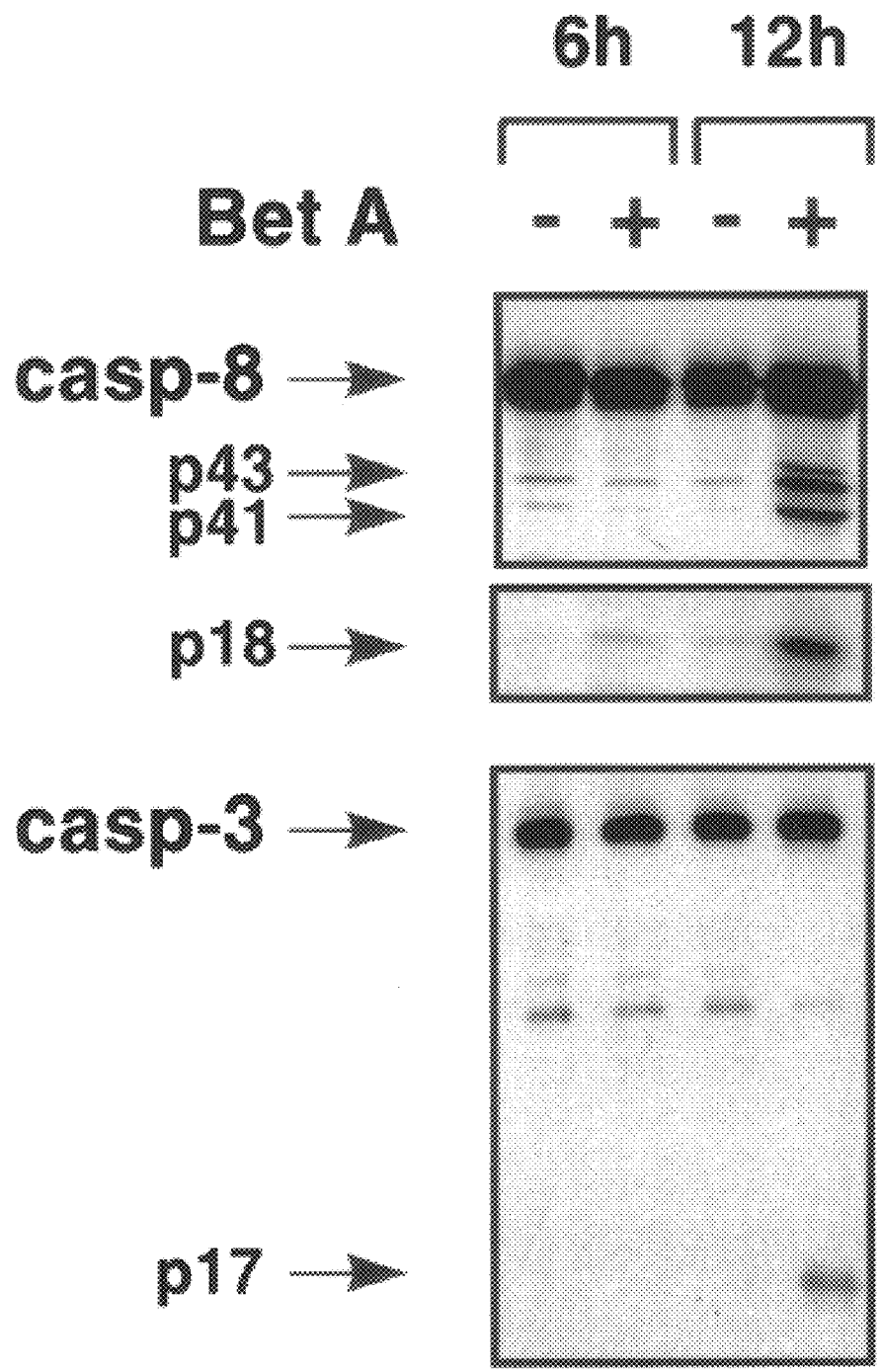

FIG. 9B shows the kinetic of betulinic acid-induced cleavage of caspases in a cell-free system. SHEP cells treated with 10 µg/ml betulinic acid for indicated times. Mitochondria were isolated and incubated with cytosolic extracts for 6 h. Western blot analysis was performed as described above.

Incubation of cyroplasmic extracts with mitochondria isolated from betulinic acid-treated cells resulted in processing of caspase-6, caspase-3 and the prototype substrate PARP (FIG. 9A, mitochondria). Cleavage of caspases was blocked in the presence of zVAD-fmk or when mitochondria from Bcl-2 or Bcl-x1 overexpression cells were used (FIG. 9A). Similarly, cleavage of caspases was observed when betulinic acid-treated mitochondria were used (FIG. 9A, mitos). Treatment of isolated mitochondria with Atra also led to activation of caspases (FIG. 9A). Moreover, mitochondria isolated from betulinic acid-treated cells induced cleavage of caspase-8, caspase-3 and PARP in a time dependent manner which was first detectable after treatment with betulinic acid for 12 h (FIG. 9B). To see whether betulinic acid could directly induce cleavage of caspases, an in vitro cleavage assay was performed. Following incubation of in vitro translated, radiolabeled caspase-8 or caspase-3 with betulinic acid no cleavage products were detected (data not shown) indicating that betulinic acid does not directly cleave caspase-8 or caspase-3. These findings suggest that betulinic acid-induced caspase activation is mediated by mitochondrial PT.

Betulinic Acid Causes the Release of Apoptogenic Factors From Isolated Mitochondria FIG. 10A shows that soluble factor(s) released from mitochondria undergoing PT induce cleavage of caspases. Mitochondria isolated from SHEP cells transfected with bcl-2 or Bcl-$X_L$ or a neomycrn resistance vector only were treated with 10 µg/ml betulinic acid or 5 mM atractyloside for 0.5 h in the presence or absence of 50 µM bongkrekic acid or 60 µM zVAD-fmk. Mitochondrial supernatants obtained by high speed centrifugation were incubated with cytosolic extracts for 6 h at 37° C. Cytosolic extracts incubated with supernatants of untreated mitochondria were used as control. Western blot analysis was performed as described for FIG. 9A.

FIG. 10B shows that soluble factor(s) released from mitochondria undergoing PT induce nuclear fragmentation. Mitochondria isolated from SHEP cells transfected with bcl-2, Bcl-$X_L$ or a neomycin resistance vector only were treated with 10 µg/ml betulinic acid or 5 mM atractyloside for 0.5 h in the presence or absence of 50 µM bongkrekic acid or 60 µM zVAD-fmk. Mitochondrial supernatants obtained by high speed centrifugation were incubated with nuclei for 2 h at 37° C. Nuclei incubated with supernatants of untreated mitochondria were used as control.. Nuclear apoptosis was determined by FACS analysis of propidium iodide stained DNA content.

FIG. 10C shows betulinic acid-induced cytochrome c release. Mitochondria isolated from SHEP cells transfected with bcl-2, Bcl-$X_L$ or a neontycin resistance vector only (Neo) were treated with 10 µg/ml betulinic acid. 5 µg protein per lane were separated by 15% SDS-PAGE. Immunodetection of cytochrome c was performed by mouse anti-cytochronte c mAb and BCL.

When supernatants from betulinic acid-treated mitochondria were added to cytosolic extracts, caspase-8, -3 and PARP were cleaved (FIG. 10A). Processing of caspases was inhibited by bongkrekic acid, zVAD-fmk or in mitochondria from Bcl-2 or Bcl-$X_L$ over-expression cells (FIG. 10A). In addition, supernatants from betulinic acid-treated mitochondria induced DNA fragmentation, and this effect was also blocked in the presence of bongkrekic acid, zVAD-fmk or by over-expression of Bcl-2 or Bcl-$X_L$ (FIG. 10B). Similarly, caspase activation and nuclear fragmentation were observed when Atra was used instead of betulinic acid (FIGS. 10A, B). This indicates that betulinic acid triggers the mitochondrial release of soluble apoptogenic factor(s). Accordingly, betulinic acid directly induced cytochrome c release in isolated mitochondria (FIG. 10C). This betulinic acid-driven release of cytochrome c was blocked by bongkrekic acid or in mitochondria from Bcl-2 or Bcl-$X_L$ over-expression cells (FIG. 10C).

Caspase-8 Cleavage is Mediated by AIF, But Not By Cytochrome c

FIG. 11A shows that cytochrome c induces cleavage of caspase-3. Cytosolic extracts from SHEP cells were incubated with 0.1–100 µM cytochrome c. Immunodetection of caspases-3, -8 and PARP was performed as described in FIG. 9A.

FIG. 11B shows that AIF induces cleavage of both caspase-8 and -3. Cytosolic extracts from SHEP cells transfected with a neomycin resistance vector only (Nec) or bcl-2 were incubated with partially purified AIF. Immunodetection of caspases-3, -8 and PARP was performed as described for FIG. 9A.

FIG. 11C shows that AIF cleaves recombinant caspase-8. In vitro translated, $^{35}$S-labeled caspase-8 was incubated with partially purified AIF for 16 h at 4° C. in the presence or absence of 60 µMZ-VAD-fmk. The reaction products were separated by 15% SDS-PAGE and visualized by autoradiography. The migration position of an N-terminal truncated caspase-8 is labeled by an open arrow.

As shown in FIG. 11A, cytochrome c triggered the proteolytic processing of caspase-3 to its active subunits and caused caspase-mediated cleavage of PARP (FIG. 11A). However, addition of cytochrome c to cytosolic extracts did not induce caspase-8 cleavage (FIG. 11A). In contrast, when mitochondrial supernatants or partially purified (cytochrome c-free) AIF were used instead of cytochrome c, both caspase-3 and -8 were cleaved in cytosolic extracts (FIG. 11B). In addition, partially purified AIF induced cleavage of in vitro translated, radiolabeled caspase-8 to the active p18 subunits (FIG. 11C). These findings demonstrate that distinct mitochondrial proteins released by betulinic acid differ in their capacity to activate different caspases. Cleavage of caspase-8 downstream of mitochondria seems to require AIF activity.

D. Example 4

Molecular Ordering of Apoptosis Induced By Anticancer Drugs

Apoptosis mediated by anticancer drugs may involve activation of death-inducing ligand/receptor systems such as CD95 (APO-1/Fas), cleavage of caspases and perturbance of mitochondrial functions. In this example, the sequence of these events was investigated in SHEP neuroblastoma cells transfected with Bcl-2 or Bcl-$X_L$ using two different drugs, namely doxorubicin (doxorubicin), which activates the CD95/CD95-L system, and betulinic acid, which does not enhance the expression of CD9S or its ligand and which, as shown here, directly targets mitochondria.

Apoptosis induced by both drugs was inhibited by Bcl-2 or Bcl-$X_L$ overexpression or by bongkrekic acid, an agent which stabilizes mitochondrial membrane barrier function, suggesting a critical role for mitochondria. After doxorubicin treatment, enhanced CD95/CD95-L expression and caspase-8 activation were not blocked by Bcl-2 or Bcl-$X_L$ and were found in cells with a still normal mitochondrial transmembrane potential ($\Delta\Psi_m^{high}$ cells). In marked contrast, after betulinic acid treatment, caspase-8 activation occurred in a Bcl-2- or Bcl-$X_L$-inhibitable fashion and was confined to cells that had lost their mitochondrial transmembrane potential ($\Delta\Psi_m^{high}$ cells). Mitochondria from cells treated with either doxorubicin or betulinic acid induced cleavage of both caspase-8 and caspase-3 in cytosolic extracts. Thus, caspase-8 activation may occur upstream or downstream of mitochondria, depending on the apoptosis-initiating stimulus. In contrast to caspase-8, cleavage of caspase-3 or PARP was always restricted to $\Delta\Psi_m^{high}$ cells, downstream of the Bcl-2- or Bcl-$X_L$-controlled checkpoint of apoptosis. Cytochrome c, released from mitochondria undergoing permeability transition, activated caspase-3 but not caspase-8 in a cell-free system. However, both caspases were activated by apoptosis-inducing factor (AIF) indicating that the mechanism of caspase-8 activation differed from that of caspase-3 activation.

1. Materials and Methods

Drugs

Doxorubicin (Farmitalia, Milano, Italy) and betulinic acid (Sigma, Deisenhofen, Germany) were provided as pure substances and dissolved in sterile water (doxorubicin) or dimethylsulfoxide (betulinic acid).

Cell Culture

The human neuroblastoma cell line SHEP was kindly provided by Professor M. Schwab (German Cancer Research Center, Heidelberg, Germany). Cells were maintained in monolayer culture in 75 cm$^2$ tissue culture flasks (Falcon, Heidelberg) Germany) in RPMI 1640 medium (Life Technologies, Inc., Eggenstein, Germany) supplemented with 10% heat inactivated FCS (Conco, Wiesbaden, Germany), 10 mM HEPES, pH 7.4 (Biochrom, Berlin, Germany), 100 U/ml penicillin (Life Technologies, Inc.). 100 µg/ml streptomycin (Life Technologies, Inc.) and 2 mM L-glutamine (Biochrom) and incubated at 37° C. in 95% air/5% CO2). SHEP neuroblastoma cells stably transfected with bcl-2, bcl-$X_L$ or vector control were cultured in Dulbecco's minimal Eagle's medium (Life Technologies, Inc.) containing 500 µg/ml G418 (Geneticin, Life Technologies, Inc.; Dole et al., 1994, *Cancer Res.* 54:3253–3259; Dole et al., 1995, Cancer Res. 55:2576–2582).

Determination of Apoptosis

Cells were incubated for indicated times with doxorubicin, betulinic acid or anti-APO-1 and harvested by trypsinization using 0.05% trypsin and 0.02% EDTA without Ca$^{2+}$ and Mg$^{2+}$(Life Technologies, Inc.). Quantification of DNA fragmentation was performed by FACS analysis of propidium iodide stained nuclei as previously described in Nicoletti et al., *J. ImmunoL Methods* 139:271–279, using CELLQuest software (Becton Dickinson, Heidelberg, Germany).

Inhibition of Drug-Induced Apoptosis by Benzyloxycarbonyl-Val-Ala-Asp-Fluoromethyl Ketone (zVAD-fmk) or Bongkrekic Acid The broad spectrum tripeptide inhibitor of caspases zVAD-fmk (Enzyme Systems Products, Dublin, USA) was used at a concentration of 60 µM and the mitochondrion-specific inhibitor bongkrekic acid at a concentration of 50 µM (kindly provided by Dr. Duine, University of Delf, Delf, The Netherlands).

Analysis of CD95 Expression

Cells were stained with anti-APO-1 (CD95) IgGl monoclonal antibody (moab) (1 µg/ml; Trauth et al., 1989, *Science* 245:301–305) for 45 minutes at 4° C. followed by goat anti-mouse IgG-FITC (Immunotech, Hamburg, Germany) for 30 minutes at 4° C. FII23 IgGl antibody was used as an isotype matched non-binding antibody to control unspecific binding.

RT-PCR For CD95 and CD95-L mRNA

Total RNA was prepared using the Qiagen total RNA kit (Qiagen, Hilden, Germany). RNA was converted to cDNA by reverse transcription and amplified for 38 cycles by PCR in a thermocycler (Stratagene, Heidelberg, Germany) using the Gene Amplification RNA-PCR kit (Perkin Elmer, Branchburg, N.J.) following the manufacturer's instructions. A 500-base pair fragment of CD95-L was amplified using primer 5'ATGTTTCAGCTCTTCCACCTACAGA3' (SEQ ID:No 1) and 5'CCAGAGAGAGCTCAGATACGTTGAC3' (SEQ ID NO:2) and a 311-base pair fragment of CD95 was amplified using primer 5'TCAAGGAATGCACACTCAC-CAGC (SEQ ID NO:3) and 5'GGCTTCATTGACACCAT-TCTTTCG3' (SEQ ID NO:4). Expression of β-actin (MWG-Biotech, Ebersberg, Germany) was used as a standard for RNA integrity and equal gel loading. PCR-reaction products were run at 60 V for 2 h on a 1.5% agarose gel stained with ethidium bromide and visualized by UV illumination.

Western Blot Analysis

Cells were lysed for 30 mm at 4° C. in PBS with 0.5% Triton X (Serva, Heidelberg, Germany) and 1 mM PMSF (Sigma, Deisenhofen, Germany) followed by high-speed centrifugation. Membrane proteins were eluted in buffer containing 0.1 M glycine, pH 3.0 and 1.5 M Tris, pH 8.8. Protein concentration was assayed using bicinchoninic acid (Pierce, Rockford, Ill.). 40 µg protein per lane was separated by 12% or 15% SDS-PAGE and electroblotted onto nitrocellulose (Amersham, Braunschweig, Germany). Equal protein loading was controlled by Ponceau red staining of membranes. After blocking for 1 h in PBS supplemented with 2% BSA (Sigma) and 0.1% Tween 20 (Sigma), immunodetection of caspases-3 and -8, PARP, CD95-L, CD95 and cytochrome c protein was done using mouse anti-caspase-8 moab C15 (Scaffidi et al., 1997, *J. Biol. Chem.* 272:26953–26958, 1:5 dilution of hybridoma supernatant), mouse anti-caspase-3-specific moab (1:1,000, Transduction Laboratories, Lexington, Ky.), rabbit anti-PARP polyclonal antibody (1:10,000, Enzyme Systems Products), mouse anti-CD95-L moab (1:5,000, Transduction Laboratories), mouse anti-CD95 moab (1:1,000, Transduction Laboratories) or mouse anti-cytochrome c moab (1:5,000, PharMingen, San Diego, Calif.). Goat anti-mouse IgG or goat anti-rabbit IgG (1:5,000, Santa Cruz Biotechnology) followed by ECL (Amersham) was used for detection.

Preparation of Mitochondria, Cytosolic Extracts and Nuclei

For isolation of mitochondria, cells (3×10$^8$ per sample) were washed twice with ice-cold PBS and resuspended with five volumes of buffer A (50 mM Tris buffer, 1 mM EGTA, 5 mM 2-mercaptoethanol, 0.2% BSA, 10 mM KH$_2$PO$_4$, pH 7.6, 0.4 M sucrose) and allowed to swell on ice for 20 min. Cells were homogenized with 30 strokes of a teflon homogenizer and centrifuged at 4000×g for 1 min. at 4° C. The supernatants were further centrifuged at 10.000×g for 10 mm at 4° C. and the resulting pellets were resuspended in buffer B (10 mM KH$_2$PO$_4$, pH 7.2, 0.3 mM mannitol, 0.1% BSA). Mitochondria were separated by sucrose gradient (lower layer: 1.6 M sucrose, 10 mM KH$_2$PO$_4$, pH 7.5, 0.1% BSA; upper layer: 1.2 M sucrose, 10 mM KH$_2$PO$_4$, pH 7.5. 0.1% BSA). Interphases containing mitochondria were washed with buffer B at 18.000×g for 10 min at 4° C. and the resulting mitochondrial pellets were resuspended in buffer B. For preparation of cytosolic extracts, cells (1×10$^8$ per sample) were washed twice with ice-cold PBS, resuspended with one volume of buffer A and allowed to swell on ice for 20 min. Cells were homogenized with 30 strokes of a Dounce homogenizer and centrifuged at 15,000×g for 15 mm at 4° C. The protein concentration of mitochondria or cytosolic extracts was determined by the Bradford method. For isolation of nuclei cells were washed twice in ice-cold PBS, resuspended in 10 volumes of buffer C (10 mM Pipes, pH 7.4, 10 mM KC1, 2 mM $MgCl_2$, 1 mM DDT, 1 mM PMSF, 10 μM cytochalasin B), allowed to swell on ice for 20 min, and homogenized using a teflon homogenizer. Homogenates were layered over 30% sucrose in buffer C and centrifuged at 800×g for 10 min. The resulting nuclear pellets were resuspended in buffer C and washed three times. Nuclei were stored at −80° C. in aliquots of $10^8$ nuclei/ml until required. AIF-containing mitochondrial supernatant was prepared as previously described in Kroemer et al., 1997, *Immunol. Today* 18:44–51.

Cell-Free System of Apoptosis

For determination of nuclear fragmentation, nuclei ($10^3$/μl) were incubated with mitochondria (1 μg/μl) in buffer D (10 mM HEPES, pH 7.4, 50 mM NaCl, 2 mM $MgCl_2$, 5 mM EGTA, 1 mM DDT, 2 mM ATP, 10 mM phosphocreatine, 50 μg/ml creatine kinase, 10 μM cytochalasin B) for 2 h at 37° C. Nuclei were stained with propidium iodide (10 μg/μl) and analyzed by flow cytometry (Susin et al., 1997 *Exp. Cell Res.* 236:397–403). For determination of caspase activation, cytosolic extracts (2 μg/μl) were incubated with mitochondria (1 μg/μl), cytochrome c (10 μM) or AIF-containing mitochondrial supernatant (0.5 μg/μl) in buffer D for 2 h at 37° C. Proteins were separated by 15% SDS-PAGE and Western blot analysis was performed as described before.

Determination of Mitochondrial Membrane Potential

For determination of mitochondrial membrane potential, cells ($5\times10^5$/ml) were incubated with 3,3'-dihexyloxacarbocyanide iodide ($DiOC_6(3)$, 40 nM, Molecular Probes, Inc., Eugene, Oreg.) for 15 min at 37° C. and analyzed on a flow cytometer (FACScan) (Zamzarni et al., 1996 *J. Exp. Med.* 183:1533–44). For cell sorting, cells were stained with $DiOC_6(3)$ and sorted into $DiOC_6(3)^{high}$ and $DiOC_6(3)^{low}$ cells on a cytofluorometer (FACS Vantage, Becton Dickinson). As a control, cells were treated with the uncoupling agent carbonyl cyanide m-chlorophenylhydrazone (mCICCP, 200 μM, Sigma).

2. Results

Doxorubicin- and Betulinic Acid-Induced Apoptosis Depends on Mitochondrial PT and Caspase Activation FIG. 12 shows drug-induced apoptosis and mitochondrial PT. FIGS. A–C show that doxorubicin- and betulinic acid-induced apoptosis depends on mitochondrial PT and activation of caspases. SHEP cells transfected with Bcl-2 or BCl-$X_L$ or a neomycin resistance vector only (Neo) were treated with 0.5 μg/ml Doxorubicin or 10 μg/ml Betulinic acid for 48 h (A) or 24 h (B and C). Cells transfected with a neomycin resistance vector only (Neo) were treated in the presence or absence of 50 μm BA or 60 μm zVAD-fmk. Nuclear apoptosis was determined by FACS analysis or propidium iodide-stained DNA content in intact cells (A) or in a CFS incubating isolated nuclei with mitochondria from cells treated with Doxo or betulinic acid (C). ΔΨm was determined by staining cells with the potential-sensitive fluorochrome $DiOC_6(3)$ (B).

FIG. 12D shows that betulinic acid directly induces mitochondrial PT. Mitochondria isolated from SHEP cells transfected with Bcl-2 or Bcl-$X_L$ or a neomycin resistance vector only (Neo) were treated with 10 μg/ml betulinic acid for 0.5 h. Cells transfected with a neomycin resistance vector only (Neo) were treated in the presence or absence or 50 μm betulinic acid or 60 μm zVAD-fmk. ΔΨm was determined by staining mitochondria with the fluorochrome $DiOC_6(3)$. The dotted line in the first histogram indicates the staining profile obtained in the presence of the ΔΨm-dissipating agent carbonyl cyanide m-chlorophenylhydrazone.

Doxorubicin- and betulinic acid-induced apoptosis was analyzed by determining nuclear fragmentation and disruption of the $\Delta\Psi_m$ doxorubicin and betulinic acid induced loss of $\Delta\Psi_m$ and nuclear fragmentation (FIG. 12A and B). Both the mitochondrial and the nuclear manifestations of apoptosis were blocked by overexpression of Bcl-2 and Bcl-$X_L$ (FIGS. 12A and B). To determine whether apoptosis involved opening of the mitochondrial PT pore, the effect of bongkrekic acid, a specific inhibitor of this pore was tested. Addition of bongkrekic acid inhibited drug-triggered nuclear fragmentation and ΔΨm loss, indicating that mitochondrial alterations involved opening of PT pores (FIGS. 12A and B). In doxorubicin-treated cells, nuclear fragmentation and loss of $\Delta\Psi_m$ were both inhibited by the broad range caspase inhibitor zVAD-fmk (FIGS. 12A and B). In contrast, zVAD-fmk only affected the betulinic acid-induced nuclear fragmentation, yet had no effect on betulinic acid-induced $\Delta\Psi_m$ dissipation (FIGS. 12A and B). To test whether drug-induced mitochondrial alterations were sufficient to cause nuclear fragmentation, mitochondria isolated from drug-treated cells were incubated with nuclei in a cell-free system, and nuclear DNA loss was measured by flow cytometry. Mitochondria from doxorubicin- or betulinic acid- treated cells induced nuclear DNA fragmentation (FIG. 12C). This effect was blocked by overexpression of Bcl-2 or Bcl-$X_L$, as well as by treatment of cells with zVAD-fmk or bongkrekic acid (FIG. 12C). Taken together, these experiments suggest that nuclear apoptosis induced by doxorubicin or betulinic acid indistinguishably depends on mitochondrial PT and caspase activation. However, the mechanism leading to the $\Delta\Psi_m$ loss depends on which anticancer agent is used. In the case of doxorubicin, it requires the activation of zVAD-fmk-inhibitable caspases. In sharp contrast, betulinic acid triggers $\Delta\Psi_m$ dissipation in a caspase-independent fashion.

Betulinic Acid Directly Triggers Mirochondrial PT

Betulinic acid caused a loss in $\Delta\Psi_m$ in isolated mitochondria (FIG. 12D). This loss of $\Delta\Psi_m$ was inhibited by Bcl-2 or Bcl-$X_L$ overexpression or by bongkrekic acid (FIG. 12D), indicating that the $\Delta\Psi_m$ loss involved PT. However, the decline in $\Delta\Psi_m$ was not blocked by zVAD-fmk (FIG. 12D) suggesting that betulinic acid can trigger PT through a direct effect on mirochondria.

Doxorubicin Induces CD95-L and CD95 Upstream of Mitochondria

FIG. 13A shows the induction of CD95-L. SHEP cells transfected with Bcl-2 or Bcl-$X_L$ or a neomycin resistance vector only (Neo) were treated (Lanes+) with 0.5 μg/ml Doxo or 10 μg/ml betulinic acid for 24 h. CD95-L mRNA expression was determined by RT-PCR. Expression of β-actin was used to control RNA integrity and equal gel loading. For Western blot. 40 μg protein of cell lysates per lane were separated by 12% SDS-PAGE. CD95-L protein was detected as a $M_r$ 37,000 band by mouse anti-CD9S-L moab and enhanced chemiluminescence.

Figure 14A:
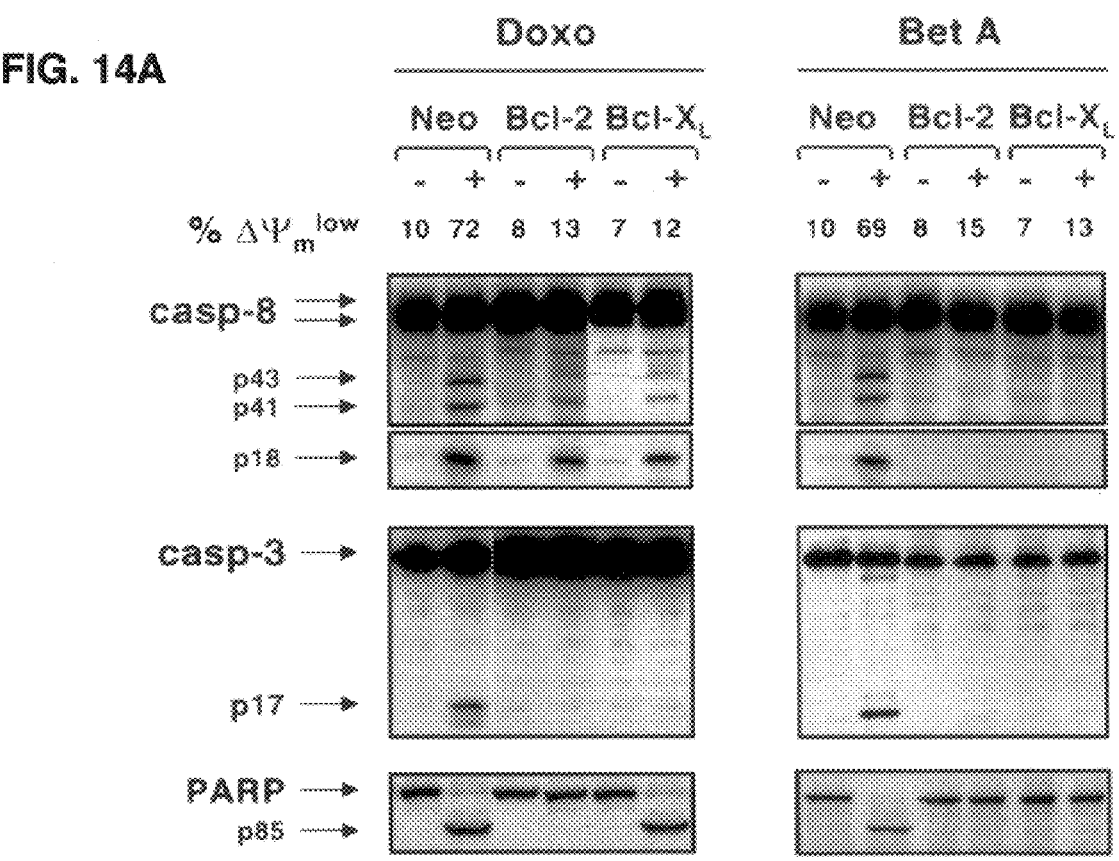
Figures 1, 14B:
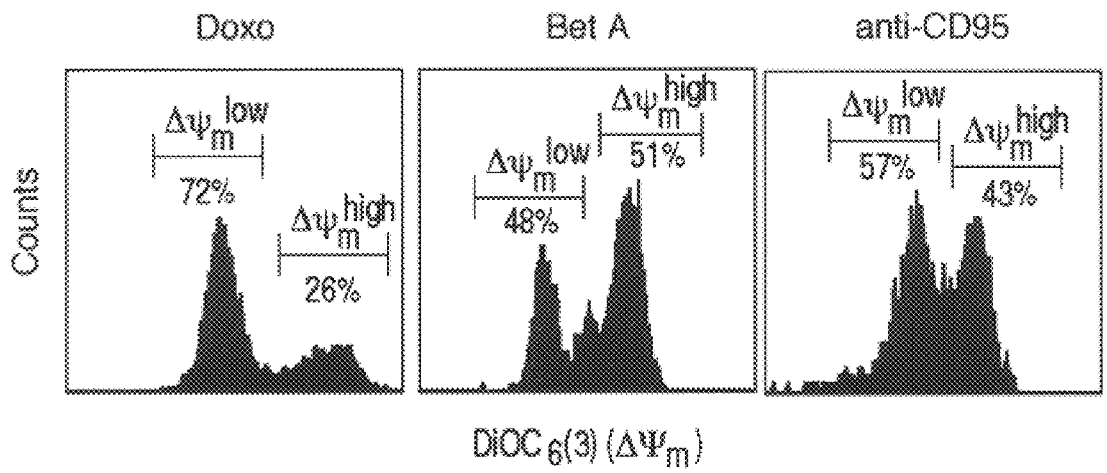
Figures 2, 14B:
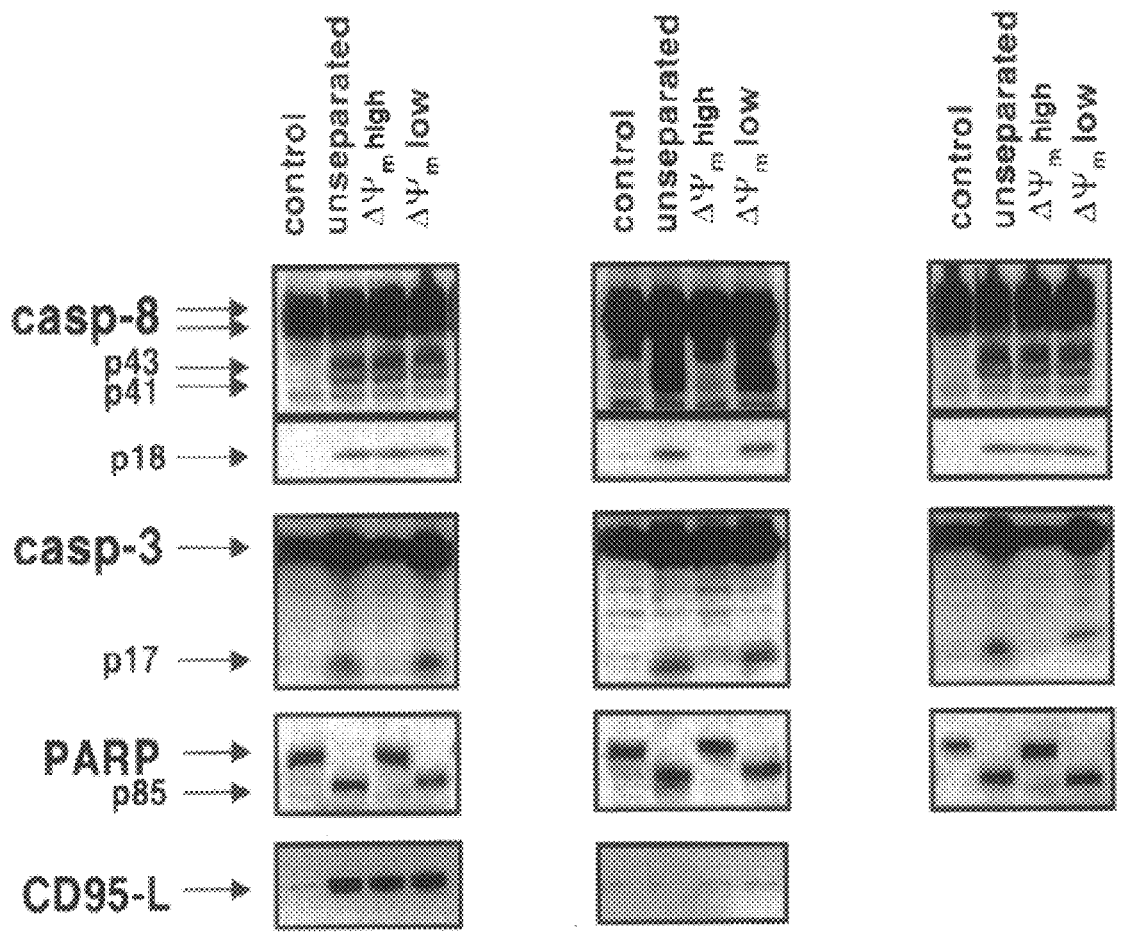

FIGS. 14 B-1 and 14B-2 shows the induction of CD95. SHEP cells transfected with Bcl-2 or Bcl-$X_L$ or a neomycin resistance vector only (Neo) were treated (Lanes+) with 0.5 μg/ml Doxo or 10 μg/ml Bet A for 24 h. CD95 mRNA expression was determined by RT-PCR. Expression of β-actin was used to control RNA integrity and equal gel loading. For Western blot analysis (B), 40 μg protein of cell lysates per lane were separated by 12% SDS-PAGE. Immunodetection of CD95 protein was performed by mouse anti-CD95 moab and enhanced chemiluminescence. For FACS analysis of CD95 protein expression (C), cells were stained with mouse anti-APO-1 moab followed by FITC-conjugated antimouse IgG antibody and analyzed by flow cytometry. Similar results were obtained in three separate experiments.

Both CD95-L and CD95 were induced at the mRNA and protein level in Neo-transfected control cells and Bcl-2 or Bcl-$X_L$ overexpressing cells (FIGS. 13A–C). No significant differences were observed with respect to the kinetics of CD95-L and CD95 induction. A similar increase in CD95 and CD9-L expression was observed following treatment with cisplatinum or VP-16, irrespective of the expression of Bcl-2 or Bcl-$X_L$. These findings suggest that upregulation of CD95-L and CD95 upon doxorubicin treatment occurs independently and upstream of mitochondria. In contrast, no upregulation of CD95-L or CD95 was found at any time point following treatment with betulinic acid (FIGS. 13A and 13B), indicating that betulinic acid triggers apoptosis independently of the CD95-L/receptor system.

Connection of $\Delta\Psi_m$ Disruption to Activation of the Caspase Cascade

FIG. 14B-1 shows that Bcl-2 and Bcl-$X_L$ block activation of downstream caspases. SHEP cells transfected with Bcl-2 or Bcl-$X_L$ or a neomycin resistance vector only (Neo) were treated (Lanes+) with 0.5 μg/ml Doxo or 10 μg/ml Bet A for 24 h. The percentage of treated or untreated cells with $\Delta\Psi_m$ is shown. Forty μg of protein per lane isolated front cell lysates were separated by 15% SDS-PAGE. Immunodetection of caspase-3. caspase-8, and PARP protein was performed by mouse anti-caspase-3 moab. mouse anti-caspase-8 moab, rabbit anti-PARP polyclonal antibody, and enhanced chemiluminescence.

FIG. 14B shows the temporal relationship between $\Delta\Psi_m$ disruption and caspase cleavage. SHEP cells were treated with 0.5 μg/ml Doxorubicin, 10 μg/ml Bet A, or I μg/ml anti-APO-1 for 18 h. stained with $DiOC_6(3)$ and separated on a cytofluorometer into cells with still normal $\Delta\Psi_m$ ($\Delta\Psi_m^{high}$) and cells with a disrupted $\Delta\Psi_m$ ($\Delta\Psi_m^{Low}$). Cell sorting was performed according to the regions of $\Delta\Psi_m^{high}$ or $\Delta\Psi_m^{Low}$ cells as indicated by the histograms. Western blot analysis of cell lysates was performed as described in FIG. 14A.

Upon treatment with doxorubicin, caspase-8 was cleaved into p43 and p41 intermediates and the active p18 subunit, regardless of Bcl-2 or Bcl-$X_L$ overexpression (FIG. 14A). In contrast, proteolytic processing of caspase-3 and PARP was inhibited in Bcl-2 and Bcl-$X_L$ transfected cells (FIG. 14A). Similar data were obtained when cisplatinum or VP-16 were used as chemotherapeutic agents. In contrast, when apoptosis was triggered by betulinic acid, processing of both caspase-8 and caspase-3 was inhibited by Bcl-2 or Bcl-$X_L$. These data indicate that caspase-8 is cleaved upstream of a Bcl-2/Bcl-$X_L$-controlled checkpoint after treatment with doxorubicin, but downstream of this checkpoint following incubation with betulinic acid. In both cases, however, processing of caspase-3 and PARP was prevented by Bcl-2 or Bcl-$X_L$.

To further delineate the relationship between mitochondrial PT (which represents a Bcl-2/Bcl-$X_L$-controlled event), induction of CD95-L and caspase activation, cells treated with doxorubicin or betulinic acid were sorted into cells with still normal $\Delta\Psi_m$ ($DiOC_6(3)^{high}$) and cells with a disrupted $\Delta\Psi_m$ ($DiOC_6(3)^{low}$). After incubation with doxorubicin, CD95-L induction and cleavage of caspase-8 was found in both $\Delta\Psi_m^{high}$ and $\Delta\Psi_m^{low}$ cells (FIG. 14B-2). However, only $\Delta\Psi_m^{low}$ cells displayed cleaved caspase-3 and PARP (FIG. 14B-2). A similar pattern of caspase cleavage was seen when cells were stimulated by CD95 crosslinking (FIG. 14B-2). This indicates that initiation of the apoptosis program by upregulation of CD95/CD95-L and CD95-triggered caspase activation occurs upstream of mitochondria. In contrast, upon incubation with betulinic acid, only $\Delta\Psi_m^{low}$ cells displayed cleaved caspases-3 and -8, in addition to processed PARP (FIG. 14B-2). Thus, caspase-8 activation occurred downstream of the $\Delta\Psi_m$ dissipation in betulinic acid-induced apoptosis, whereas caspase-8 cleavage and CD95-L induction occurred upstream of the $\Delta\Psi_m$ collapse in doxorubicin-induced apoptosis.

Caspase-8 is Activated By Mitochondria Undergoing PT

FIG. 15A shows that caspase-8 is cleaved by mitochondria undergoing PT. SHEP cells transfected with Bcl-2 or Bcl-$X_L$ or a neomycin resistance vector only (Neo) were treated (Lanes+) with 0.5 μg/ml Doxo or 10 μg/ml Bet A for 16 h. Mitochondria were isolated and incubated with cytosolic extracts for 6 h. in the presence or absence of 60 μm Z-VAD.fmk. Western blot analysis was performed as described in FIG. 14A.

FIG. 15B shows that Bcl-2 and Bcl-$X_L$ inhibit cleavage of caspases at the mitochondrial level. Mitochondria (mito) of Doxo- or Bet A-treated vector control cells (Neo) and Bcl-2- or Bcl-$X_L$ overexpressing SHEP cells were incubated with cytosolic extracts of Bel-2- or Bcl-$X_L$-overexpressing cells and vector control cells, respectively, followed by immunodetection of caspase-3 and caspase-8, as described in FIG. 14A.

Mitochondria from doxorubicin- or betulinic acid-treated vector control cells induced cleavage of caspases-3, -8 and PARP in cytosolic extracts (FIG. 15A). This effect was blocked by the broad range caspase inhibitor zVAD-fmk, indicating that protease activity was required for activation of caspases-3 and -8 (FIG. 15A). To confirm that cleavage of caspases depended on mitochondria undergoing PT, similar experiments were performed using Bcl-2 or Bcl-$X_L$ transfected cells in which mitochondria fail to undergo PT subsequent to doxorubicin or betulinic acid treatment (FIG. 12). Mitochondria from Bcl-2 or Bcl-$X_L$ overexpressing cells treated with doxorubicin or betulinic acid did not induce caspase cleavage in cytosolic extracts (FIG. 15A).

Using mitochondria from vector control cells, cleavage of caspases was found in cytosolic extracts of Bcl-2 or Bcl-$X_L$ transfected cells (FIG. 15B). However, processing of caspases was inhibited when mitochondria from Bcl-2 or Bcl-$X_L$ overexpressing cells were used in combination with cytosolic extracts of vector control calls (FIG. 15B). This indicates that deficient cleavage of caspases in Bcl-2 or Bcl-$X_L$ overexpressing cells directly relaxed to blocked mitochondrial function rather than to direct or indirect effects including sequestration of caspases from the cytosol.

Caspase-8 is Cleaved By AIF-Containing Mitochondrial Supernatant, But Not By Cytochrome c FIG. 16A shows that drug-induced release of cyt c from mitochondria. SHEP cells transfected with Bcl-2 or a neomycin resistance vector only (Neo) were treated with 0.5 μg/ml Doxo or 10 μg/ml Bet A for indicated times. Mitochondria and cytosolic extracts (S100 fraction) were prepared as described in "Materials and Methods." Five μg of protein per lane were separated by 15% SDS-PAGE. Immunodetection of cyt c was performed by mouse anti-cyt c moab and enhanced chemiluminescence.

FIG. 16B shows the cleavage of pro-caspase-8 is triggered by AIF but not by cyt c. Cytosolic extracts of SHEP cells transfected with a neomycin resistance vector only (Neo) or Bcl-2 were prepared and incubated with 10 μm cyt c or AIF-containing mitochondrial supernatant. Immunodetection of caspase-3, caspase-8, and PARP was performed as described in FIG. 14A.

After stimulation with doxorubicin or betulinic acid, mitochondrial cytochrome c levels declined, while the concentration of ectopic, cytosolic cytochrome c increased (FIG. 16A). Enforced expression of Bcl-2 or BCl-$X_L$ blocked the mitochondrial release of cytochrome c (FIG. 16A). Addition of purified cytochrome c to cytosolic extracts resulted in the processing of caspase-3 and PARP in both vector control and Bcl-2 overexpressing cells (FIG. 16B), again indicating that the apoptogenic activity was preserved in the cytosol of Bcl-2 overexpressing cells. However, addition of cytochrome c to cytosolic extracts did not induce caspase-8 activation (FIG. 16B).

Incubation of cytosolic extracts with AIF-containing mitochondrial supernatant resulted in cleavage of caspases-3, -8, and PARP (FIG. 16B). Thus, different mitochondrial proteins released during PT activate distinct capases involved in the apoptosis machinery.

E. Example 5

Betulinic Acid Derivatives Induce Apoptosis in Neuroectodermal Cells

The following experiment demonstrates that exemplified betulinic acid derivatives induce apoptosis in a variety of neuroectodermal cells. More specifically, betulinic acid, 28-acetyl-3-β-D-glucosyl betulin ("B10"), 3-β-28-hydroxylup-20(29)-en-3-yl-β-D-glucopyranoside ("B11"), 3-β-3-hydroxylup-20(29)-en-28-yl-β-D-glucopyranoside ("B12"), and 3-(β-D-glucopyranosyloxy)lup-20(29)-en-28-oic acid ("B13") have been tested for specific apoptosis induction using the assays shown in Example 2. See, supra. As depicted in FIG. 17A, in SHEP cells, all derivatives tested demonstrated apoptotic activity that even exceeded that of betulinic acid. In IMR-5 cells, B10, B12, and B13 demonstrated enhanced apoptotic activity when compared to betulinic acid, while B11 showed about the same activity as betulinic acid. (FIG. 17B). Finally, in Kelly cells, all the derivatives tested, B10, B11, B12, and B13, demonstrated an apoptotic activity at least as high as betulinic acid (FIG. 17C).

Sugar derivatives, in particular glucose derivatives have the additional advantage that they may pass the blood/brain barrier actively, through saccharide receptors and channels, in particular glucose channels. Therefore, the derivatives shown have additional advantages for the treatment of tumors located in the brain.

All references cited herein are incorporated herein by reference in their entirety and for all purposes to the same extent as if each individual publication or patent or patent application was specifically and individually indicated to be incorporated by reference in its entirety for all purposes.

What is claimed is:

1. A compound having a structure:

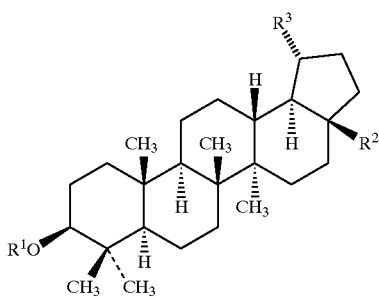

(I)

wherein $R^1$ is selected from the group consisting of hydrogen, —$SO_3H$, —$PO_3H_2$, —$C_1$–$C_{20}$ straight or branched chain alkyl, —$C_2$–$C_{20}$ straight or branched chain alkenyl, —$C_2$–$C_{20}$ straight or branched chain alkynyl, —$(CH_2CH_2O)_nH$, —$(CH_2CH_2O)_nCH_3$, —$(CH_2CH_2O)_nCH_2CH_3$, —$C(O)C_6H_5$, —$C(O)C_1$–$C_{20}$ straight or branched chain alkyl, —$C(O)C_2$–$C_{20}$ straight or branched chain alkenyl, —$C(O)C_2$–$C_{20}$ straight or branched chain alkynyl, myo-inosityl, scyllo-inosityl, a cyclitol, conduritol A, quebrachitol, a monosaccharide, a disaccharide and an oligosaccharide; the —$(CH_2CH_2O)_nH$, myo-inosityl, scyllo-inosityl, cyclitol, conduritol A, quebrachitol, monosaccharide, disaccharide and oligosaccharide being optionally substituted with one or more —$C(O)$ $C_1$–$C_{20}$ straight or branched chain alkyl, —$C(O)$ $C_2$–$C_{20}$ straight or branched chain alkenyl, —$C(O)$ $C_2$–$C_{20}$ straight or branched chain alkynyl, sulfate, or mono-, di- or tri-phosphate groups;

$R^2$ is selected from the group consisting of —$CO_2H$, —$CO_2(C_6H_5)$, —$CO_2(C_1$–$C_{20}$ straight or branched chain alkyl), —$CO_2(C_2$–$C_{20}$ straight or branched chain alkenyl), —$CO_2(C_2$–$C_{20}$ straight or branched chain alkynyl), —$CO_2$(myo-inosityl), —$CO_2$(scyllo-inosityl), —$CO_2$(cyclitol), —$CO_2$(conduritol A), —$CO_2$(quebrachitol), —$CO_2$(monosaccharide), —$CO_2$(disaccharide), —$CO_2$(oligosaccharide), —$CO(OCH_2CH_2)_nOH$, —$CO(OCH_2CH_2)_nOCH_3$, —$CO(OCH_2CH_2)_nOCH_2CH_3$, —$CH_2OH$, —$CH_2OSO_3H$, —$CH_2OPO_3H_2$, —$CH_2O(C_6H_5)$, —$CH_2O(C_1$–$C_{20}$ straight or branched chain alkyl), —$CH_2O(C_2$–$C_{20}$ straight or branched chain alkenyl), —$CH_2O(C_2$–$C_{20}$ straight or branched chain alkynyl), —$CH_2O_2C$ ($C_1$–$C_{20}$ straight or branched chain alkyl), —$CH_2O_2C$ ($C_2$–$C_{20}$ straight or branched chain alkenyl), —$CH_2O_2C(C_2$–$C_{20}$ straight or branched chain alkynyl), —$CH_2O$(myo-inosityl), —$CH_2O$(scyllo-inosityl), —$CH_2O$(cyclitol), —$CH_2O$(conduritol A), —$CH_2O$(quebrachitol), —$CH_2O$(monosaccharide), —$CH_2O$(disaccharide), —$CH_2O$(oligosaccharide), —$CH_2(OCH_2CH_2)_nOH$, —$CH_2(OCH_2CH_2)_nOCH_3$, —$CH_2(OCH_2CH_2)_nOCH_2CH_3$, —$CH_2O_2C$ $(OCH_2CH_2)_nOH$, —$CH_2O_2C(OCH_2CH_2)_nOCH_3$, and —$CH_2O_2C(OCH_2CH_2)_nOCH_2CH_3$; the myo-inosityl, scyllo-inosityl, cyclitol, conduritol A, quebrachitol, monosaccharide, disaccharide, oligosaccharide, —$CH_2$ $(OCH_2CH_2)_nOH$ and —$CH_2O_2C(OCH_2CH_2)_nOH$ being optionally substituted with one or more —$C(O)$ $C_1$–$C_{20}$ straight or branched chain alkyl, —$C(O)$ $C_2$–$C_{20}$ straight or branched chain alkenyl, —$C(O)$ $C_2$–$C_{20}$ straight or branched chain alkynyl, sulfate, or mono-, di- or tri-phosphate groups;

$R^3$ is selected from the group consisting of —$C(CH_3)$ (=$CH_2$) and —$CH(CH_3)_2$;

each n is independently an integer from 1 to 20;

D-enantiomers, L-enantiomers, and racemates thereof;

and pharmaceutically acceptable salts thereof;

with the proviso that the compound of formula I is not:

3β-3-hydroxylup-20(29)-en-28-oic acid ("betulinic acid");

3β-lup-20(29)-ene-3,28-diol ("betulin");

3β-lup-20(29)-ene-3,28-diol diacetate ("3,28-diacetylbetulin");

3β-3-(acetyloxy)lup-20(29)-en-28-oic acid ("3-acetylbetulinic acid");

3β-3-(1-oxobutoxy)lup-20(29)-en-28-oic acid ("3-butyrylbetulinic acid");

3β-3-(2,3-dihydroxycinnamoyl)lup-20(29)-en-28-oic acid ("3-(2,3-dihydroxycinnamoyl)betulinic acid");

3β-lup-20(29)-ene-3,28-diol 3-acetate ("3-acetylbetulin");

3β-lup-20(29)-ene-3,28-diol 28-acetate ("28-acetylbetulin");
3β-3-hydroxylup-20(29)-en-28-oic acid methyl ester ("methyl betulinate");
3β-3-(acetyloxy)lup-20(29)-en-28-oic acid methyl ester ("methyl 3-acetylbetulinate");
3β-3-hydroxylup-20(29)-en-28-oic acid ethyl ester ("ethyl betulinate");
3β-3-hydroxylup-20(29)-en-28-oic acid butyl ester ("butyl betulinate");
3β-lupane-3,28-diol ("dihydrobetulin");
3β-3-hydroxylupan-28-oic acid ("dihydrobetulinic acid");
3β-3-hydroxylupan-28-oic acid methyl ester ("methyl dihydrobetulinate");
3β-3-(acetyloxy)lupan-28-oic acid methyl ester ("methyl 3-acetyldihydrobetulinate");
3β-3-(acetyloxy)-lupan-28-oic acid ("3-acetyldihydro-betulinic acid");
3β-lupan-3,28-diol diacetate ("3,28-diacetyldihydrobetulin");
3β-lupane-3,28-diol dibutanoate ("3,28-dibutyryldihydrobetulin");
3β-3-(3-methyl-1-oxobutoxy)lupan-28-oic acid ("3-(3-methylbutryryl)dihydrobetulinic acid");
3β-3-((1-oxo-2-butenyl)oxy)lup-20(29)-en-28-oic acid ("3-(trans-2-butenyl)betulinic acid");
3β-3-(2,2-dimethyl-1-oxopropoxy)lupan-28-oic acid ("3-(2,2-dimethylpropionyl)dihydrobetulinic acid");
3α-28-hydroxylup-20(29)-en-3-yl-6-O-(6-deoxy-α-L-mannopyranosyl)-β-D-glucopyranoside;
3α-28-hydroxylup-20(29)-en-3-yl-β-D-glucopyranoside;
3α,4α-3-(β-D-glucopyranosyloxy)lup-20(29)-en-28-oic acid;
3-(β-D-glucopyranosyloxy)lup-20(29)-en-28-oic acid;
3β-28-hydroxylup-20(29)-en-3-yl-β-D-glucopyranoside;
3β-3-hydroxylup-20(29)-en-28-yl-β-D-glucopyranoside;
3β-28(acetyloxy)lup-20(29)-en-3-yl-2-deoxy-α-D-arabinohexopyranoside triacetate;
3β-28(acetyloxy)lup-20(29)-en-3-yl-2-deoxy-β-L-arabinohexopyranoside triacetate;
3β-28(acetyloxy)lup-20(29)-en-3-yl-2,6-dideoxy-β-L-arabinohexopyranoside diacetate;
3β-3-(acetyloxy)lup-20(29)-en-28-yl-2-deoxy-α-D-arabinohexopyranoside triacetate;
3β-3-(acetyloxy)lup-20(29)-en-28-yl-2,6-dideoxy-β-L-arabinohexopyranoside diacetate;
3β-28-hydroxylup-20(29)-en-3-yl-2-deoxy-α-D-arabinohexopyranoside;
3β-28-hydroxylup-20(29)-en-3-yl-2-deoxy-β-L-arabinohexopyranoside;
3β-28-hydroxylup-20(29)-en-3-yl-2,6-dideoxy-β-L-arabinohexopyranoside;
3β-3-hydroxylup-20(29)-en-28-yl-2-deoxy-α-D-arabinohexopyranoside;
3β-lup-20(29)-en-3,28-diyl-bis-β-D-glucopyranoside;
3β-lup-20(29)-en-3,28-diyl-bis-4-O-α-D-glucopyranosyl-β-D-glucopyranoside;
3β-lup-20(29)-en-3,28-diyl-bis-(4-O-(2,3,4,6-tetra-O-acetyl-α-D-glucopyranosyl)-β-D-glucopyranoside hexaacetate;
3β-3-((4-O-α-D-glucopyranosyl-β-D-glucopyranosyl)oxy)lup-20(29)-en-28-oic acid;
3β-3-((6-O-β-D-glucopyranosyl-β-D-glucopyranosyl)oxy)lup-20(29)-en-28-oic acid;
3β-3-hydroxylup-20(29)-en-28-yl-2,6-dideoxy-β-L-arabinohexopyranoside;
3β-3-((2-O-α-L-arabinopyranosyl-6-deoxy-β-D-glucopyranosyl)oxy)lup-20(29)-en-28-oic acid;
3β-3-((2-O-β-D-glucopyranosyl-β-D-glucopyranosyl)oxy)lup-20(29)-en-28-oic acid;
3β-3-hydroxylup-20(29)-en-28-oic acid 2,3,4,6-tetra-O-acetyl-β-D-glucopyranosyl ester;
3β-3-hydroxylup-20(29)-en-28-oic acid β-D-galactopyranosyl ester;
3β-hydroxylup-20(29)-en-28-oic acid 4O-β-D-galactopyranosyl-β-D-glucopyranosyl ester;
3β-3-((2,3,4,6-tetra-O-acetyl-β-D-glucopyranosyl)oxy)lup-20(29)-en-28-oic acid methyl ester;
3β-3-(acetyloxy)lup-20(29)-en-28-oic acid 2,3,4,6-tetra-O-acetyl-β-D-glucopyranosyl ester;
3β-3-(acetyloxy)lup-20(29)-en-28-oic acid β-D-glucopyranosyl ester;
3β-3-((2,3,4,6-tetra-O-acetyl-β-D-glucopyranosyl)oxy)lup-20(29)-en-28-oic acid 2,3,4,6-tetra-O-acetyl-β-D-glucopyranosyl ester;
3β-3-((2,3,4,6-tetra-O-acetyl-β-D-glucopyranosyl)oxy)lupan-28-oic acid methyl ester;
3β-3-(acetyloxy)lupan-28-oic acid 2,3,4,6-tetra-O-acetyl-β-D-glucopyranosyl ester;
3α-3-((2,3,4,6-tetra-O-acetyl-β-D-glucopyranosyl)oxy)lup-20(29)-en-28-oic acid;
3β-3-((2,3,4,6-tetra-O-acetyl-β-D-glucopyranosyl)oxy)lup-20(29)-en-28-oic acid;
3β-3-(acetyloxy)lupan-28-oic acid β-D-glucopyranosyl ester;
3β-3-hydroxylup-20(29)-en-28-oic acid β-D-gluco- pyranosyl ester;
3β-3-hydroxylup-20(29)-en-28-oic acid β-D-xylopyranosyl ester;
3β-hydroxylup-20(29)-en-28-oic acid β-D-glucopyranosyl ester 2',3',4',6'-tetrabenzoate;
3β-lup-20(29)-en-28-oic acid (β-D-glucopyranosyloxy)-β-D-glucopyranosyl ester octabenzoate;
3β-lup-20(29)-en-28-oic acid (α-L-arabinopyranosyloxy)-α-L-arabinopyranosyl ester;
3β-lup-20(29)-en-28-oic acid (α-L-arabinopyranosyloxy)-α-L-arabinopyranosyl ester hexabenzoate;
3β-3-(β-D-glucopyranosyloxy)lup-20(29)-en-28-oic acid methyl ester;
3β-3-(β-D-glucopyranosyloxy)lupan-28-oic acid methyl ester;
3β-3-hydroxylupan-28-oic acid β-D-glucopyranosyl ester;
3β-17-carboxy-28-norlup-20(29)-en-3-yl-3-O-β-D-xylopyranosyl-β-D-glucopyranosiduronic acid;
3β-17-carboxy-28-norlup-20(29)-en-3-yl-2-O-β-D-xylopyranosyl-β-D-glucopyranosiduronic acid;
3β-3-(β-D-glucopyranosyloxy)lup-20(29)-en-28-oic acid 6-O-β-D-glucopyranosyl-β-D-glucopyranosyl ester;
3α-3-hydroxylup-20(29)-en-28-oic acid O-6-deoxy-α-L-mannopyranosyl-(1→4)-O-β-D-glucopyranosyl-(1→6)-O-β-D-glucopyranosyl ester;
3α-3-(β-D-glucopyranosyloxy)lup-20(29)-en-28-oic acid O-6-deoxy-α-L-mannopyranosyl-(1→4)-O-β-D-glucopyranosyl-(1→6)-O-β-D-glucopyranosyl ester;
3β-3-(β-D-glucopyranosyloxy)lup-20(29)-en-28-oic acid O-6-deoxy-α-L-mannopyranosyl-(1→4)-O-β-D-glucopyranosyl-(1→6)-O-β-D-glucopyranosyl ester;
3β-28-methoxy-28-oxolup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid methyl ester diacetate;
3β-17-carboxy-28-norlup-20(29)-en-3-yl-O-6-deoxy-α-L-mannopyranosyl-(1→2)-O-β-D-glucopyranosyl-(1→2)-β-D-glucopyranosiduronic acid;
3β-17-carboxy-28-norlup-20(29)-en-3-yl-O-6-deoxy-α-L-mannopyranosyl-(1→2)-O-β-D-xylopyranosyl-(1→2)-β-D-glucopyranosiduronic acid;

3β-17-carboxy-28-norlup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid diacetate;

3β-17-carboxy-28-norlup-20(29)-en-3-yl-O-2,3,4-tri-O-acetyl-6-deoxy-α-L-mannopyranosyl-(1→2)-O-3,4-di-O-acetyl-β-D-xylopyranosyl-(1→2)-β-D-glucopyranosiduronic acid diacetate;

3β-28-methoxy-28-oxolup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid methyl ester diacetate;

3β-28-methoxy-28-oxolup-20(29)-en-3-yl-O-2,3,4-tri-O-acetyl-6-deoxy-α-L-mannopyranosyl-(1→2)-O-3,4-di-O-acetyl-β-D-xylopyranosyl-(1→2)-β-D-glucopyranosiduronic acid methyl ester diacetate;

3β-3-((O-α-L-arabinofuranosyl-(1→2)-O-6-deoxy-α-L-mannopyranosyl-(1→4)-β-D-glucopyranosyl)oxy)-lup-20(29)-en-28-oic acid;

3β-3-((O-α-L-arabinofuranosyl-(1→2)-O-6-deoxy-α-L-mannopyranosyl-(1→4)-β-D-glucopyranosyl)oxy)-lup-20(29)-en-28-oic acid methyl ester;

3β-28-hydroxylup-20(29)-en-3-yl-4-O-β-D-glucopyranosyl-β-D-glucopyranoside;

3β-28-hydroxylup-20(29)-en-3-yl-4-O-α-D-glucopyranosyl-β-D-glucopyranoside;

3β-3-hydroxylup-20(29)-en-28-yl-4-O-α-D-glucopyranosyl-β-D-glucopyranoside;

3β-28-hydroxylup-20(29)-en-3-yl-β-D-xylopyranoside;

3-(β-D-glucopyranosyloxy)lup-20(29)-en-28-oic acid O-6-deoxy-α-L-mannopyranosyl-(1→4)-O-β-D-glucopyranosyl-(1→6)-O-β-D-glucopyranosyl ester;

3α-lup-20(29)-en-28-oic acid 3-(β-D-glucopyranosyloxy)-O-6-deoxy-α-L-mannopyranosyl-(1→4)-O-β-D-glucopyranosyl-(1→6)-O-β-D-glucopyranosyl ester;

3α,4-α-3-(β-D-glucopyranosyloxy)lup-20(29)-en-28-oic acid;

3α-lup-20(29)-en-28-oic acid 3-((O-6-acetyl-β-D-glucopyranosyl)oxy)-O-6-deoxy-α-L-mannopyranosyl-(1→4)-O-β-D-glucopyranosyl-(1→6)-O-β-D-glucopyranosyl ester;

3β-28-hydroxylup-20(29)-en-3-yl-O-α-D-glucopyranosyl-(1→4)-O-α-D-glucopyranosyl-(1→4)-O-βD-glucopyranosyl-(1→4)-β-D-glucopyranoside;

3α-3-(sulfooxy)lup-20(29)-en-28-oic acid 28-O-6-deoxy-α-L-mannopyranosyl-(1→4)-O-α-D-glucopyranosyl-(1→6)-β-D-glucopyranosyl ester;

3-(sulfooxy)lup-20(29)-en-28-oic acid 28-(O-2,3,4-tri-O-acetyl-6-deoxy-α-L-mannopyranosyl-(1→4)-O-2,3,6-tri-O-acetyl-β-D-glucopyranosyl-(1→6)-2,3,4-tri-O-acetyl-β-D-glucopyranosyl) ester;

3α-3-(acetyloxy)lup-20(29)-en-28-oic acid O-2,3,4-tri-O-acetyl-6-deoxy-α-L-mannopyranosyl-(1→4)-O-2,3,6-tri-O-acetyl-β-D-glucopyranosyl-(1→6)-2,3,4-tri-O-acetyl-β-D-glucopyranosyl) ester;

28-(acetyloxy)lup-20(29)-en-3-yl-4-O-(2,3,4,6-teta-O-acetyl-α-D-glucopyranosyl)-β-D-glucopyranoside triacetate;

3β-28-(acetyloxy)lup-20(29)-en-3-yl-4-O-(2,3,4,6-tetra-O-acetyl-β-D-glucopyranosyl)-β-D-glucopyranoside triacetate;

3β-3-(acetyloxy)lup-20(29)-en-28-yl-4-O-(2,3,4,6-tetra-O-acetyl-α-D-glucopyranosyl)-β-D-glucopyranoside triacetate;

3β-3-((2,3,4,6-tetra-O-acetyl-βD-glucopyranosyl)oxy)lup-20(29)-en-28-yl-β-D-glucopyranoside tetraacetate;

3β-28-(acetyloxy)lup-20(29)-en-3-yl-β-D-glucopyranoside tetraacetate;

3β-3-(acetyloxy)lup-20(29)-en-28-yl-β-D-glucopyranoside tetraacetate;

3β-lup-20(29)-en-3-yl-β-D-glucopyranoside tetraacetate;

3β-lup-20(29)-en-3-yl-6-deoxy-α-L-mannopyranoside;

3β-3-((6-deoxy-2-O-β-D-glucopyranosyl-α-L-mannopyranosyl)oxy)lup-20(29)-en-28-oic acid;

3β-3-((6-deoxy-α-L-mannopyranosyl)oxy)lup-20(29)-en-28-oic acid;

3β-lup-20(29)-en-3-yl-4-O-β-D-xylopyranosyl-β-D-glucopyranoside;

3β-28-(acetyloxy)lup-20(29)-en-3-yl-α-D-glucopyranoside tetraacetate;

3β-3-hydroxylup-20(29)-en-28-yl-β-D-glucopyranoside 2,3,4,6-tetraacetate;

3β-28-((6-O-D-apio-β-D-furanosyl-β-D-glucopyranosyl)oxy)-28-oxolup-20(29)-en-3-yl-4-O-β-D-galactopyranosyl-β-D-glucopyranosiduronic acid;

3β-3-((2-propenyl)oxy)lup-20(29)-en-28-oic acid ("3-O-allylbetulinic acid");

3β-3,28-dimethoxylup-20(29)-ene ("3,28-di-O-methylbetulin");

3β-3,28-dimethoxylupane ("3,28-di-O-methyldihydrobetulin");

3β-28-methoxylupan-3-ol ("28-methyldihydrobetulin");

3β-3-methoxylup-20(29)-en-28-oic acid ("3-O-methylbetulinic acid");

3β-3-methoxylup-20(29)-en-28-oic acid methyl ester ("methyl 3-O-methylbetulinate");

8ξ-2,6-anhydro-9-O-((3β,18β)-17-carboxy-28-norlupan-3-yl)-1,7,8-trideoxy-8-methyl-3,4,5-tris-O-(phenylmethyl)-L-glycero-D-galactononitol;

2,6-anhydro-9-O-((3β,18β)-17-carboxy-28-norlup-20(29)-en-3-yl)-1,7,8-trideoxy-8-methylene-3,4,5-tris-O-(phenylmethyl)-L-glycero-D-galactononitol;

3α-3-methoxylup-20(29)-en-28-oic acid; or

3α-3-methoxylup-20(29)-en-28-oic acid methyl ester.

2. A compound having the structure 3β-28-(acetyloxy)lup-20(29)-en-3-yl-β-D-glucopyranoside ("28-acetyl-3-β-D-glucosylbetulin"), a D-enantiomer, L-enantiomer or racemate thereof, or a pharmaceutically acceptable salt thereof.

3. A compound having the structure 3β-28-(acetyloxy)lup-20(29)-en-3-yl-β-D-galactopyranoside ("28-acetyl-3-β-D-galactosylbetulin"), a D-enantiomer, L-enantiomer or racemate thereof, or a pharmaceutically acceptable salt thereof.

4. A compound having the structure 3β-3-(acetyloxy)lup-20(29)-en-28-yl-β-D-glucopyranoside ("3-acetyl-28-β-D-glucosylbetulin"), a D-enantiomer, L-enantiomer or racemate thereof, or a pharmaceutically acceptable salt thereof.

5. A compound having a structure selected form the group consisting of 28-acetyl-3-β-D-glucosyl betulin, 28-acetyl-3-β-D-galactosyl betulin, and 3-acetyl-28-β-D-glucosyl betulin.

6. A pharmaceutical composition comprising the compound of claim 1 and a pharmaceutically acceptable carrier.

7. A pharmaceutical composition comprising the compound of claim 2 and a pharmaceutically acceptable carrier.

8. A pharmaceutical composition comprising the compound of claim 3 and a pharmaceutically acceptable carrier.

9. A pharmaceutical composition comprising the compound of claim 4 and a pharmaceutically acceptable carrier.

10. A pharmaceutical composition comprising the compound of claim 5 and a pharmaceutically acceptable carrier.

11. A method for treating a neuroectodermal tumor in a subject in need, comprising administering a therapeutically effective amount of a pharmaceutical composition comprising a compound according to the formula:

(I)

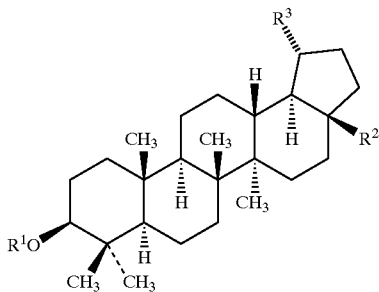

wherein

R¹ is selected from the group consisting of hydrogen, —SO₃H, —PO₃H₂, —C₁–C₂₀ straight or branched chain alkyl, —C₂–C₂₀ straight or branched chain alkenyl, —C₂–C₂₀ straight or branched chain alkynyl, —(CH₂CH₂O)$_n$H, —(CH₂CH₂O)$_n$CH₃, —(CH₂CH₂O)$_n$CH₂CH₃, —C(O)C₆H₅, —C(O) C₁–C₂₀ straight or branched chain alkyl, —C(O) C₂–C₂₀ straight or branched chain alkenyl, —C(O) C₂–C₂₀ straight or branched chain alkynyl, myo-inosityl, scyllo-inosityl, a cyclitol, conduritol A, quebrachitol, a monosaccharide, a disaccharide and an oligosaccharide; the —(CH₂CH₂O)$_n$H, myo-inosityl, scyllo-inosityl, cyclitol, conduritol A, quebrachitol, monosaccharide, disaccharide and oligosaccharide being optionally substituted with one or more —C(O) C₁–C₂₀ straight or branched chain alkyl, —C(O) C₂–C₂₀ straight or branched chain alkenyl, —C(O) C₂–C₂₀ straight or branched chain alkynyl, sulfate, or mono-, di- or tri-phosphate groups;

R² is selected from the group consisting of —CO₂H, —CO₂(C₆H₅), —CO₂(C₁–C₂₀ straight or branched chain alkyl), —CO₂(C₂–C₂₀ straight or branched chain alkenyl), —CO₂(C₂–C₂₀ straight or branched chain alkynyl), —CO₂(myo-inosityl), —CO₂(scyllo-inosityl), —CO₂(cyclitol), —CO₂(conduritol A), —CO₂(quebrachitol), —CO₂(monosaccharide), —CO₂(disaccharide), —CO₂(oligosaccharide), —CO (OCH₂CH₂)$_n$OH, —CO(OCH₂CH₂)$_n$OCH₃, —CO (OCH₂CH₂)$_n$OCH₂CH₃, —CH₂OH, —CH₂OSO₃H, —CH₂OPO₃H₂, —CH₂O(C₆H₅), —CH₂O(C₁–C₂₀ straight or branched chain alkyl), —CH₂O(C₂–C₂₀ straight or branched chain alkenyl), —CH₂O(C₂–C₂₀ straight or branched chain alkynyl), —CH₂O₂C (C₁–C₂₀ straight or branched chain alkyl), —CH₂O₂C (C₂–C₂₀ straight or branched chain alkenyl), —CH₂O₂C(C₂–C₂₀ straight or branched chain alkynyl), —CH₂O(myo-inosityl), —CH₂O(scyllo-inosityl), —CH₂O(cyclitol), —CH₂O(conduritol A), —CH₂O(quebrachitol), —CH₂O(monosaccharide), —CH₂O(disaccharide), —CH₂O(oligosaccharide), —CH₂(OCH₂CH₂)$_n$OH, —CH₂(OCH₂CH₂)$_n$OCH₃, —CH₂(OCH₂CH₂)$_n$OCH₂CH₃, —CH₂O₂C (OCH₂CH₂)$_n$OH, —CH₂O₂C(OCH₂CH₂)$_n$OCH₃, and —CH₂O₂C(OCH₂CH₂)$_n$OCH₂CH₃; the myo-inosityl, scyllo-inosityl, cyclitol, conduritol A, quebrachitol, monosaccharide, disaccharide, oligosaccharide, —CH₂ (OCH₂CH₂)$_n$OH and —CH₂O₂C(OCH₂CH₂)$_n$OH being optionally substituted with one or more —C(O) C₁–C₂₀ straight or branched chain alkyl, —C(O) C₂–C₂₀ straight or branched chain alkenyl, —C(O) C₂–C₂₀ straight or branched chain alkynyl, sulfate, or mono-, di- or tri-phosphate groups;

R³ is selected from the group consisting of —C(CH₃) (=CH₂) and —CH(CH₃)₂; and wherein each n is independently an integer from 1 to 20;

a D-enantiomer, L-enantiomer, or racemate thereof;

or a pharmaceutically acceptable salt thereof.

12. A method for treating a neuroectodermal tumor in a subject in need, comprising administering a therapeutically effective amount of a pharmaceutical composition comprising a compound selected from the group consisting of:

3β-3-hydroxylup-20(29)-en-28-oic acid ("betulinic acid");
3β-lup-20(29)-ene-3,28-diol ("betulin");
3β-lup-20(29)-ene-3,28-diol diacetate ("3,28-diacetylbetulin");
3β-3-(acetyloxy)lup-20(29)-en-28-oic acid ("3-acetylbetulinic acid");
3β-3-(1-oxobutoxy)lup-20(29)-en-28-oic acid ("3-butyrylbetulinic acid");
3β-3-(2,3-dihydroxycinnamoyl)lup-20(29)-en-28-oic acid ("3-(2,3-dihydroxycinnamoyl)betulinic acid");
3β-lup-20(29)-ene-3,28-diol 3-acetate ("3-acetylbetulin");
3β-lup-20(29)-ene-3,28-diol 28-acetate ("28-acetylbetulin");
3β-3-hydroxylup-20(29)-en-28-oic acid methyl ester ("methyl betulinate");
3β-3-(acetyloxy)lup-20(29)-en-28-oic acid methyl ester ("methyl 3-acetylbetulinate");
3β-3-hydroxylup-20(29)-en-28-oic acid ethyl ester ("ethyl betulinate");
3β-3-hydroxylup-20(29)-en-28-oic acid butyl ester ("butyl betulinate");
3β-lupane-3,28-diol ("dihydrobetulin");
3β-3-hydroxylupan-28-oic acid ("dihydrobetulinic acid");
3β-3-hydroxylupan-28-oic acid methyl ester ("methyl dihydrobetulinate");
3β-3-(acetyloxy)lupan-28-oic acid methyl ester ("methyl 3-acetyldihydrobetulinate");
3β-3-(acetyloxy)-lupan-28-oic acid ("3-acetyldihydro-betulinic acid");
3β-lupane-3,28-diol diacetate ("3,28-diacetyldihydrobetulin");
3β-lupane-3,28-diol dibutanoate ("3,28-dibutyryldihydrobetulin");
3β-3-(3-methyl-1-oxobutoxy)lupan-28-oic acid ("3-(3-methylbutryryl)dihydrobetulinic acid");
3β-3-((1-oxo-2-butenyl)oxy)lup-20(29)-en-28-oic acid ("3-(trans-2-butenyl)betulinic acid");
3β-3-(2,2-dimethyl-1-oxopropoxy)lupan-28-oic acid ("3-(2,2-dimethylpropionyl)dihydrobetulinic acid");
3α-28-hydroxylup-20(29)-en-3-yl-6-O-(6-deoxy-α-L-mannopyranosyl)-β-D-glucopyranoside;
3α-28-hydroxylup-20(29)-en-3-yl-β-D-glucopyranoside;
3α,4α-3-(β-D-glucopyranosyloxy)lup-20(29)-en-28-oic acid;
3-(β-D-glucopyranosyloxy)lup-20(29)-en-28-oic acid;
3β-28-hydroxylup-20(29)-en-3-yl-β-D-glucopyranoside;
3β-3-hydroxylup-20(29)-en-28-yl-β-D-glucopyranoside;
3β-28(acetyloxy)lup-20(29)-en-3-yl-2-deoxy-α-D-arabinohexopyranoside triacetate;
3β-28(acetyloxy)lup-20(29)-en-3-yl-2-deoxy-β-L-arabinohexopyranoside triacetate;
3β-28(acetyloxy)lup-20(29)-en-3-yl-2,6-dideoxy-β-L-arabinohexopyranoside diacetate;
3β-3-(acetyloxy)lup-20(29)-en-28-yl-2-deoxy-α-D-arabinohexopyranoside triacetate;
3β-3-(acetyloxy)lup-20(29)-en-28-yl-2,6-dideoxy-β-L-arabinohexopyranoside diacetate;
3β-28-hydroxylup-20(29)-en-3-yl-2-deoxy-α-D-arabinohexopyranoside;

3β-28-hydroxylup-20(29)-en-3-yl-2-deoxy-β-L-arabinohexopyranoside;
3β-28-hydroxylup-20(29)-en-3-yl-2,6-dideoxy-β-L-arabinohexopyranoside;
3β-3-hydroxylup-20(29)-en-28-yl-2-deoxy-α-D-arabinohexopyranoside;
3β-lup-20(29)-en-3,28-diyl-bis-β-D-glucopyranoside;
3β-lup-20(29)-en-3,28-diyl-bis-4-O-α-D-glucopyranosyl-β-D-glucopyranoside;
3β-lup-20(29)-en-3,28-diyl-bis-(4-O-(2,3,4,6-tetra-O-acetyl-α-D-glucopyranosyl)-β-D-glucopyranoside hexaacetate;
3β-3-((4-O-α-D-glucopyranosyl-β-D-glucopyranosyl)oxy)lup-20(29)-en-28-oic acid;
3β-3-((6-O-β-D-glucopyranosyl-β-D-glucopyranosyl)oxy)lup-20(29)-en-28-oic acid;
3β-3-hydroxylup-20(29)-en-28-yl-2,6-dideoxy-β-L-arabinohexopyranoside;
3β-3-((2-O-α-L-arabinopyranosyl-6-deoxy-β-D-glucopyranosyl)oxy)lup-20(29)-en-28-oic acid;
3β-3-((2-O-β-D-glucopyranosyl-β-D-glucopyranosyl)oxy)lup-20(29)-en-28-oic acid;
3β-3-hydroxylup-20(29)-en-28-oic acid 2,3,4,6-tetra-O-acetyl-β-D-glucopyranosyl ester;
3β-3-hydroxylup-20(29)-en-28-oic acid β-D-galactopyranosyl ester;
3β-3-hydroxylup-20(29)-en-28-oic acid 4-O-β-D-galactopyranosyl-β-D-glucopyranosyl ester;
3β-3-((2,3,4,6-tetra-O-acetyl-β-D-glucopyranosyl)oxy)lup-20(29)-en-28-oic acid methyl ester;
3β-3-(acetyloxy)lup-20(29)-en-28-oic acid 2,3,4,6-tetra-O-acetyl-β-D-glucopyranosyl ester;
3β-3-(acetyloxy)lup-20(29)-en-28-oic acid β-D-glucopyranosyl ester;
3β-3-((2,3,4,6-tetra-O-acetyl-β-D-glucopyranosyl)oxy)lup-20(29)-en-28-oic acid 2,3,4,6-tetra-O-acetyl-β-D-glucopyranosyl ester;
3β-3-((2,3,4,6-tetra-O-acetyl-β-D-glucopyranosyl)oxy)lupan-28-oic acid methyl ester;
3β-3-(acetyloxy)lupan-28-oic acid 2,3,4,6-tetra-O-acetyl-β-D-glucopyranosyl ester;
3α-3-((2,3,4,6-tetra-O-acetyl-β-D-glucopyranosyl)oxy)lup-20(29)-en-28-oic acid;
3β-3-((2,3,4,6-tetra-O-acetyl-β-D-glucopyranosyl)oxy)lup-20(29)-en-28-oic acid;
3β-3-(acetyloxy)lupan-28-oic acid β-D-glucopyranosyl ester;
3β-3-hydroxylup-20(29)-en-28-oic acid β-D-glucopyranosyl ester;
3β-3-hydroxylup-20(29)-en-28-oic acid β-D-xylopyranosyl ester;
3β-hydroxylup-20(29)-en-28-oic acid β-D-glucopyranosyl ester 2',3',4',6'-tetrabenzoate;
3β-lup-20(29)-en-28-oic acid (β-D-glucopyranosyloxy)-β-D-glucopyranosyl ester octabenzoate;
3β-lup-20(29)-en-28-oic acid (α-L-arabinopyranosyloxy)-α-L-arabinopyranosyl ester;
3β-lup-20(29)-en-28-oic acid (α-L-arabinopyranosyloxy)-α-L-arabinopyranosyl ester hexabenzoate;
3β-3-(β-D-glucopyranosyloxy)lup-20(29)-en-28-oic acid methyl ester;
3β-3-(β-D-glucopyranosyloxy)lupan-28-oic acid methyl ester;
3β-3-hydroxylupan-28-oic acid β-D-glucopyranosyl ester;
3β-17-carboxy-28-norlup-20(29)-en-3-yl-3-O-β-D-xylopyranosyl-β-D-glucopyranosiduronic acid;
3β-17-carboxy-28-norlup-20(29)-en-3-yl-2-O-β-D-xylopyranosyl-β-D-glucopyranosiduronic acid;
3β-3-(β-D-glucopyranosyloxy)lup-20(29)-en-28-oic acid 6-O-β-D-glucopyranosyl-β-D-glucopyranosyl ester;
3α-3-hydroxylup-20(29)-en-28-oic acid O-6-deoxy-α-L-mannopyranosyl-(1→4)-O-β-D-glucopyranosyl-(1→6)-O-β-D-glucopyranosyl ester;
3α-3-(β-D-glucopyranosyloxy)lup-20(29)-en-28-oic acid O-6-deoxy-α-L-mannopyranosyl-(1→4)-O-β-D-glucopyranosyl-(1→6)-O-β-D-glucopyranosyl ester;
3β-3-(β-D-glucopyranosyloxy)lup-20(29)-en-28-oic acid O-6-deoxy-α-L-mannopyranosyl-(1→4)-O-β-D-glucopyranosyl-(1→6)-O-β-D-glucopyranosyl ester;
3β-28-methoxy-28-oxolup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid methyl ester diacetate;
3β-17-carboxy-28-norlup-20(29)-en-3-yl-O-6-deoxy-α-L-mannopyranosyl-(1→2)-O-β-D-glucopyranosyl-(1→2)-β-D-glucopyranosiduronic acid;
3β-17-carboxy-28-norlup-20(29)-en-3-yl-O-6-deoxy-α-L-mannopyranosyl-(1→2)-O-β-D-xylopyranosyl-(1→2)-β-D-glucopyranosiduronic acid;
3β-17-carboxy-28-norlup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid diacetate;
3β-17-carboxy-28-norlup-20(29)-en-3-yl-O-2,3,4-tri-O-acetyl-6-deoxy-α-L-mannopyranosyl-(1→2)-O-3,4-di-O-acetyl-β-D-xylopyranosyl-(1→2)-β-D-glucopyranosiduronic acid diacetate;
3β-28-methoxy-28-oxolup-20(29)-en-3-yl-O-2,3,4-tri-O-acetyl-6-deoxy-α-L-mannopyranosyl-(1→2)-O-3,4,6-tri-O-acetyl-β-D-glucopyranosyl-(1→2)-β-D-glucopyranosiduronic acid methyl ester diacetate;
3β-28-methoxy-28-oxolup-20(29)-en-3-yl-O-2,3,4-tri-O-acetyl-6-deoxy-α-L-mannopyranosyl-(1→2)-O-3,4-di-O-acetyl-β-D-xylopyranosyl-(1→2)-β-D-glucopyranosiduronic acid methyl ester diacetate;
3β-3-((O-α-L-arabinofuranosyl-(1→2)-O-6-deoxy-α-L-mannopyranosyl-(1→4)-β-D-glucopyranosyl)oxy)-lup-20(29)-en-28-oic acid;
3β-3-((O-α-L-arabinofuranosyl-(1→2)-O-6-deoxy-α-L-mannopyranosyl-(1→4)-β-D-glucopyranosyl)oxy)-lup-20(29)-en-28-oic acid methyl ester;
3β-28-hydroxylup-20(29)-en-3-yl-4-O-β-D-glucopyranosyl-β-D-glucopyranoside;
3β-28-hydroxylup-20(29)-en-3-yl-4-O-α-D-glucopyranosyl-β-D-glucopyranoside;
3β-3-hydroxylup-20(29)-en-28-yl-4-O-α-D-glucopyranosyl-β-D-glucopyranoside;
3β-28-hydroxylup-20(29)-en-3-yl-β-D-xylopyranoside;
3-(β-D-glucopyranosyloxy)lup-20(29)-en-28-oic acid O-6-deoxy-α-L-mannopyranosyl-(1→4)-O-β-D-glucopyranosyl-(1→6)-O-β-D-glucopyranosyl ester;
3α-lup-20(29)-en-28-oic acid 3-(β-D-glucopyranosyloxy)-O-6-deoxy-α-L-mannopyranosyl-(1→4)-O-β-D-glucopyranosyl-(1→6)-O-β-D-glucopyranosyl ester;
3α,4-α-3-(β-D-glucopyranosyloxy)lup-20(29)-en-28-oic acid;
3α-lup-20(29)-en-28-oic acid 3-((O-6-acetyl-β-D-glucopyranosyl)oxy)-O-6-deoxy-α-L-mannopyranosyl-(1→4)-O-β-D-glucopyranosyl-(1→6)-O-β-D-glucopyranosyl ester;
3β-28-hydroxylup-20(29)-en-3-yl-O-α-D-glucopyranosyl-(1→4)-O-α-D-glucopyranosyl-(1→4)-O-β-D-glucopyranosyl-(1→4)-β-D-glucopyranoside;
3α-3-(sulfooxy)lup-20(29)-en-28-oic acid 28-O-6-deoxy-α-L-mannopyranosyl-(1→4)-O-β-D-glucopyranosyl-(1→6)-β-D-glucopyranosyl ester;

3-(sulfooxy)lup-20(29)-en-28-oic acid 28-(O-2,3,4-tri-O-acetyl-6-deoxy-α-L-mannopyranosyl-(1→4)-O-2,3,6-tri-O-acetyl-β-D-glucopyranosyl-(1→6)-2,3,4-tri-O-acetyl-β-D-glucopyranosyl) ester;

3α-3-(acetyloxy)lup-20(29)-en-28-oic acid O-2,3,4-tri-O-acetyl-6-deoxy-α-L-mannopyranosyl-(1→4)-O-2,3,6-tri-O-acetyl-β-D-glucopyranosyl-(1→6)-2,3,4-tri-O-acetyl-β-D-glucopyranosyl) ester;

28-(acetyloxy)lup-20(29)-en-3-yl-4-O-(2,3,4,6-tetra-O-acetyl-α-D-glucopyranosyl)-β-D-glucopyranoside triacetate;

3β-28-(acetyloxy)lup-20(29)-en-3-yl-4-O-(2,3,4,6-tetra-O-acetyl-β-D-glucopyranosyl)-β-D-glucopyranoside triacetate;

3β-3-(acetyloxy)lup-20(29)-en-28-yl-4-O-(2,3,4,6-tetra-O-acetyl-α-D-glucopyranosyl)-β-D-glucopyranoside triacetate;

3β-3-((2,3,4,6-tetra-O-acetyl-β-D-glucopyranosyl)oxy)lup-20(29)-en-28-yl-β-D-glucopyranoside tetraacetate;

3β-28-(acetyloxy)lup-20(29)-en-3-yl-β-D-glucopyranoside tetraacetate;

3β-3-(acetyloxy)lup-20(29)-en-28-yl-β-D-glucopyranoside tetraacetate;

3β-lup-20(29)-en-3-yl-β-D-glucopyranoside tetraacetate;

3β-lup-20(29)-en-3-yl-6-deoxy-α-L-mannopyranoside;

3β-3-((6-deoxy-2-O-β-D-glucopyranosyl-α-L-mannopyranosyl)oxy)lup-20(29)-en-28-oic acid;

3β-3-((6-deoxy-α-L-mannopyranosyl)oxy)lup-20(29)-en-28-oic acid;

3β-lup-20(29)-en-3-yl-4-O-β-D-xylopyranosyl-β-D-glucopyranoside;

3β-28-(acetyloxy)lup-20(29)-en-3-yl-α-D-glucopyranoside tetraacetate;

3β-3-hydroxylup-20(29)-en-28-yl-β-D-glucopyranoside 2,3,4,6-tetraacetate;

3β-28-((6-O-D-apio-β-D-furanosyl-β-D-glucopyranosyl)oxy)-28-oxolup-20(29)-en-3-yl-4-O-β-D-galactopyranosyl-β-D-glucopyranosiduronic acid;

3β-3-((2-propenyl)oxy)lup-20(29)-en-28-oic acid ("3-O-allylbetulinic acid");

3β-3,28-dimethoxylup-20(29)-ene ("3,28-di-O-methylbetulin");

3β-3,28-dimethoxylupane ("3,28-di-O-methyldihydrobetulin");

3β-28-methoxylupan-3-ol ("28-methyldihydrobetulin");

3β-3-methoxylup-20(29)-en-28-oic acid ("3-O-methylbetulinic acid");

3β-3-methoxylup-20(29)-en-28-oic acid methyl ester ("methyl 3-O-methylbetulinate");

8ξ-2,6-anhydro-9-O-((3β,18β)-17-carboxy-28-norlupan-3-yl)-1,7,8-trideoxy-8-methyl-3,4,5-tris-O-(phenylmethyl)-L-glycero-D-galactononitol;

2,6-anhydro-9-O-((3β,18β)-17-carboxy-28-norlup-20(29)-en-3-yl)-1,7,8-trideoxy-8-methylene-3,4,5-tris-O-(phenylmethyl)-L-glycero-D-galactononitol;

3α-3-methoxylup-20(29)-en-28-oic acid;

3α-3-methoxylup-20(29)-en-28-oic acid methyl ester;

3β-28-(acetyloxy)lup-20(29)-en-3-yl-β-D-glucopyranoside ("28-acetyl-3-β-D-glucosylbetulin");

3β-28-(acetyloxy)lup-20(29)-en-3-yl-β-D-galactopyranoside ("28-acetyl-3-β-D-galactosylbetulin"); and 3β-3-(acetyloxy)lup-20(29)-en-28-yl-β-D-glucopyranoside ("3-acetyl-28-β-D-glucosylbetulin"), a D-enantiomer, L-enantiomer or racemate thereof, or a pharmaceutically acceptable salt thereof.

13. A method for treating a neuroectodermal tumor in a subject in need of said treatment, comprising administering a therapeutically effective amount of the pharmaceutical composition of claim 6.

14. A method for treating a neuroectodermal tumor in a subject in need of said treatment, comprising administering a therapeutically effective amount of the pharmaceutical composition of claim 7.

15. A method for treating a neuroectodermal tumor in a subject in need of said treatment, comprising administering a therapeutically effective amount of the pharmaceutical composition of claim 8.

16. A method for treating a neuroectodermal tumor in a subject in need of said treatment, comprising administering a therapeutically effective amount of the pharmaceutical composition of claim 9.

17. A method for treating a neuroectodermal tumor in a subject in need of said treatment, comprising administering a therapeutically effective amount of the pharmaceutical composition of claim 10.

18. The method of any of claims 11, 12, 13, 14, 15, 16, or 17, wherein the neuroectodermal tumor is a neuroblastoma, a medulloblastoma, or an Ewing's sarcoma.

* * * * *